(12) United States Patent
Zhang et al.

(10) Patent No.: US 12,006,344 B2
(45) Date of Patent: *Jun. 11, 2024

(54) MIC-1 COMPOUNDS AND USE THEREOF

(71) Applicant: Novo Nordisk A/S, Bagsvaerd (DK)

(72) Inventors: Xujia Zhang, Beijing (CN); Xiang Gao, Beijing (CN); Hongtao Guan, Beijing (CN); Henning Thoegersen, Farum (DK); Kristian Sass-oerum, Koebenhavn (DK); Lars Fogh Iversen, Holte (DK); Per Noergaard, Humlebaek (DK); Sebastian Beck Joergensen, Virum (DK); Kristian Tage Hansen, Slangerup (DK); Yi Wang, Beijing (CN)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/083,811

(22) Filed: Dec. 19, 2022

(65) Prior Publication Data

US 2023/0212245 A1 Jul. 6, 2023

Related U.S. Application Data

(63) Continuation of application No. 17/194,908, filed on Mar. 8, 2021, now abandoned, which is a continuation of application No. 16/303,516, filed as application No. PCT/EP2017/062583 on May 24, 2017, now abandoned.

(30) Foreign Application Priority Data

May 24, 2016 (WO) ................ PCT/CN2016/083104
Oct. 27, 2016 (WO) ................ PCT/CN2016/103574

(51) Int. Cl.
| | | |
|---|---|---|
| C07K 14/475 | (2006.01) | |
| A61K 38/00 | (2006.01) | |
| A61K 38/27 | (2006.01) | |
| A61P 3/04 | (2006.01) | |

(52) U.S. Cl.
CPC ............ *C07K 14/475* (2013.01); *A61K 38/00* (2013.01); *A61K 38/27* (2013.01); *A61P 3/04* (2018.01); *C07K 2319/31* (2013.01)

(58) Field of Classification Search
None
See application file for complete search history.

(56) References Cited

U.S. PATENT DOCUMENTS

| | | | |
|---|---|---|---|
| 6,624,129 B1 | 9/2003 | Borch et al. | |
| 9,161,966 B2 | 10/2015 | Matern et al. | |
| 9,272,019 B2 | 3/2016 | Shaw et al. | |
| 9,920,118 B2 | 3/2018 | Shen et al. | |
| 10,000,543 B2 | 6/2018 | Schellenberger et al. | |
| 10,323,075 B2 | 6/2019 | Matern et al. | |
| 10,398,782 B2 * | 9/2019 | Gao ....................... | A61K 38/19 |
| 2003/0232385 A1 | 12/2003 | Breit et al. | |
| 2004/0063635 A1 | 4/2004 | Yu et al. | |
| 2009/0004181 A1 | 1/2009 | Breit | |
| 2010/0239554 A1 | 9/2010 | Schellenberger et al. | |
| 2011/0172146 A1 | 7/2011 | Schellenberger et al. | |
| 2016/0030585 A1 | 2/2016 | Barnes et al. | |
| 2016/0129083 A1 | 5/2016 | Shaw et al. | |
| 2018/0339057 A1 | 11/2018 | Gao et al. | |
| 2019/0248852 A1 | 8/2019 | Zhang et al. | |
| 2020/0079829 A1 | 3/2020 | Gao et al. | |
| 2021/0198331 A1 | 7/2021 | Zhang et al. | |

FOREIGN PATENT DOCUMENTS

| | | |
|---|---|---|
| CL | 2017000864 A1 | 5/2018 |
| CN | 1152942 C | 6/2004 |
| CN | 102481331 A | 5/2012 |
| JP | 2003526319 A | 9/2003 |
| JP | 2008506635 A | 3/2008 |
| JP | 2008507292 A | 3/2008 |
| RU | 2015136440 | 10/2019 |
| WO | 0179271 A1 | 10/2001 |
| WO | 0179443 A2 | 10/2001 |
| WO | 2005099746 A1 | 10/2005 |
| WO | 2009023270 A2 | 2/2009 |
| WO | 2010091122 | 8/2009 |
| WO | 2010/084169 A2 | 7/2010 |
| WO | 2011123813 A2 | 10/2011 |
| WO | 12138919 A2 | 10/2012 |
| WO | 2013113008 A1 | 8/2013 |

(Continued)

OTHER PUBLICATIONS

Johnen et al., "Tumor-Induced Anorexia and Weight Loss are Mediated by the TGF-beta Superfamily Cytokine MIC-1," Nat Med, 2007, vol. 13, pp. 1333-1340.
Robinson et al "Structure-dependent nonenzymatic deamidation of glutaminyl and asparaginyl pentapeptides" J. Peptide Res 2004 vol. 63 No. 5 pp. 426-436.
William R Strohl, "Fusion Proteins for Half-Life Extension of Biologics as a Strategy to Make Biobetters," Biodrugs, 2015, vol. 29, No. 4, pp. 215-239.
Arai R. et al., Design of the linkers which effectively separate domains of a bifunctional fusion protein, Protein Engineering, 2001, vol. 14, No. 8, pp. 529-532.

(Continued)

*Primary Examiner* — Christina Bradley
(74) *Attorney, Agent, or Firm* — Leon Y. Lum

(57) ABSTRACT

The invention relates to MIC-1 compounds. More specifically it relates to compounds comprising a MIC-1 polypeptide and an N-terminal amino acid extension, wherein said extension consists of 3 to 36 amino acid residues and where the compound has a calculated pI lower than 6.5. The compounds of the invention have MIC-1 activity. The invention also relates to pharmaceutical compositions comprising such compounds and pharmaceutically acceptable excipients, as well as the medical use of the compounds.

1 Claim, 3 Drawing Sheets

Specification includes a Sequence Listing.

(56) References Cited

FOREIGN PATENT DOCUMENTS

| WO | 2013148117 | A1 | 10/2013 |
|---|---|---|---|
| WO | 2014120619 | A2 | 8/2014 |
| WO | 2015017710 | A1 | 2/2015 |
| WO | 2015027082 | A1 | 2/2015 |
| WO | 2015197446 | A1 | 12/2015 |
| WO | 2015200078 | A1 | 12/2015 |
| WO | 2016018931 | | 2/2016 |
| WO | 2016069925 | A1 | 5/2016 |
| WO | 2016102562 | A1 | 6/2016 |
| WO | 2016149501 | A2 | 9/2016 |
| WO | 2017005765 | A1 | 1/2017 |
| WO | 2017055612 | A1 | 4/2017 |
| WO | 2017055613 | A2 | 4/2017 |
| WO | 2017055614 | A1 | 4/2017 |
| WO | 2017109706 | A1 | 6/2017 |
| WO | 2017196647 | A1 | 11/2017 |
| WO | 2017202936 | A1 | 11/2017 |
| WO | 2018215525 | A1 | 11/2018 |

OTHER PUBLICATIONS

Bauskin A. R. et al., The propeptide of macrophage inhibitory cytokine (MIC-1), a TGF-beta superfamily member, acts as a quality control determinant for correctly folded MIC-1, The EMBO Journal, 2000, vol. 19, No. 10, pp. 2212-2220.

Chen X. et al., Fusion protein linkers: property, design and functionality, Advanced Drug Delivery Reviews, 2012, vol. 65, No. 10, pp. 1357-1369.

Lu Z. et al., Change of body weight and macrophage inhibitory cytokine-1 during chemotherapy in advanced gastric cancer: what is their clinical significance?, Public Library of Science One, 2014, vol. 9, No. 2, p. e88553.

Bootcov et al., "MIC-1, a Novel Macrophage Inhibitory Cytokine, is a Divergent Member of the TGF-? Superfamily," Proc. Natl. Acad. Sci. USA, Oct. 1997, vol. 94, pp. 11514-11519.

Johnen et al, "Tumor-Induced Anorexia and Weight Loss are Mediated by the TGF-? Superfamily Cytokine MIC-1," Nature Medicine, Nov. 2007, vol. 13, No. 11, pp. 1333-1340.

Macia et al, "Macrophage Inhibitory Cytokine 1 (MIC-1/GDF15) Decreases Food Intake, Body Weight and Improves Glucose Tolerance in Mice on Normal & Obesogenic Data," PLoS One, Apr. 2012, vol. 7, No. 4, e34868.

Yun Ho Kim et al., "Comparing the Effect on Protein Stability of Methionine Oxidation Versus Mutagenesis: Steps Toward Engineering Oxidative Resistance in Proteins and the Possibility of Oxidation During Processing or Storage," Protein Engineering, 2001, vol. 14, pp. 343-347.

Marqusee et al., "Unusually stable helix formation in short alanine-based peptides," Proceedings of the National Academy of Sciences of the United States of America, 1989, vol. 86, pp. 5286-5290.

Tsai et al., "TGF-b Superfamily Cytokine MIC-1/GDF15 Is a Physiological Appetite and Body Weight Regulator," PLOS ONE, Feb. 28, 2013, vol. 8, e55174, pp. 1-10.

Yeh et al., "Design of yeast-secreted albumin derviatives for human therapy: Biological and avtiviral properties of a serum albumin-CD4 genetic conjugate," Proceedings of the National Academy of Sciences of the United States of America, Mar. 1992, vol. 89, pp. 1904-1908.

Schellenberger et al. "A recombinant polypeptide extends the in vivo half-life of peptides and proteins in a tunable manner." Nature biotechnology, Nov. 2009, vol. 27, No. 12, pp. 1186-1190.

Arnau et al., "Current strategies for the use of affinity tags and tag removal for the purification of recombinant proteins", Protein expression and purification, Jul. 2006, vol. 48, No. 1, pp. 1-13.

Bhopale G. M., "Pathogenesis of toxoplasmosis", Comparative immunology, microbiology and infectious diseases, Jul. 2003, vol. 26, No. 4, p. 213-222, p. 215.

Fairlie et al., "Epitope mapping of the transforming growth factor-? superfamily protein, macrophage inhibitory cytokine-1 (MIC-1): identification of at least five distinct epitope specificities", Biochemistry, Jan. 2001, vol. 40, No. 1, p. 65-73, p. 65.

Frankel et al., "Characterization of diphtheria fusion proteins targeted to the human interleukin-3 receptor", Protein Eng., Aug. 2000, vol. 13, No. 8, p. 575-581.

Goncharova et al., "The role of the growth and differentiation factor gdf-15 in physiological and pathological processes in human ontogenesis", Valeologiya, 2013, No. 2, pp. 14-20.

Kontermann et al. "Bispecific antibodies." Drug discovery today, Jul. 2015, vol. 20, No. 7, pp. 838-847.

Muller et al., "Spliceosomal peptide P140 for immunotherapy of systemic lupus erythematosus: results of an early phase II clinical trial", Arthritis & Rheumatism: Official Journal of the American College of Rheumatology, Dec. 2008, vol. 58, No. 12, pp. 3873-3883, p. 3874.

Orlando et al., "Modification of proteins and low molecular weight substances with hydroxyethyl starch (HES)", Inauguraldissertation, Giesen, Jan. 2003, p. 166, p. 15.

Expasy ProtParam Tool downloaded on Jul. 28, 2022, https://web.expasy.org/protparam/.

Miosge et al., "Comparison of predicted and actual consequences of missense mutations", PNAS, Sep. 2015, vol. 112, No. 37, pp. E5189-E5198.

Bork, "Powers and Pitfalls in Sequence Analysis: The 70% Hurdle," Genome Research, 2000, vol. 10, pp. 398-400.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., Nov. 1990, vol. 111, pp. 2129-2138.

Skolnick J et al. "From genes to protein structure and function: novel applications of computational approaches in the genomic era" Trends in Biotech, 2000, vol. 18, No. 1, pp. 34-39.

* cited by examiner

SEQUENCE LISTING

```
Sequence total quantity: 222
SEQ ID NO: 1           moltype = AA  length = 112
FEATURE                Location/Qualifiers
source                 1..112
                       mol_type = protein
                       organism = Homo sapiens
SEQUENCE: 1
ARNGDHCPLG PGRCCRLHTV RASLEDLGWA DWVLSPREVQ VTMCIGACPS QFRAANMHAQ   60
IKTSLHRLKP DTVPAPCCVP ASYNPMVLIQ KTDTGVSLQT YDDLLAKDCH CI          112

SEQ ID NO: 2           moltype = AA  length = 111
FEATURE                Location/Qualifiers
REGION                 1..111
                       note = MIC-1 des-N3
source                 1..111
                       mol_type = protein
                       organism = synthetic construct
SEQUENCE: 2
ARGDHCPLGP GRCCRLHTVR ASLEDLGWAD WVLSPREVQV TMCIGACPSQ FRAANMHAQI   60
KTSLHRLKPD TVPAPCCVPA SYNPMVLIQK TDTGVSLQTY DDLLAKDCHC I            111

SEQ ID NO: 3           moltype = AA  length = 109
FEATURE                Location/Qualifiers
REGION                 1..109
                       note = MIC-1-Del (1-3)
source                 1..109
                       mol_type = protein
                       organism = synthetic construct
SEQUENCE: 3
GDHCPLGPGR CCRLHTVRAS LEDLGWADWV LSPREVQVTM CIGACPSQFR AANMHAQIKT   60
SLHRLKPDTV PAPCCVPASY NPMVLIQKTD TGVSLQTYDD LLAKDCHCI              109

SEQ ID NO: 4           moltype = AA  length = 6
FEATURE                Location/Qualifiers
REGION                 1..6
                       note = N-terminal extension
source                 1..6
                       mol_type = protein
                       organism = synthetic construct
SEQUENCE: 4
SPAGSP                                                              6

SEQ ID NO: 5           moltype = AA  length = 6
FEATURE                Location/Qualifiers
REGION                 1..6
                       note = N-terminal extension
source                 1..6
                       mol_type = protein
                       organism = synthetic construct
SEQUENCE: 5
TSESAT                                                              6

SEQ ID NO: 6           moltype = AA  length = 6
FEATURE                Location/Qualifiers
REGION                 1..6
                       note = N-terminal extension
source                 1..6
```

```
                         mol_type = protein
                         organism = synthetic construct
SEQUENCE: 6
TSTEPE                                                                      6

SEQ ID NO: 7             moltype = AA   length = 6
FEATURE                  Location/Qualifiers
REGION                   1..6
                         note = N-terminal extension
source                   1..6
                         mol_type = protein
                         organism = synthetic construct
SEQUENCE: 7
SEPATS                                                                      6

SEQ ID NO: 8             moltype = AA   length = 6
FEATURE                  Location/Qualifiers
REGION                   1..6
                         note = N-terminal extension
source                   1..6
                         mol_type = protein
                         organism = synthetic construct
SEQUENCE: 8
TSTEEG                                                                      6

SEQ ID NO: 9             moltype = AA   length = 6
FEATURE                  Location/Qualifiers
REGION                   1..6
                         note = N-terminal extension
source                   1..6
                         mol_type = protein
                         organism = synthetic construct
SEQUENCE: 9
PESGPG                                                                      6

SEQ ID NO: 10            moltype = AA   length = 6
FEATURE                  Location/Qualifiers
REGION                   1..6
                         note = N-terminal extension
source                   1..6
                         mol_type = protein
                         organism = synthetic construct
SEQUENCE: 10
SGSAPG                                                                      6

SEQ ID NO: 11            moltype = AA   length = 6
FEATURE                  Location/Qualifiers
REGION                   1..6
                         note = N-terminal extension
source                   1..6
                         mol_type = protein
                         organism = synthetic construct
SEQUENCE: 11
GSETPG                                                                      6

SEQ ID NO: 12            moltype = AA   length = 24
FEATURE                  Location/Qualifiers
REGION                   1..24
                         note = N-terminal extension
source                   1..24
                         mol_type = protein
                         organism = synthetic construct
SEQUENCE: 12
SEPATSGSET PGSPAGSPTS TEEG                                                  24

SEQ ID NO: 13            moltype = AA   length = 24
FEATURE                  Location/Qualifiers
REGION                   1..24
                         note = N-terminal extension
source                   1..24
                         mol_type = protein
                         organism = synthetic construct
SEQUENCE: 13
SEPATSGSET PGTSESATPE SGPG                                                  24

SEQ ID NO: 14            moltype = AA   length = 24
FEATURE                  Location/Qualifiers
REGION                   1..24
                         note = N-terminal extension
```

```
source                      1..24
                            mol_type = protein
                            organism = synthetic construct
SEQUENCE: 14
SEPATSGSET PGTSTEPESG SAPG                                            24

SEQ ID NO: 15               moltype = AA  length = 30
FEATURE                     Location/Qualifiers
REGION                      1..30
                            note = N-terminal extension
source                      1..30
                            mol_type = protein
                            organism = synthetic construct
SEQUENCE: 15
SEPATSGSET PGSPAGSPTS TEEGSPAGSP                                      30

SEQ ID NO: 16               moltype = AA  length = 30
FEATURE                     Location/Qualifiers
REGION                      1..30
                            note = N-terminal extension
source                      1..30
                            mol_type = protein
                            organism = synthetic construct
SEQUENCE: 16
SEPATSGSET PGTSESATPE SGPGSPAGSP                                      30

SEQ ID NO: 17               moltype = AA  length = 30
FEATURE                     Location/Qualifiers
REGION                      1..30
                            note = N-terminal extension
source                      1..30
                            mol_type = protein
                            organism = synthetic construct
SEQUENCE: 17
SEPATSGSET PGTSTEPESG SAPGSPAGSP                                      30

SEQ ID NO: 18               moltype = AA  length = 30
FEATURE                     Location/Qualifiers
REGION                      1..30
                            note = N-terminal extension
source                      1..30
                            mol_type = protein
                            organism = synthetic construct
SEQUENCE: 18
SEPATSGSET PGSPAGSPTS TEEGTSESAT                                      30

SEQ ID NO: 19               moltype = AA  length = 30
FEATURE                     Location/Qualifiers
REGION                      1..30
                            note = N-terminal extension
source                      1..30
                            mol_type = protein
                            organism = synthetic construct
SEQUENCE: 19
SEPATSGSET PGTSESATPE SGPGTSESAT                                      30

SEQ ID NO: 20               moltype = AA  length = 30
FEATURE                     Location/Qualifiers
REGION                      1..30
                            note = N-terminal extension
source                      1..30
                            mol_type = protein
                            organism = synthetic construct
SEQUENCE: 20
SEPATSGSET PGTSTEPESG SAPGTSESAT                                      30

SEQ ID NO: 21               moltype = AA  length = 30
FEATURE                     Location/Qualifiers
REGION                      1..30
                            note = N-terminal extension
source                      1..30
                            mol_type = protein
                            organism = synthetic construct
SEQUENCE: 21
SEPATSGSET PGSPAGSPTS TEEGTSTEPE                                      30

SEQ ID NO: 22               moltype = AA  length = 30
FEATURE                     Location/Qualifiers
REGION                      1..30
```

```
                    note = N-terminal extension
source              1..30
                    mol_type = protein
                    organism = synthetic construct
SEQUENCE: 22
SEPATSGSET PGTSESATPE SGPGTSTEPE                                       30

SEQ ID NO: 23       moltype = AA  length = 30
FEATURE             Location/Qualifiers
REGION              1..30
                    note = N-terminal extension
source              1..30
                    mol_type = protein
                    organism = synthetic construct
SEQUENCE: 23
SEPATSGSET PGTSTEPESG SAPGTSTEPE                                       30

SEQ ID NO: 24       moltype = AA  length = 30
FEATURE             Location/Qualifiers
REGION              1..30
                    note = N-terminal extension
source              1..30
                    mol_type = protein
                    organism = synthetic construct
SEQUENCE: 24
SEPATSGSET PGSPAGSPTS TEEGSEPATS                                       30

SEQ ID NO: 25       moltype = AA  length = 30
FEATURE             Location/Qualifiers
REGION              1..30
                    note = N-terminal extension
source              1..30
                    mol_type = protein
                    organism = synthetic construct
SEQUENCE: 25
SEPATSGSET PGTSESATPE SGPGSEPATS                                       30

SEQ ID NO: 26       moltype = AA  length = 30
FEATURE             Location/Qualifiers
REGION              1..30
                    note = N-terminal extension
source              1..30
                    mol_type = protein
                    organism = synthetic construct
SEQUENCE: 26
SEPATSGSET PGTSTEPESG SAPGSEPATS                                       30

SEQ ID NO: 27       moltype = AA  length = 30
FEATURE             Location/Qualifiers
REGION              1..30
                    note = N-terminal extension
source              1..30
                    mol_type = protein
                    organism = synthetic construct
SEQUENCE: 27
SEPATSGSET PGSPAGSPTS TEEGTSTEEG                                       30

SEQ ID NO: 28       moltype = AA  length = 30
FEATURE             Location/Qualifiers
REGION              1..30
                    note = N-terminal extension
source              1..30
                    mol_type = protein
                    organism = synthetic construct
SEQUENCE: 28
SEPATSGSET PGTSESATPE SGPGTSTEEG                                       30

SEQ ID NO: 29       moltype = AA  length = 30
FEATURE             Location/Qualifiers
REGION              1..30
                    note = N-terminal extension
source              1..30
                    mol_type = protein
                    organism = synthetic construct
SEQUENCE: 29
SEPATSGSET PGTSTEPESG SAPGTSTEEG                                       30

SEQ ID NO: 30       moltype = AA  length = 30
FEATURE             Location/Qualifiers
```

```
REGION                          1..30
                                note = N-terminal extension
source                          1..30
                                mol_type = protein
                                organism = synthetic construct
SEQUENCE: 30
SEPATSGSET PGSPAGSPTS TEEGPESGPG                                        30

SEQ ID NO: 31                   moltype = AA  length = 30
FEATURE                         Location/Qualifiers
REGION                          1..30
                                note = N-terminal extension
source                          1..30
                                mol_type = protein
                                organism = synthetic construct
SEQUENCE: 31
SEPATSGSET PGTSESATPE SGPGPESGPG                                        30

SEQ ID NO: 32                   moltype = AA  length = 30
FEATURE                         Location/Qualifiers
REGION                          1..30
                                note = N-terminal extension
source                          1..30
                                mol_type = protein
                                organism = synthetic construct
SEQUENCE: 32
SEPATSGSET PGTSTEPESG SAPGPESGPG                                        30

SEQ ID NO: 33                   moltype = AA  length = 30
FEATURE                         Location/Qualifiers
REGION                          1..30
                                note = N-terminal extension
source                          1..30
                                mol_type = protein
                                organism = synthetic construct
SEQUENCE: 33
SEPATSGSET PGSPAGSPTS TEEGSGSAPG                                        30

SEQ ID NO: 34                   moltype = AA  length = 30
FEATURE                         Location/Qualifiers
REGION                          1..30
                                note = N-terminal extension
source                          1..30
                                mol_type = protein
                                organism = synthetic construct
SEQUENCE: 34
SEPATSGSET PGTSESATPE SGPGSGSAPG                                        30

SEQ ID NO: 35                   moltype = AA  length = 30
FEATURE                         Location/Qualifiers
REGION                          1..30
                                note = N-terminal extension
source                          1..30
                                mol_type = protein
                                organism = synthetic construct
SEQUENCE: 35
SEPATSGSET PGTSTEPESG SAPGSGSAPG                                        30

SEQ ID NO: 36                   moltype = AA  length = 30
FEATURE                         Location/Qualifiers
REGION                          1..30
                                note = N-terminal extension
source                          1..30
                                mol_type = protein
                                organism = synthetic construct
SEQUENCE: 36
SEPATSGSET PGSPAGSPTS TEEGGSETPG                                        30

SEQ ID NO: 37                   moltype = AA  length = 30
FEATURE                         Location/Qualifiers
REGION                          1..30
                                note = N-terminal extension
source                          1..30
                                mol_type = protein
                                organism = synthetic construct
SEQUENCE: 37
SEPATSGSET PGTSESATPE SGPGGSETPG                                        30

SEQ ID NO: 38                   moltype = AA  length = 30
```

```
FEATURE              Location/Qualifiers
REGION               1..30
                     note = N-terminal extension
source               1..30
                     mol_type = protein
                     organism = synthetic construct
SEQUENCE: 38
SEPATSGSET PGTSTEPESG SAPGGSETPG                                  30

SEQ ID NO: 39        moltype = AA  length = 36
FEATURE              Location/Qualifiers
REGION               1..36
                     note = N-terminal extension
source               1..36
                     mol_type = protein
                     organism = synthetic construct
SEQUENCE: 39
SEPATSGSET PGSPAGSPTS TEEGTSESAT PESGPG                           36

SEQ ID NO: 40        moltype = AA  length = 36
FEATURE              Location/Qualifiers
REGION               1..36
                     note = N-terminal extension
source               1..36
                     mol_type = protein
                     organism = synthetic construct
SEQUENCE: 40
SEPATSGSET PGSPAGSPTS TEEGSPAGSP TSTEEG                           36

SEQ ID NO: 41        moltype = AA  length = 36
FEATURE              Location/Qualifiers
REGION               1..36
                     note = N-terminal extension
source               1..36
                     mol_type = protein
                     organism = synthetic construct
SEQUENCE: 41
SEPATSGSET PGSPAGSPTS TEEGTSTEPE SGSAPG                           36

SEQ ID NO: 42        moltype = AA  length = 36
FEATURE              Location/Qualifiers
REGION               1..36
                     note = N-terminal extension
source               1..36
                     mol_type = protein
                     organism = synthetic construct
SEQUENCE: 42
SEPATSGSET PGTSESATPE SGPGSPAGSP TSTEEG                           36

SEQ ID NO: 43        moltype = AA  length = 36
FEATURE              Location/Qualifiers
REGION               1..36
                     note = N-terminal extension
source               1..36
                     mol_type = protein
                     organism = synthetic construct
SEQUENCE: 43
SEPATSGSET PGTSESATPE SGPGTSESAT PESGPG                           36

SEQ ID NO: 44        moltype = AA  length = 36
FEATURE              Location/Qualifiers
REGION               1..36
                     note = N-terminal extension
source               1..36
                     mol_type = protein
                     organism = synthetic construct
SEQUENCE: 44
SEPATSGSET PGTSESATPE SGPGTSTEPE SGSAPG                           36

SEQ ID NO: 45        moltype = AA  length = 36
FEATURE              Location/Qualifiers
REGION               1..36
                     note = N-terminal extension
source               1..36
                     mol_type = protein
                     organism = synthetic construct
SEQUENCE: 45
SEPATSGSET PGTSESATPE SGPGSEPATS GSETPG                           36
```

```
SEQ ID NO: 46           moltype = AA  length = 36
FEATURE                 Location/Qualifiers
REGION                  1..36
                        note = N-terminal extension
source                  1..36
                        mol_type = protein
                        organism = synthetic construct
SEQUENCE: 46
SEPATSGSET PGTSTEPESG SAPGSPAGSP TSTEEG                                    36

SEQ ID NO: 47           moltype = AA  length = 36
FEATURE                 Location/Qualifiers
REGION                  1..36
                        note = N-terminal extension
source                  1..36
                        mol_type = protein
                        organism = synthetic construct
SEQUENCE: 47
SEPATSGSET PGTSTEPESG SAPGTSESAT PESGPG                                    36

SEQ ID NO: 48           moltype = AA  length = 36
FEATURE                 Location/Qualifiers
REGION                  1..36
                        note = N-terminal extension
source                  1..36
                        mol_type = protein
                        organism = synthetic construct
SEQUENCE: 48
SEPATSGSET PGTSTEPESG SAPGTSTEPE SGSAPG                                    36

SEQ ID NO: 49           moltype = AA  length = 36
FEATURE                 Location/Qualifiers
REGION                  1..36
                        note = N-terminal extension
source                  1..36
                        mol_type = protein
                        organism = synthetic construct
SEQUENCE: 49
SEPATSGSET PGTSTEPESG SAPGSEPATS GSETPG                                    36

SEQ ID NO: 50           moltype = AA  length = 36
FEATURE                 Location/Qualifiers
REGION                  1..36
                        note = N-terminal extension
source                  1..36
                        mol_type = protein
                        organism = synthetic construct
SEQUENCE: 50
SEPATSGSET PGSEPATSGS ETPGSPAGSP TSTEEG                                    36

SEQ ID NO: 51           moltype = AA  length = 36
FEATURE                 Location/Qualifiers
REGION                  1..36
                        note = N-terminal extension
source                  1..36
                        mol_type = protein
                        organism = synthetic construct
SEQUENCE: 51
SEPATSGSET PGSEPATSGS ETPGTSESAT PESGPG                                    36

SEQ ID NO: 52           moltype = AA  length = 36
FEATURE                 Location/Qualifiers
REGION                  1..36
                        note = N-terminal extension
source                  1..36
                        mol_type = protein
                        organism = synthetic construct
SEQUENCE: 52
SEPATSGSET PGSEPATSGS ETPGTSTEPE SGSAPG                                    36

SEQ ID NO: 53           moltype = AA  length = 36
FEATURE                 Location/Qualifiers
REGION                  1..36
                        note = N-terminal extension
source                  1..36
                        mol_type = protein
                        organism = synthetic construct
SEQUENCE: 53
SEPATSGSET PGSEPATSGS ETPGSEPATS GSETPG                                    36
```

```
SEQ ID NO: 54              moltype = AA   length = 6
FEATURE                    Location/Qualifiers
REGION                     1..6
                           note = N-terminal extension
source                     1..6
                           mol_type = protein
                           organism = synthetic construct
SEQUENCE: 54
AEEAES                                                                    6

SEQ ID NO: 55              moltype = AA   length = 4
FEATURE                    Location/Qualifiers
REGION                     1..4
                           note = N-terminal extension
source                     1..4
                           mol_type = protein
                           organism = synthetic construct
SEQUENCE: 55
AESM                                                                      4

SEQ ID NO: 56              moltype = AA   length = 9
FEATURE                    Location/Qualifiers
REGION                     1..9
                           note = N-terminal extension
source                     1..9
                           mol_type = protein
                           organism = synthetic construct
SEQUENCE: 56
AEEAEEAES                                                                 9

SEQ ID NO: 57              moltype = AA   length = 20
FEATURE                    Location/Qualifiers
REGION                     1..20
                           note = N-terminal extension
source                     1..20
                           mol_type = protein
                           organism = synthetic construct
SEQUENCE: 57
GEPSGEPSGE PSGEPSGEPS                                                    20

SEQ ID NO: 58              moltype = AA   length = 24
FEATURE                    Location/Qualifiers
REGION                     1..24
                           note = N-terminal extension
source                     1..24
                           mol_type = protein
                           organism = synthetic construct
SEQUENCE: 58
SPAGSPTSTE EGTSESATPE SGPG                                               24

SEQ ID NO: 59              moltype = AA   length = 21
FEATURE                    Location/Qualifiers
REGION                     1..21
                           note = N-terminal extension
source                     1..21
                           mol_type = protein
                           organism = synthetic construct
SEQUENCE: 59
AEEAEEAEEA EEAEEAEEAE S                                                  21

SEQ ID NO: 60              moltype = AA   length = 18
FEATURE                    Location/Qualifiers
REGION                     1..18
                           note = N-terminal extension
source                     1..18
                           mol_type = protein
                           organism = synthetic construct
SEQUENCE: 60
AEEAEEAEEA EEAEEAES                                                      18

SEQ ID NO: 61              moltype = AA   length = 12
FEATURE                    Location/Qualifiers
REGION                     1..12
                           note = N-terminal extension
source                     1..12
                           mol_type = protein
                           organism = synthetic construct
SEQUENCE: 61
```

```
AEEAEEAEEA ES                                                          12

SEQ ID NO: 62           moltype = AA  length = 26
FEATURE                 Location/Qualifiers
REGION                  1..26
                        note = N-terminal extension
source                  1..26
                        mol_type = protein
                        organism = synthetic construct
SEQUENCE: 62
AASPAGSPTS TEEGTSESAT PESGPG                                           26

SEQ ID NO: 63           moltype = AA  length = 24
FEATURE                 Location/Qualifiers
REGION                  1..24
                        note = N-terminal extension
source                  1..24
                        mol_type = protein
                        organism = synthetic construct
SEQUENCE: 63
TSESATPESG PGTSESATPE SGPG                                             24

SEQ ID NO: 64           moltype = AA  length = 26
FEATURE                 Location/Qualifiers
REGION                  1..26
                        note = N-terminal extension
source                  1..26
                        mol_type = protein
                        organism = synthetic construct
SEQUENCE: 64
AASPAGSPTS TEEGTSESAT PESGPG                                           26

SEQ ID NO: 65           moltype = AA  length = 22
FEATURE                 Location/Qualifiers
REGION                  1..22
                        note = N-terminal extension
source                  1..22
                        mol_type = protein
                        organism = synthetic construct
SEQUENCE: 65
AAPEDEETPE QEGSGSGSGS GS                                               22

SEQ ID NO: 66           moltype = AA  length = 12
FEATURE                 Location/Qualifiers
REGION                  1..12
                        note = N-terminal extension
source                  1..12
                        mol_type = protein
                        organism = synthetic construct
SEQUENCE: 66
AAPEDEETPE QE                                                          12

SEQ ID NO: 67           moltype = AA  length = 22
FEATURE                 Location/Qualifiers
REGION                  1..22
                        note = N-terminal extension
source                  1..22
                        mol_type = protein
                        organism = synthetic construct
SEQUENCE: 67
AAPDEGTEEE TEGSGSGSGS GS                                               22

SEQ ID NO: 68           moltype = AA  length = 24
FEATURE                 Location/Qualifiers
REGION                  1..24
                        note = N-terminal extension
source                  1..24
                        mol_type = protein
                        organism = synthetic construct
SEQUENCE: 68
SEPATSGSET PGSEPATSGS ETPG                                             24

SEQ ID NO: 69           moltype = AA  length = 25
FEATURE                 Location/Qualifiers
REGION                  1..25
                        note = N-terminal extension
source                  1..25
                        mol_type = protein
                        organism = synthetic construct
```

-continued

```
SEQUENCE: 69
AGPEQGQEPG PEQGQEPGPE QGQEP                                          25

SEQ ID NO: 70           moltype = AA  length = 30
FEATURE                 Location/Qualifiers
REGION                  1..30
                        note = N-terminal extension
source                  1..30
                        mol_type = protein
                        organism = synthetic construct
SEQUENCE: 70
SEPATSGSET PGTSESATPE SGPGTSTEPS                                     30

SEQ ID NO: 71           moltype = AA  length = 32
FEATURE                 Location/Qualifiers
REGION                  1..32
                        note = N-terminal extension
source                  1..32
                        mol_type = protein
                        organism = synthetic construct
SEQUENCE: 71
SEPATSGSET PGTSESATPE SGPGTSTEPS EG                                  32

SEQ ID NO: 72           moltype = AA  length = 24
FEATURE                 Location/Qualifiers
REGION                  1..24
                        note = N-terminal extension
source                  1..24
                        mol_type = protein
                        organism = synthetic construct
SEQUENCE: 72
GEPSGEPSGE PSGEPSGEPS GEPS                                           24

SEQ ID NO: 73           moltype = AA  length = 112
FEATURE                 Location/Qualifiers
REGION                  1..112
                        note = MIC-1 polypeptide
source                  1..112
                        mol_type = protein
                        organism = synthetic construct
SEQUENCE: 73
AAEGDHCPLG PGRCCRLHTV RASLEDLGWA DWVLSPREVQ VTMCIGACPS QFRAANMHAQ    60
IKTSLHRLKP DTVPAPCCVP ASYNPMVLIQ KTDTGVSLQT YDDLLAKDCH CI           112

SEQ ID NO: 74           moltype = AA  length = 112
FEATURE                 Location/Qualifiers
REGION                  1..112
                        note = MIC-1 polypeptide
source                  1..112
                        mol_type = protein
                        organism = synthetic construct
SEQUENCE: 74
AAEGDHCPLG PGRCCRLHTV RASLEDLGWA DWVLSPREVQ VTMCIGACPS QFREANMHAQ    60
IKTSLHRLKP DTVPAPCCVP ASYNPMVLIQ KTDTGVSLQT YDDLLAKDCH CI           112

SEQ ID NO: 75           moltype = AA  length = 112
FEATURE                 Location/Qualifiers
REGION                  1..112
                        note = MIC-1 polypeptide
source                  1..112
                        mol_type = protein
                        organism = synthetic construct
SEQUENCE: 75
AAEGDHCPLG PGRCCRLHTV RASLEDLGWA DWVLSPREVQ VTMCIGACPS QFRAANMHAQ    60
IKTSLHRLKP DTVPAPCCVP ESYNPMVLIQ KTDTGVSLQT YDDLLAKDCH CI           112

SEQ ID NO: 76           moltype = AA  length = 112
FEATURE                 Location/Qualifiers
REGION                  1..112
                        note = MIC-1 polypeptide
source                  1..112
                        mol_type = protein
                        organism = synthetic construct
SEQUENCE: 76
AAEGDHCPLG PGRCCRLETV RASLEDLGWA DWVLSPREVQ VTMCIGACPS QFRAANMHAQ    60
IKTSLHRLKP DTVPAPCCVP ASYNPMVLIQ KTDTGVSLQT YDDLLAKDCH CI           112

SEQ ID NO: 77           moltype = AA  length = 112
FEATURE                 Location/Qualifiers
```

```
REGION                    1..112
                          note = MIC-1 polypeptide
source                    1..112
                          mol_type = protein
                          organism = synthetic construct
SEQUENCE: 77
AAEGDHCPLG PGRCCRLHTV RASLEDLGWA DWVLSPREVQ VTMCIGACPS QFRAANMHAQ    60
IKTSLHRLEP DTVPAPCCVP ASYNPMVLIQ KTDTGVSLQT YDDLLAKDCH CI           112

SEQ ID NO: 78             moltype = AA  length = 112
FEATURE                   Location/Qualifiers
REGION                    1..112
                          note = MIC-1 polypeptide
source                    1..112
                          mol_type = protein
                          organism = synthetic construct
SEQUENCE: 78
AAEGDHCPLG PGRCCRLHTV RASLEDLGWA DWVLSPREVQ VTMCIGACPS QFRAANMHAQ    60
IKTSLHRLKP DTVPAPCCVP ASYNPMVLIQ KTDTGVSLQT YDDLLAEDCH CI           112

SEQ ID NO: 79             moltype = AA  length = 112
FEATURE                   Location/Qualifiers
REGION                    1..112
                          note = MIC-1 polypeptide
source                    1..112
                          mol_type = protein
                          organism = synthetic construct
SEQUENCE: 79
AAEGDHCPLG PGRCCRLHTV RASLEDLGWA DWVLSPREVQ VTMCIGACPS QFRAANMHAQ    60
IKTSLHREKP DTVPAPCCVP ASYNPMVLIQ KTDTGVSLQT YDDLLAKDCH CI           112

SEQ ID NO: 80             moltype = AA  length = 112
FEATURE                   Location/Qualifiers
REGION                    1..112
                          note = MIC-1 polypeptide
source                    1..112
                          mol_type = protein
                          organism = synthetic construct
SEQUENCE: 80
AAEGDHCPLG PGRCCRLHTV RASLEDLGWA DWVLSPREVQ VTMCIGECPS QFRAANMHAQ    60
IKTSLHRLKP DTVPAPCCVP ASYNPMVLIQ KTDTGVSLQT YDDLLAKDCH CI           112

SEQ ID NO: 81             moltype = AA  length = 112
FEATURE                   Location/Qualifiers
REGION                    1..112
                          note = MIC-1 polypeptide
source                    1..112
                          mol_type = protein
                          organism = synthetic construct
SEQUENCE: 81
AAEGDHCPLG PGRCCRLHTV RASLEDLGWA DWVLSPREVQ VTMCIGACPS QFRAANMHAQ    60
IKTSLHRLKP DTVPAPCCVP ASYNPMVLIQ KTDTGVSLQT YDDLEAKDCH CI           112

SEQ ID NO: 82             moltype = AA  length = 112
FEATURE                   Location/Qualifiers
REGION                    1..112
                          note = MIC-1 polypeptide
source                    1..112
                          mol_type = protein
                          organism = synthetic construct
SEQUENCE: 82
AAEGDHCPLG PGRCCRLHTV RASLEDLGWA DWVLSPREVQ VTMCIGACPS QFRAANEHAQ    60
IKTSLHRLKP DTVPAPCCVP ASYNPMVLIQ KTDTGVSLQT YDDLLAKDCH CI           112

SEQ ID NO: 83             moltype = AA  length = 112
FEATURE                   Location/Qualifiers
REGION                    1..112
                          note = MIC-1 polypeptide
source                    1..112
                          mol_type = protein
                          organism = synthetic construct
SEQUENCE: 83
AAEGDHCPLG PGRCCRLHTV RASLEDLGWA DWVLSPREVQ VTMCIGACPS QFRAANMHAQ    60
IKTSLHRLKP DTVPAPCCVP ASYNEMVLIQ KTDTGVSLQT YDDLLAKDCH CI           112

SEQ ID NO: 84             moltype = AA  length = 112
FEATURE                   Location/Qualifiers
REGION                    1..112
                          note = MIC-1 polypeptide
```

```
                          1..112
                          mol_type = protein
                          organism = synthetic construct
SEQUENCE: 84
AAEGDHCPLG EGRCCRLHTV RASLEDLGWA DWVLSPREVQ VTMCIGACPS QFRAANMHAQ    60
IKTSLHRLKP DTVPAPCCVP ASYNPMVLIQ KTDTGVSLQT YDDLLAKDCH CI           112

SEQ ID NO: 85             moltype = AA  length = 112
FEATURE                   Location/Qualifiers
REGION                    1..112
                          note = MIC-1 polypeptide
source                    1..112
                          mol_type = protein
                          organism = synthetic construct
SEQUENCE: 85
AAEGDHCPLG PGRCCRLHTV EASLEDLGWA DWVLSPREVQ VTMCIGACPS QFRAANMHAQ    60
IKTSLHRLKP DTVPAPCCVP ASYNPMVLIQ KTDTGVSLQT YDDLLAKDCH CI           112

SEQ ID NO: 86             moltype = AA  length = 112
FEATURE                   Location/Qualifiers
REGION                    1..112
                          note = MIC-1 polypeptide
source                    1..112
                          mol_type = protein
                          organism = synthetic construct
SEQUENCE: 86
AAEGDHCPLG PGRCCRLHTV RASLEDLGWA DWVLSPREVQ VTMCIGACPS QFEAANMHAQ    60
IKTSLHRLKP DTVPAPCCVP ASYNPMVLIQ KTDTGVSLQT YDDLLAKDCH CI           112

SEQ ID NO: 87             moltype = AA  length = 112
FEATURE                   Location/Qualifiers
REGION                    1..112
                          note = MIC-1 polypeptide
source                    1..112
                          mol_type = protein
                          organism = synthetic construct
SEQUENCE: 87
AAEGDHCPLG PGRCCRLHTV RASLEDLGWA DWVLSPREVQ VTMCIGACPS QFRAANMHAQ    60
IKTSLHELKP DTVPAPCCVP ASYNPMVLIQ KTDTGVSLQT YDDLLAKDCH CI           112

SEQ ID NO: 88             moltype = AA  length = 112
FEATURE                   Location/Qualifiers
REGION                    1..112
                          note = MIC-1 polypeptide
source                    1..112
                          mol_type = protein
                          organism = synthetic construct
SEQUENCE: 88
AAEGDHCPLG PGRCCRLHTV RASLEDLGWE DWVLSPREVQ VTMCIGACPS QFRAANMHAQ    60
IKTSLHRLKP DTVPAPCCVP ASYNPMVLIQ KTDTGVSLQT YDDLLAKDCH CI           112

SEQ ID NO: 89             moltype = AA  length = 115
FEATURE                   Location/Qualifiers
REGION                    1..115
                          note = MIC-1 polypeptide plus N-terminal extension
source                    1..115
                          mol_type = protein
                          organism = synthetic construct
SEQUENCE: 89
AEEEAESGDHC PLGPGRCCRL HTVRASLEDL GWADWVLSPR EVQVTMCIGA CPSQFRAANM    60
HAQIKTSLHR LKPDTVPAPC CVPASYNPMV LIQKTDTGVS LQTYDDLLAK DCHCI        115

SEQ ID NO: 90             moltype = AA  length = 112
FEATURE                   Location/Qualifiers
REGION                    1..112
                          note = MIC-1 polypeptide plus N-terminal extension
source                    1..112
                          mol_type = protein
                          organism = synthetic construct
SEQUENCE: 90
AESGDHCPLG PGRCCRLHTV RASLEDLGWA DWVLSPREVQ VTMCIGACPS QFRAANMHAQ    60
IKTSLHRLKP DTVPAPCCVP ASYNPMVLIQ KTDTGVSLQT YDDLLAKDCH CI           112

SEQ ID NO: 91             moltype = AA  length = 118
FEATURE                   Location/Qualifiers
REGION                    1..118
                          note = MIC-1 polypeptide plus N-terminal extension
source                    1..118
                          mol_type = protein
```

```
                          organism = synthetic construct
SEQUENCE: 91
AEEAEEEAESG DHCPLGPGRC CRLHTVRASL EDLGWADWVL SPREVQVTMC IGACPSQFRA       60
ANMHAQIKTS LHRLKPDTVP APCCVPASYN PMVLIQKTDT GVSLQTYDDL LAKDCHCI         118

SEQ ID NO: 92             moltype = AA   length = 132
FEATURE                   Location/Qualifiers
REGION                    1..132
                          note = MIC-1 polypeptide plus N-terminal extension
source                    1..132
                          mol_type = protein
                          organism = synthetic construct
SEQUENCE: 92
GEPSGEPSGE PSGEPSGEPS ARNGDHCPLG PGRCCRLHTV RASLEDLGWA DWVLSPREVQ       60
VTMCIGACPS QFRAANMHAQ IKTSLHRLKP DTVPAPCCVP ASYNPMVLIQ KTDTGVSLQT      120
YDDLLAKDCH CI                                                          132

SEQ ID NO: 93             moltype = AA   length = 136
FEATURE                   Location/Qualifiers
REGION                    1..136
                          note = MIC-1 polypeptide plus N-terminal extension
source                    1..136
                          mol_type = protein
                          organism = synthetic construct
SEQUENCE: 93
SPAGSPTSTE EGTSESATPE SGPGARNGDH CPLGPGRCCR LHTVRASLED LGWADWVLSP       60
REVQVTMCIG ACPSQFRAAN MHAQIKTSLH RLKPDTVPAP CCVPASYNPM VLIQKTDTGV      120
SLQTYDDLLA KDCHCI                                                      136

SEQ ID NO: 94             moltype = AA   length = 130
FEATURE                   Location/Qualifiers
REGION                    1..130
                          note = MIC-1 polypeptide plus N-terminal extension
source                    1..130
                          mol_type = protein
                          organism = synthetic construct
SEQUENCE: 94
AEEAEEAEEA EEAEEAEEAE SGDHCPLGPG RCCRLHTVRA SLEDLGWADW VLSPREVQVT       60
MCIGACPSQF RAANMHAQIK TSLHRLKPDT VPAPCCVPAS YNPMVLIQKT DTGVSLQTYD      120
DLLAKDCHCI                                                             130

SEQ ID NO: 95             moltype = AA   length = 127
FEATURE                   Location/Qualifiers
REGION                    1..127
                          note = MIC-1 polypeptide plus N-terminal extension
source                    1..127
                          mol_type = protein
                          organism = synthetic construct
SEQUENCE: 95
AEEAEEEAEEA EEAEEAESGD HCPLGPGRCC RLHTVRASLE DLGWADWVLS PREVQVTMCI       60
GACPSQFRAA NMHAQIKTSL HRLKPDTVPA PCCVPASYNP MVLIQKTDTG VSLQTYDDLL      120
AKDCHCI                                                                127

SEQ ID NO: 96             moltype = AA   length = 121
FEATURE                   Location/Qualifiers
REGION                    1..121
                          note = MIC-1 polypeptide plus N-terminal extension
source                    1..121
                          mol_type = protein
                          organism = synthetic construct
SEQUENCE: 96
AEEAEEAEEA ESGDHCPLGP GRCCRLHTVR ASLEDLGWAD WVLSPREVQV TMCIGACPSQ       60
FRAANMHAQI KTSLHRLKPD TVPAPCCVPA SYNPMVLIQK TDTGVSLQTY DDLLAKDCHC      120
I                                                                      121

SEQ ID NO: 97             moltype = AA   length = 138
FEATURE                   Location/Qualifiers
REGION                    1..138
                          note = MIC-1 polypeptide plus N-terminal extension
source                    1..138
                          mol_type = protein
                          organism = synthetic construct
SEQUENCE: 97
AASPAGSPTS TEEGTSESAT PESGPGARNG DHCPLGPGRC CRLHTVRASL EDLGWADWVL       60
SPREVQVTMC IGACPSQFRA ANMHAQIKTS LHRLKPDTVP APCCVPASYN PMVLIQKTDT      120
GVSLQTYDDL LAKDCHCI                                                    138

SEQ ID NO: 98             moltype = AA   length = 136
FEATURE                   Location/Qualifiers
```

```
REGION                  1..136
                        note = MIC-1 polypeptide plus N-terminal extension
source                  1..136
                        mol_type = protein
                        organism = synthetic construct
SEQUENCE: 98
TSESATPESG PGTSESATPE SGPGAAEGDH CPLGPGRCCR LHTVRASLED LGWADWVLSP    60
REVQVTMCIG ACPSQFRAAN MHAQIKTSLH RLKPDTVPAP CCVPASYNPM VLIQKTDTGV   120
SLQTYDDLLA KDCHCI                                                  136

SEQ ID NO: 99           moltype = AA  length = 135
FEATURE                 Location/Qualifiers
REGION                  1..135
                        note = MIC-1 polypeptide plus N-terminal extension
source                  1..135
                        mol_type = protein
                        organism = synthetic construct
SEQUENCE: 99
AASPAGSPTS TEEGTSESAT PESGPGGDHC PLGPGRCCRL HTVRASLEDL GWADWVLSPR    60
EVQVTMCIGA CPSQFRAANM HAQIKTSLHR LKPDTVPAPC CVPASYNPMV LIQKTDTGVS   120
LQTYDDLLAK DCHCI                                                   135

SEQ ID NO: 100          moltype = AA  length = 131
FEATURE                 Location/Qualifiers
REGION                  1..131
                        note = MIC-1 polypeptide plus N-terminal extension
source                  1..131
                        mol_type = protein
                        organism = synthetic construct
SEQUENCE: 100
AAPEDEETPE QEGSGSGSGS GSGDHCPLGP GRCCRLHTVR ASLEDLGWAD WVLSPREVQV    60
TMCIGACPSQ FRAANMHAQI KTSLHRLKPD TVPAPCCVPA SYNPMVLIQK TDTGVSLQTY   120
DDLLAKDCHC I                                                       131

SEQ ID NO: 101          moltype = AA  length = 121
FEATURE                 Location/Qualifiers
REGION                  1..121
                        note = MIC-1 polypeptide plus N-terminal extension
source                  1..121
                        mol_type = protein
                        organism = synthetic construct
SEQUENCE: 101
AAPEDEETPE QEGDHCPLGP GRCCRLHTVR ASLEDLGWAD WVLSPREVQV TMCIGACPSQ    60
FRAANMHAQI KTSLHRLKPD TVPAPCCVPA SYNPMVLIQK TDTGVSLQTY DDLLAKDCHC   120
I                                                                  121

SEQ ID NO: 102          moltype = AA  length = 131
FEATURE                 Location/Qualifiers
REGION                  1..131
                        note = MIC-1 polypeptide plus N-terminal extension
source                  1..131
                        mol_type = protein
                        organism = synthetic construct
SEQUENCE: 102
AAPDEGTEEE TEGSGSGSGS GSGDHCPLGP GRCCRLHTVR ASLEDLGWAD WVLSPREVQV    60
TMCIGACPSQ FRAANMHAQI KTSLHRLKPD TVPAPCCVPA SYNPMVLIQK TDTGVSLQTY   120
DDLLAKDCHC I                                                       131

SEQ ID NO: 103          moltype = AA  length = 133
FEATURE                 Location/Qualifiers
REGION                  1..133
                        note = MIC-1 polypeptide plus N-terminal extension
source                  1..133
                        mol_type = protein
                        organism = synthetic construct
SEQUENCE: 103
SEPATSGSET PGTSTEPSEG SAPGGDHCPL GPGRCCRLHT VRASLEDLGW ADWVLSPREV    60
QVTMCIGACP SQFRAANMHA QIKTSLHRLK PDTVPAPCCV PASYNPMVLI QKTDTGVSLQ   120
TYDDLLAKDC HCI                                                     133

SEQ ID NO: 104          moltype = AA  length = 133
FEATURE                 Location/Qualifiers
REGION                  1..133
                        note = MIC-1 polypeptide plus N-terminal extension
source                  1..133
                        mol_type = protein
                        organism = synthetic construct
SEQUENCE: 104
SEPATSGSET PGSEPATSGS ETPGGDHCPL GPGRCCRLHT VRASLEDLGW ADWVLSPREV    60
```

```
QVTMCIGACP SQFRAANMHA QIKTSLHRLK PDTVPAPCCV PASYNPMVLI QKTDTGVSLQ    120
TYDDLLAKDC HCI                                                      133

SEQ ID NO: 105           moltype = AA  length = 133
FEATURE                  Location/Qualifiers
REGION                   1..133
                         note = MIC-1 polypeptide plus N-terminal extension
source                   1..133
                         mol_type = protein
                         organism = synthetic construct
SEQUENCE: 105
SEPATSGSET PGSEPATSGS ETPGGDHCPL GPGRCCRLHT VRASLEDLGW ADWVLSPREV    60
QVTMCIGACP SQFRAANEHA QIKTSLHRLK PDTVPAPCCV PASYNPMVLI QKTDTGVSLQ    120
TYDDLLAKDC HCI                                                      133

SEQ ID NO: 106           moltype = AA  length = 133
FEATURE                  Location/Qualifiers
REGION                   1..133
                         note = MIC-1 polypeptide plus N-terminal extension
source                   1..133
                         mol_type = protein
                         organism = synthetic construct
SEQUENCE: 106
SEPATSGSET PGSEPATSGS ETPGGDHCPL GPGRCCRLHT VRASLEDLGW ADWVLSPREV    60
QVTMCIGACP SQFRAANLHA QIKTSLHRLK PDTVPAPCCV PASYNPMVLI QKTDTGVSLQ    120
TYDDLLAKDC HCI                                                      133

SEQ ID NO: 107           moltype = AA  length = 134
FEATURE                  Location/Qualifiers
REGION                   1..134
                         note = MIC-1 polypeptide plus N-terminal extension
source                   1..134
                         mol_type = protein
                         organism = synthetic construct
SEQUENCE: 107
AGPEQGQEPG PEQGQEPGPE QGQEPGDHCP LGPGRCCRLH TVRASLEDLG WADWVLSPRE    60
VQVTMCIGAC PSQFRAANMH AQIKTSLHRL KPDTVPAPCC VPASYNPMVL IQKTDTGVSL    120
QTYDDLLAKD CHCI                                                     134

SEQ ID NO: 108           moltype = AA  length = 139
FEATURE                  Location/Qualifiers
REGION                   1..139
                         note = MIC-1 polypeptide plus N-terminal extension
source                   1..139
                         mol_type = protein
                         organism = synthetic construct
SEQUENCE: 108
SEPATSGSET PGTSESATPE SGPGTSTEPS GDHCPLGPGR CCRLHTVRAS LEDLGWADWV    60
LSPREVQVTM CIGACPSQFR AANMHAQIKT SLHRLKPDTV PAPCCVPASY NPMVLIQKTD    120
TGVSLQTYDD LLAKDCHCI                                                139

SEQ ID NO: 109           moltype = AA  length = 141
FEATURE                  Location/Qualifiers
REGION                   1..141
                         note = MIC-1 polypeptide plus N-terminal extension
source                   1..141
                         mol_type = protein
                         organism = synthetic construct
SEQUENCE: 109
SEPATSGSET PGTSESATPE SGPGTSTEPS EGGDHCPLGP GRCCRLHTVR ASLEDLGWAD    60
WVLSPREVQV TMCIGACPSQ FRAANMHAQI KTSLHRLKPD TVPAPCCVPA SYNPMVLIQK    120
TDTGVSLQTY DDLLAKDCHC I                                             141

SEQ ID NO: 110           moltype = AA  length = 133
FEATURE                  Location/Qualifiers
REGION                   1..133
                         note = MIC-1 polypeptide plus N-terminal extension
source                   1..133
                         mol_type = protein
                         organism = synthetic construct
SEQUENCE: 110
SEPATSGSET PGSEPATSGS ETPGGDHCPL GPGRCCRLHT VRASLEDLGW ADWVLSPREV    60
QVTMCIGACP SQFRAANMHA QIKTSLHRLK PDTVPAPCCV PASYNPLVLI QKTDTGVSLQ    120
TYDDLLAKDC HCI                                                      133

SEQ ID NO: 111           moltype = AA  length = 133
FEATURE                  Location/Qualifiers
REGION                   1..133
                         note = MIC-1 polypeptide plus N-terminal extension
```

```
                              -continued source                  1..133
                        mol_type = protein
                        organism = synthetic construct
SEQUENCE: 111
SEPATSGSET PGSEPATSGS ETPGGDHCPL GPGRCCRLHT VRASLEDLGW ADWVLSPREV    60
QVTMCIGACP SQFRAANLHA QIKTSLHRLK PDTVPAPCCV PASYNPLVLI QKTDTGVSLQ   120
TYDDLLAKDC HCI                                                     133

SEQ ID NO: 112          moltype = AA   length = 133
FEATURE                 Location/Qualifiers
REGION                  1..133
                        note = MIC-1 polypeptide plus N-terminal extension
source                  1..133
                        mol_type = protein
                        organism = synthetic construct
SEQUENCE: 112
SEPATSGSET PGSEPATSGS ETPGGDHCPL GPGRCCRLHT VRASLEDLGW ADWVLSPREV    60
QVTMCIGACP SQFRAANEHA QIKTSLERLK PDTVPAPCCV PASYNPMVLI QKTDTGVSLQ   120
TYDDLLAKDC HCI                                                     133

SEQ ID NO: 113          moltype = AA   length = 133
FEATURE                 Location/Qualifiers
REGION                  1..133
                        note = MIC-1 polypeptide plus N-terminal extension
source                  1..133
                        mol_type = protein
                        organism = synthetic construct
SEQUENCE: 113
SEPATSGSET PGSEPATSGS ETPGGDHCPL GPGRCCRLHT VRASLEDLGW ADWVLSPREV    60
QVTMCIGACP SQFRAANEHA QIKTSLHELK PDTVPAPCCV PASYNPMVLI QKTDTGVSLQ   120
TYDDLLAKDC HCI                                                     133

SEQ ID NO: 114          moltype = AA   length = 133
FEATURE                 Location/Qualifiers
REGION                  1..133
                        note = MIC-1 polypeptide plus N-terminal extension
source                  1..133
                        mol_type = protein
                        organism = synthetic construct
SEQUENCE: 114
SEPATSGSET PGSEPATSGS ETPGGDHCPL GPGRCCRLHT VRASLEDLGW ADWVLSPREV    60
QVTMCIGACP SQFRAANEHA QIKTSLHELK PDTVPAPCCV PASYNPLVLI QKTDTGVSLQ   120
TYDDLLAKDC HCI                                                     133

SEQ ID NO: 115          moltype = AA   length = 140
FEATURE                 Location/Qualifiers
REGION                  1..140
                        note = MIC-1 polypeptide plus N-terminal extension
source                  1..140
                        mol_type = protein
                        organism = synthetic construct
SEQUENCE: 115
SEPATSGSET PGTSESATPE SGPGTSTEPS GGDHCPLGPG RCCRLHTVRA SLEDLGWADW    60
VLSPREVQVT MCIGACPSQF RAANLHAQIK TSLHRLKPDT VPAPCCVPAS YNPLVLIQKT   120
DTGVSLQTYD DLLAKDCHCI                                              140

SEQ ID NO: 116          moltype = AA   length = 133
FEATURE                 Location/Qualifiers
REGION                  1..133
                        note = MIC-1 polypeptide plus N-terminal extension
source                  1..133
                        mol_type = protein
                        organism = synthetic construct
SEQUENCE: 116
GEPSGEPSGE PSGEPSGEPS GEPSGDHCPL GPGRCCRLHT VRASLEDLGW ADWVLSPREV    60
QVTMCIGACP SQFRAANMHA QIKTSLHRLK PDTVPAPCCV PASYNPMVLI QKTDTGVSLQ   120
TYDDLLAKDC HCI                                                     133

SEQ ID NO: 117          moltype = AA   length = 135
FEATURE                 Location/Qualifiers
REGION                  1..135
                        note = MIC-1 polypeptide plus N-terminal extension
source                  1..135
                        mol_type = protein
                        organism = synthetic construct
SEQUENCE: 117
SEPATSGSET PGSEPATSGS ETPGARGDHC PLGPGRCCRL HTVRASLEDL GWADWVLSPR    60
EVQVTMCIGA CPSQFRAANM HAQIKTSLHR LKPDTVPAPC CVPASYNPMV LIQKTDTGVS   120
LQTYDDLLAK DCHCI                                                   135
```

```
SEQ ID NO: 118            moltype = AA   length = 4
FEATURE                   Location/Qualifiers
REGION                    1..4
                          note = N-terminal extension
source                    1..4
                          mol_type = protein
                          organism = synthetic construct
SEQUENCE: 118
GEPS                                                                       4

SEQ ID NO: 119            moltype = AA   length = 4
FEATURE                   Location/Qualifiers
REGION                    1..4
                          note = N-terminal extension
source                    1..4
                          mol_type = protein
                          organism = synthetic construct
SEQUENCE: 119
GPSE                                                                       4

SEQ ID NO: 120            moltype = AA   length = 4
FEATURE                   Location/Qualifiers
REGION                    1..4
                          note = N-terminal extension
source                    1..4
                          mol_type = protein
                          organism = synthetic construct
SEQUENCE: 120
GPES                                                                       4

SEQ ID NO: 121            moltype = AA   length = 4
FEATURE                   Location/Qualifiers
REGION                    1..4
                          note = N-terminal extension
source                    1..4
                          mol_type = protein
                          organism = synthetic construct
SEQUENCE: 121
GSPE                                                                       4

SEQ ID NO: 122            moltype = AA   length = 4
FEATURE                   Location/Qualifiers
REGION                    1..4
                          note = N-terminal extension
source                    1..4
                          mol_type = protein
                          organism = synthetic construct
SEQUENCE: 122
GSEP                                                                       4

SEQ ID NO: 123            moltype = AA   length = 4
FEATURE                   Location/Qualifiers
REGION                    1..4
                          note = N-terminal extension
source                    1..4
                          mol_type = protein
                          organism = synthetic construct
SEQUENCE: 123
GEPQ                                                                       4

SEQ ID NO: 124            moltype = AA   length = 4
FEATURE                   Location/Qualifiers
REGION                    1..4
                          note = N-terminal extension
source                    1..4
                          mol_type = protein
                          organism = synthetic construct
SEQUENCE: 124
GEQP                                                                       4

SEQ ID NO: 125            moltype = AA   length = 4
FEATURE                   Location/Qualifiers
REGION                    1..4
                          note = N-terminal extension
source                    1..4
                          mol_type = protein
                          organism = synthetic construct
SEQUENCE: 125
```

```
GPEQ                                                                        4

SEQ ID NO: 126          moltype = AA  length = 4
FEATURE                 Location/Qualifiers
REGION                  1..4
                        note = N-terminal extension
source                  1..4
                        mol_type = protein
                        organism = synthetic construct
SEQUENCE: 126
GPQE                                                                        4

SEQ ID NO: 127          moltype = AA  length = 4
FEATURE                 Location/Qualifiers
REGION                  1..4
                        note = N-terminal extension
source                  1..4
                        mol_type = protein
                        organism = synthetic construct
SEQUENCE: 127
GQEP                                                                        4

SEQ ID NO: 128          moltype = AA  length = 4
FEATURE                 Location/Qualifiers
REGION                  1..4
                        note = N-terminal extension
source                  1..4
                        mol_type = protein
                        organism = synthetic construct
SEQUENCE: 128
GQPE                                                                        4

SEQ ID NO: 129          moltype = AA  length = 10
FEATURE                 Location/Qualifiers
REGION                  1..10
                        note = N-terminal extension
source                  1..10
                        mol_type = protein
                        organism = synthetic construct
SEQUENCE: 129
PEDEETPEQE                                                                 10

SEQ ID NO: 130          moltype = AA  length = 10
FEATURE                 Location/Qualifiers
REGION                  1..10
                        note = N-terminal extension
source                  1..10
                        mol_type = protein
                        organism = synthetic construct
SEQUENCE: 130
PDEGTEEETE                                                                 10

SEQ ID NO: 131          moltype = AA  length = 10
FEATURE                 Location/Qualifiers
REGION                  1..10
                        note = N-terminal extension
source                  1..10
                        mol_type = protein
                        organism = synthetic construct
SEQUENCE: 131
PAAEEEDDPD                                                                 10

SEQ ID NO: 132          moltype = AA  length = 11
FEATURE                 Location/Qualifiers
REGION                  1..11
                        note = N-terminal extension
source                  1..11
                        mol_type = protein
                        organism = synthetic construct
SEQUENCE: 132
AEPDEDPQSE D                                                               11

SEQ ID NO: 133          moltype = AA  length = 10
FEATURE                 Location/Qualifiers
REGION                  1..10
                        note = N-terminal extension
source                  1..10
                        mol_type = protein
                        organism = synthetic construct
```

```
SEQUENCE: 133
AEPDEDPQSE                                                                    10

SEQ ID NO: 134          moltype = AA  length = 9
FEATURE                 Location/Qualifiers
REGION                  1..9
                        note = N-terminal extension
source                  1..9
                        mol_type = protein
                        organism = synthetic construct
SEQUENCE: 134
AEPEEQEED                                                                      9

SEQ ID NO: 135          moltype = AA  length = 8
FEATURE                 Location/Qualifiers
REGION                  1..8
                        note = N-terminal extension
source                  1..8
                        mol_type = protein
                        organism = synthetic construct
SEQUENCE: 135
AEPEEQEE                                                                       8

SEQ ID NO: 136          moltype = AA  length = 4
FEATURE                 Location/Qualifiers
REGION                  1..4
                        note = N-terminal extension
source                  1..4
                        mol_type = protein
                        organism = synthetic construct
SEQUENCE: 136
GGGS                                                                           4

SEQ ID NO: 137          moltype = AA  length = 4
FEATURE                 Location/Qualifiers
REGION                  1..4
                        note = N-terminal extension
source                  1..4
                        mol_type = protein
                        organism = synthetic construct
SEQUENCE: 137
GSGS                                                                           4

SEQ ID NO: 138          moltype = AA  length = 4
FEATURE                 Location/Qualifiers
REGION                  1..4
                        note = N-terminal extension
source                  1..4
                        mol_type = protein
                        organism = synthetic construct
SEQUENCE: 138
GGSS                                                                           4

SEQ ID NO: 139          moltype = AA  length = 4
FEATURE                 Location/Qualifiers
REGION                  1..4
                        note = N-terminal extension
source                  1..4
                        mol_type = protein
                        organism = synthetic construct
SEQUENCE: 139
SSSG                                                                           4

SEQ ID NO: 140          moltype = AA  length = 20
FEATURE                 Location/Qualifiers
REGION                  1..20
                        note = N-terminal extension
source                  1..20
                        mol_type = protein
                        organism = synthetic construct
SEQUENCE: 140
GEPSGEPSGE PSGEPSGEPS                                                         20

SEQ ID NO: 141          moltype = AA  length = 20
FEATURE                 Location/Qualifiers
REGION                  1..20
                        note = N-terminal extension
source                  1..20
                        mol_type = protein
```

```
                        organism = synthetic construct
SEQUENCE: 141
GPSEGPSEGP SEGPSEGPSE                                                       20

SEQ ID NO: 142          moltype = AA  length = 20
FEATURE                 Location/Qualifiers
REGION                  1..20
                        note = N-terminal extension
source                  1..20
                        mol_type = protein
                        organism = synthetic construct
SEQUENCE: 142
GPESGPESGP ESGPESGPES                                                       20

SEQ ID NO: 143          moltype = AA  length = 20
FEATURE                 Location/Qualifiers
REGION                  1..20
                        note = N-terminal extension
source                  1..20
                        mol_type = protein
                        organism = synthetic construct
SEQUENCE: 143
GSPEGSPEGS PEGSPEGSPE                                                       20

SEQ ID NO: 144          moltype = AA  length = 20
FEATURE                 Location/Qualifiers
REGION                  1..20
                        note = N-terminal extension
source                  1..20
                        mol_type = protein
                        organism = synthetic construct
SEQUENCE: 144
GSEPGSEPGS EPGSEPGSEP                                                       20

SEQ ID NO: 145          moltype = AA  length = 20
FEATURE                 Location/Qualifiers
REGION                  1..20
                        note = N-terminal extension
source                  1..20
                        mol_type = protein
                        organism = synthetic construct
SEQUENCE: 145
GEPQGEPQGE PQGEPQGEPQ                                                       20

SEQ ID NO: 146          moltype = AA  length = 20
FEATURE                 Location/Qualifiers
REGION                  1..20
                        note = N-terminal extension
source                  1..20
                        mol_type = protein
                        organism = synthetic construct
SEQUENCE: 146
GEQPGEQPGE QPGEQPGEQP                                                       20

SEQ ID NO: 147          moltype = AA  length = 20
FEATURE                 Location/Qualifiers
REGION                  1..20
                        note = N-terminal extension
source                  1..20
                        mol_type = protein
                        organism = synthetic construct
SEQUENCE: 147
GPEQGPEQGP EQGPEQGPEQ                                                       20

SEQ ID NO: 148          moltype = AA  length = 20
FEATURE                 Location/Qualifiers
REGION                  1..20
                        note = N-terminal extension
source                  1..20
                        mol_type = protein
                        organism = synthetic construct
SEQUENCE: 148
GPQEGPQEGP QEGPQEGPQE                                                       20

SEQ ID NO: 149          moltype = AA  length = 20
FEATURE                 Location/Qualifiers
REGION                  1..20
                        note = N-terminal extension
source                  1..20
```

```
                        mol_type = protein
                        organism = synthetic construct
SEQUENCE: 149
GQEPGQEPGQ EPGQEPGQEP                                                  20

SEQ ID NO: 150          moltype = AA  length = 20
FEATURE                 Location/Qualifiers
REGION                  1..20
                        note = N-terminal extension
source                  1..20
                        mol_type = protein
                        organism = synthetic construct
SEQUENCE: 150
GQPEGQPEGQ PEGQPEGQPE                                                  20

SEQ ID NO: 151          moltype = AA  length = 15
FEATURE                 Location/Qualifiers
REGION                  1..15
                        note = N-terminal extension
source                  1..15
                        mol_type = protein
                        organism = synthetic construct
SEQUENCE: 151
AEEAEEAEEA EEAEE                                                       15

SEQ ID NO: 152          moltype = AA  length = 7
FEATURE                 Location/Qualifiers
REGION                  1..7
                        note = Linker
source                  1..7
                        mol_type = protein
                        organism = synthetic construct
SEQUENCE: 152
GGSSSGS                                                                 7

SEQ ID NO: 153          moltype = AA  length = 31
FEATURE                 Location/Qualifiers
REGION                  1..31
                        note = Linker
source                  1..31
                        mol_type = protein
                        organism = synthetic construct
SEQUENCE: 153
PTPTPTPTPT PTPTPTPTPT PTPTPTPTPT P                                     31

SEQ ID NO: 154          moltype = AA  length = 111
FEATURE                 Location/Qualifiers
REGION                  1..111
                        note = MIC-1 polypeptide
source                  1..111
                        mol_type = protein
                        organism = synthetic construct
SEQUENCE: 154
ARGDHCPLGP GRCCRLHTVR ASLEDLGWAD WVLSPREVQV TLCIGACPSQ FRAANMHAQI       60
KTSLHRLKPD TVPAPCCVPA SYNPMVLIQK TDTGVSLQTY DDLLAKDCHC I               111

SEQ ID NO: 155          moltype = AA  length = 109
FEATURE                 Location/Qualifiers
REGION                  1..109
                        note = MIC-1 polypeptide
source                  1..109
                        mol_type = protein
                        organism = synthetic construct
SEQUENCE: 155
GDHCPLGPGR CCRLHTVRAS LEDLGWADWV LSPREVQVTL CIGACPSQFR AANMHAQIKT       60
SLHRLKPDTV PAPCCVPASY NPMVLIQKTD TGVSLQTYDD LLAKDCHCI                  109

SEQ ID NO: 156          moltype = AA  length = 111
FEATURE                 Location/Qualifiers
REGION                  1..111
                        note = MIC-1 polypeptide
source                  1..111
                        mol_type = protein
                        organism = synthetic construct
SEQUENCE: 156
ARGDHCPLGP GRCCRLHTVR ASLEDLGWAD WVLSPREVQV TMCIGACPSQ FRAANEHAQI       60
KTSLERLKPD TVPAPCCVPA SYNPMVLIQK TDTGVSLQTY DDLLAKDCHC I               111

SEQ ID NO: 157          moltype = AA  length = 109
```

| | | |
|---|---|---|
| FEATURE | Location/Qualifiers | |
| REGION | 1..109 | |
| | note = MIC-1 polypeptide | |
| source | 1..109 | |
| | mol_type = protein | |
| | organism = synthetic construct | |

SEQUENCE: 157
```
GDHCPLGPGR CCRLHTVRAS LEDLGWADWV LSPREVQVTM CIGACPSQFR AANLHAQIKT   60
SLHRLKPDTV PAPCCVPASY NPMVLIQKTD TGVSLQTYDD LLAKDCHCI              109
```

| | | |
|---|---|---|
| SEQ ID NO: 158 | moltype = AA  length = 111 | |
| FEATURE | Location/Qualifiers | |
| REGION | 1..111 | |
| | note = MIC-1 polypeptide | |
| source | 1..111 | |
| | mol_type = protein | |
| | organism = synthetic construct | |

SEQUENCE: 158
```
ARGDHCPLGP GRCCRLHTVR ASLEDLGWAD WVLSPREVQV TMCIGACPSQ FRAANLHAQI   60
KTSLHRLKPD TVPAPCCVPA SYNPMVLIQK TDTGVSLQTY DDLLAKDCHC I            111
```

| | | |
|---|---|---|
| SEQ ID NO: 159 | moltype = AA  length = 109 | |
| FEATURE | Location/Qualifiers | |
| REGION | 1..109 | |
| | note = MIC-1 polypeptide | |
| source | 1..109 | |
| | mol_type = protein | |
| | organism = synthetic construct | |

SEQUENCE: 159
```
GDHCPLGPGR CCRLHTVRAS LEDLGWADWV LSPREVQVTM CIGACPSQFR AANMHAQIKT   60
SLHRLKPDTV PAPCCVPASY NPLVLIQKTD TGVSLQTYDD LLAKDCHCI              109
```

| | | |
|---|---|---|
| SEQ ID NO: 160 | moltype = AA  length = 111 | |
| FEATURE | Location/Qualifiers | |
| REGION | 1..111 | |
| | note = MIC-1 polypeptide | |
| source | 1..111 | |
| | mol_type = protein | |
| | organism = synthetic construct | |

SEQUENCE: 160
```
ARGDHCPLGP GRCCRLHTVR ASLEDLGWAD WVLSPREVQV TMCIGACPSQ FRAANMHAQI   60
KTSLHRLKPD TVPAPCCVPA SYNPLVLIQK TDTGVSLQTY DDLLAKDCHC I            111
```

| | | |
|---|---|---|
| SEQ ID NO: 161 | moltype = AA  length = 36 | |
| FEATURE | Location/Qualifiers | |
| REGION | 1..36 | |
| | note = N-terminal extension | |
| source | 1..36 | |
| | mol_type = protein | |
| | organism = synthetic construct | |

SEQUENCE: 161
```
GEPSGEPSGE PSGEPSGEPS GEPSGEPSGE PSGEPS                             36
```

| | | |
|---|---|---|
| SEQ ID NO: 162 | moltype = AA  length = 36 | |
| FEATURE | Location/Qualifiers | |
| REGION | 1..36 | |
| | note = N-terminal extension | |
| source | 1..36 | |
| | mol_type = protein | |
| | organism = synthetic construct | |

SEQUENCE: 162
```
GEPQGEPQGE PQGEPQGEPQ GEPQGEPQGE PQGEPQ                             36
```

| | | |
|---|---|---|
| SEQ ID NO: 163 | moltype = AA  length = 25 | |
| FEATURE | Location/Qualifiers | |
| REGION | 1..25 | |
| | note = N-terminal extension | |
| source | 1..25 | |
| | mol_type = protein | |
| | organism = synthetic construct | |

SEQUENCE: 163
```
AGPEQGQEPG EPQGQEPQPG EPEGQ                                         25
```

| | | |
|---|---|---|
| SEQ ID NO: 164 | moltype = AA  length = 143 | |
| FEATURE | Location/Qualifiers | |
| REGION | 1..143 | |
| | note = MIC-1 polypeptide plus N-terminal extension | |
| source | 1..143 | |
| | mol_type = protein | |

```
                                  organism = synthetic construct
SEQUENCE: 164
SEPATSGSET PGTSESATPE SGPGTSTEPS EGARGDHCPL GPGRCCRLHT VRASLEDLGW        60
ADWVLSPREV QVTMCIGACP SQFRAANLHA QIKTSLHRLK PDTVPAPCCV PASYNPLVLI       120
QKTDTGVSLQ TYDDLLAKDC HCI                                              143

SEQ ID NO: 165            moltype = AA  length = 134
FEATURE                   Location/Qualifiers
REGION                    1..134
                          note = MIC-1 polypeptide plus N-terminal extension
source                    1..134
                          mol_type = protein
                          organism = synthetic construct
SEQUENCE: 165
AGPEQGQEPG EPQGQEPQPG EPEGQGDHCP LGPGRCCRLH TVRASLEDLG WADWVLSPRE        60
VQVTMCIGAC PSQFRAANMH AQIKTSLHRL KPDTVPAPCC VPASYNPMVL IQKTDTGVSL       120
QTYDDLLAKD CHCI                                                        134

SEQ ID NO: 166            moltype = AA  length = 12
FEATURE                   Location/Qualifiers
REGION                    1..12
                          note = N-terminal extension
source                    1..12
                          mol_type = protein
                          organism = synthetic construct
SEQUENCE: 166
SPAGSPTSTE EG                                                           12

SEQ ID NO: 167            moltype = AA  length = 12
FEATURE                   Location/Qualifiers
REGION                    1..12
                          note = N-terminal extension
source                    1..12
                          mol_type = protein
                          organism = synthetic construct
SEQUENCE: 167
TSESATPESG PG                                                           12

SEQ ID NO: 168            moltype = AA  length = 12
FEATURE                   Location/Qualifiers
REGION                    1..12
                          note = N-terminal extension
source                    1..12
                          mol_type = protein
                          organism = synthetic construct
SEQUENCE: 168
TSTEPSEGSA PG                                                           12

SEQ ID NO: 169            moltype = AA  length = 12
FEATURE                   Location/Qualifiers
REGION                    1..12
                          note = N-terminal extension
source                    1..12
                          mol_type = protein
                          organism = synthetic construct
SEQUENCE: 169
SEPATSGSET PG                                                           12

SEQ ID NO: 170            moltype = AA  length = 24
FEATURE                   Location/Qualifiers
REGION                    1..24
                          note = N-terminal extension
source                    1..24
                          mol_type = protein
                          organism = synthetic construct
SEQUENCE: 170
SPAGSPTSTE EGSPAGSPTS TEEG                                              24

SEQ ID NO: 171            moltype = AA  length = 24
FEATURE                   Location/Qualifiers
REGION                    1..24
                          note = N-terminal extension
source                    1..24
                          mol_type = protein
                          organism = synthetic construct
SEQUENCE: 171
SPAGSPTSTE EGTSTEPSEG SAPG                                              24

SEQ ID NO: 172            moltype = AA  length = 24
```

```
FEATURE              Location/Qualifiers
REGION               1..24
                     note = N-terminal extension
source               1..24
                     mol_type = protein
                     organism = synthetic construct
SEQUENCE: 172
SPAGSPTSTE EGSEPATSGS ETPG                                              24

SEQ ID NO: 173       moltype = AA  length = 24
FEATURE              Location/Qualifiers
REGION               1..24
                     note = N-teminal extension
source               1..24
                     mol_type = protein
                     organism = synthetic construct
SEQUENCE: 173
TSESATPESG PGSPAGSPTS TEEG                                              24

SEQ ID NO: 174       moltype = AA  length = 24
FEATURE              Location/Qualifiers
REGION               1..24
                     note = N-external extension
source               1..24
                     mol_type = protein
                     organism = synthetic construct
SEQUENCE: 174
TSESATPESG PGTSESATPE SGPG                                              24

SEQ ID NO: 175       moltype = AA  length = 24
FEATURE              Location/Qualifiers
REGION               1..24
                     note = N-terminal extension
source               1..24
                     mol_type = protein
                     organism = synthetic construct
SEQUENCE: 175
TSESATPESG PGTSTEPSEG SAPG                                              24

SEQ ID NO: 176       moltype = AA  length = 24
FEATURE              Location/Qualifiers
REGION               1..24
                     note = N-terminal extension
source               1..24
                     mol_type = protein
                     organism = synthetic construct
SEQUENCE: 176
TSESATPESG PGSEPATSGS ETPG                                              24

SEQ ID NO: 177       moltype = AA  length = 24
FEATURE              Location/Qualifiers
REGION               1..24
                     note = N-terminal extension
source               1..24
                     mol_type = protein
                     organism = synthetic construct
SEQUENCE: 177
TSTEPSEGSA PGSPAGSPTS TEEG                                              24

SEQ ID NO: 178       moltype = AA  length = 24
FEATURE              Location/Qualifiers
REGION               1..24
                     note = N-terminal extension
source               1..24
                     mol_type = protein
                     organism = synthetic construct
SEQUENCE: 178
TSTEPSEGSA PGTSESATPE SGPG                                              24

SEQ ID NO: 179       moltype = AA  length = 24
FEATURE              Location/Qualifiers
REGION               1..24
                     note = N-terminal extension
source               1..24
                     mol_type = protein
                     organism = synthetic construct
SEQUENCE: 179
TSTEPESGSA PGTSTEPESG SAPG                                              24
```

```
SEQ ID NO: 180               moltype = AA   length = 24
FEATURE                      Location/Qualifiers
REGION                       1..24
                             note = N-terminal extension
source                       1..24
                             mol_type = protein
                             organism = synthetic construct
SEQUENCE: 180
TSTEPSEGSA PGSEPATSGS ETPG                                              24

SEQ ID NO: 181               moltype = AA   length = 24
FEATURE                      Location/Qualifiers
REGION                       1..24
                             note = N-terminal extension
source                       1..24
                             mol_type = protein
                             organism = synthetic construct
SEQUENCE: 181
SEPATSGSET PGSEPATSGS ETPG                                              24

SEQ ID NO: 182               moltype = AA   length = 133
FEATURE                      Location/Qualifiers
REGION                       1..133
                             note = MIC-1 polypeptide plus N-terminal extension
source                       1..133
                             mol_type = protein
                             organism = synthetic construct
SEQUENCE: 182
SEPATSGSET PGTSESATPE SGPGGDHCPL GPGRCCRLHT VRASLEDLGW ADWVLSPREV        60
QVTMCIGACP SQFRAANMHA QIKTSLHRLK PDTVPAPCCV PASYNPMVLI QKTDTGVSLQ       120
TYDDLLAKDC HCI                                                         133

SEQ ID NO: 183               moltype = AA   length = 30
FEATURE                      Location/Qualifiers
REGION                       1..30
                             note = N-terminal extension
source                       1..30
                             mol_type = protein
                             organism = synthetic construct
SEQUENCE: 183
SEPATSGSET PGTSESATPE SGPGESATPE                                        30

SEQ ID NO: 184               moltype = AA   length = 30
FEATURE                      Location/Qualifiers
REGION                       1..30
                             note = N-terminal extension
source                       1..30
                             mol_type = protein
                             organism = synthetic construct
SEQUENCE: 184
SEPATSGSET PGTSESATPE SGPGSTEPSE                                        30

SEQ ID NO: 185               moltype = AA   length = 30
FEATURE                      Location/Qualifiers
REGION                       1..30
                             note = N-terminal extension
source                       1..30
                             mol_type = protein
                             organism = synthetic construct
SEQUENCE: 185
SEPATSGSET PGTSTEPSEG SAPGTSTEEG                                        30

SEQ ID NO: 186               moltype = AA   length = 30
FEATURE                      Location/Qualifiers
REGION                       1..30
                             note = N-terminal extension
source                       1..30
                             mol_type = protein
                             organism = synthetic construct
SEQUENCE: 186
SEPATSGSET PGTSTEPSEG SAPGTSESAT                                        30

SEQ ID NO: 187               moltype = AA   length = 30
FEATURE                      Location/Qualifiers
REGION                       1..30
                             note = N-terminal extension
source                       1..30
                             mol_type = protein
                             organism = synthetic construct
```

```
SEQUENCE: 187
SEPATSGSET PGTSTEPSEG SAPGTSTEPS                                  30

SEQ ID NO: 188          moltype = AA  length = 30
FEATURE                 Location/Qualifiers
REGION                  1..30
                        note = N-terminal extension
source                  1..30
                        mol_type = protein
                        organism = synthetic construct
SEQUENCE: 188
SEPATSGSET PGTSTEPSEG SAPGSEPATS                                  30

SEQ ID NO: 189          moltype = AA  length = 30
FEATURE                 Location/Qualifiers
REGION                  1..30
                        note = N-terminal extension
source                  1..30
                        mol_type = protein
                        organism = synthetic construct
SEQUENCE: 189
SEPATSGSET PGSEPATSGS ETPGTSTEEG                                  30

SEQ ID NO: 190          moltype = AA  length = 30
FEATURE                 Location/Qualifiers
REGION                  1..30
                        note = N-terminal extension
source                  1..30
                        mol_type = protein
                        organism = synthetic construct
SEQUENCE: 190
SEPATSGSET PGSEPATSGS ETPGTSESAT                                  30

SEQ ID NO: 191          moltype = AA  length = 30
FEATURE                 Location/Qualifiers
REGION                  1..30
                        note = N-terminal extension
source                  1..30
                        mol_type = protein
                        organism = synthetic construct
SEQUENCE: 191
SEPATSGSET PGSEPATSGS ETPGESATPE                                  30

SEQ ID NO: 192          moltype = AA  length = 30
FEATURE                 Location/Qualifiers
REGION                  1..30
                        note = N-terminal extension
source                  1..30
                        mol_type = protein
                        organism = synthetic construct
SEQUENCE: 192
SEPATSGSET PGSEPATSGS ETPGTSTEPS                                  30

SEQ ID NO: 193          moltype = AA  length = 30
FEATURE                 Location/Qualifiers
REGION                  1..30
                        note = N-terminal extension
source                  1..30
                        mol_type = protein
                        organism = synthetic construct
SEQUENCE: 193
SEPATSGSET PGSEPATSGS ETPGSTEPSE                                  30

SEQ ID NO: 194          moltype = AA  length = 30
FEATURE                 Location/Qualifiers
REGION                  1..30
                        note = N-terminal extension
source                  1..30
                        mol_type = protein
                        organism = synthetic construct
SEQUENCE: 194
SEPATSGSET PGSEPATSGS ETPGSEPATS                                  30

SEQ ID NO: 195          moltype = AA  length = 32
FEATURE                 Location/Qualifiers
REGION                  1..32
                        note = N-terminal extension
source                  1..32
                        mol_type = protein
```

```
                         organism = synthetic construct
SEQUENCE: 195
SEPATSGSET PGTSESATPE SGPGGPEQGP EQ                              32

SEQ ID NO: 196          moltype = AA   length = 32
FEATURE                 Location/Qualifiers
REGION                  1..32
                        note = N-terminal extension
source                  1..32
                        mol_type = protein
                        organism = synthetic construct
SEQUENCE: 196
SEPATSGSET PGTSESATPE SGPGGEPSGE PS                              32

SEQ ID NO: 197          moltype = AA   length = 36
FEATURE                 Location/Qualifiers
REGION                  1..36
                        note = N-terminal extension
source                  1..36
                        mol_type = protein
                        organism = synthetic construct
SEQUENCE: 197
SEPATSGSET PGTSESATPE SGPGTSTEPS EGSAPG                          36

SEQ ID NO: 198          moltype = AA   length = 48
FEATURE                 Location/Qualifiers
REGION                  1..48
                        note = N-terminal extension
source                  1..48
                        mol_type = protein
                        organism = synthetic construct
SEQUENCE: 198
SEPATSGSET PGTSESATPE SGPGTSTEPS EGSAPGTSTE PSEGSAPG             48

SEQ ID NO: 199          moltype = AA   length = 60
FEATURE                 Location/Qualifiers
REGION                  1..60
                        note = N-terminal extension
source                  1..60
                        mol_type = protein
                        organism = synthetic construct
SEQUENCE: 199
SPAGSPTSTE EGTSESATPE SGPGTSTEPS EGSAPGSPAG SPTSTEEGTS TEPSEGSAPG 60

SEQ ID NO: 200          moltype = AA   length = 139
FEATURE                 Location/Qualifiers
REGION                  1..139
                        note = MIC-1 polypeptide plus N-terminal extension
source                  1..139
                        mol_type = protein
                        organism = synthetic construct
SEQUENCE: 200
SEPATSGSET PGTSESATPE SGPGTSTEEG GDHCPLGPGR CCRLHTVRAS LEDLGWADWV 60
LSPREVQVTM CIGACPSQFR AANMHAQIKT SLHRLKPDTV PAPCCVPASY NPMVLIQKTD 120
TGVSLQTYDD LLAKDCHCI                                            139

SEQ ID NO: 201          moltype = AA   length = 139
FEATURE                 Location/Qualifiers
REGION                  1..139
                        note = MIC-1 polypeptide plus N-terminal extension
source                  1..139
                        mol_type = protein
                        organism = synthetic construct
SEQUENCE: 201
SEPATSGSET PGTSESATPE SGPGTSESAT GDHCPLGPGR CCRLHTVRAS LEDLGWADWV 60
LSPREVQVTM CIGACPSQFR AANMHAQIKT SLHRLKPDTV PAPCCVPASY NPMVLIQKTD 120
TGVSLQTYDD LLAKDCHCI                                            139

SEQ ID NO: 202          moltype = AA   length = 139
FEATURE                 Location/Qualifiers
REGION                  1..139
                        note = MIC-1 polypeptide plus N-terminal extension
source                  1..139
                        mol_type = protein
                        organism = synthetic construct
SEQUENCE: 202
SEPATSGSET PGTSESATPE SGPGESATPE GDHCPLGPGR CCRLHTVRAS LEDLGWADWV 60
LSPREVQVTM CIGACPSQFR AANMHAQIKT SLHRLKPDTV PAPCCVPASY NPMVLIQKTD 120
TGVSLQTYDD LLAKDCHCI                                            139
```

```
SEQ ID NO: 203          moltype = AA  length = 139
FEATURE                 Location/Qualifiers
REGION                  1..139
                        note = MIC-1 polypeptide plus N-terminal extension
source                  1..139
                        mol_type = protein
                        organism = synthetic construct
SEQUENCE: 203
SEPATSGSET PGTSESATPE SGPGSTEPSE GDHCPLGPGR CCRLHTVRAS LEDLGWADWV    60
LSPREVQVTM CIGACPSQFR AANMHAQIKT SLHRLKPDTV PAPCCVPASY NPMVLIQKTD   120
TGVSLQTYDD LLAKDCHCI                                                139

SEQ ID NO: 204          moltype = AA  length = 139
FEATURE                 Location/Qualifiers
REGION                  1..139
                        note = MIC-1 polypeptide plus N-terminal extension
source                  1..139
                        mol_type = protein
                        organism = synthetic construct
SEQUENCE: 204
SEPATSGSET PGTSESATPE SGPGSEPATS GDHCPLGPGR CCRLHTVRAS LEDLGWADWV    60
LSPREVQVTM CIGACPSQFR AANMHAQIKT SLHRLKPDTV PAPCCVPASY NPMVLIQKTD   120
TGVSLQTYDD LLAKDCHCI                                                139

SEQ ID NO: 205          moltype = AA  length = 139
FEATURE                 Location/Qualifiers
REGION                  1..139
                        note = MIC-1 polypeptide plus N-terminal extension
source                  1..139
                        mol_type = protein
                        organism = synthetic construct
SEQUENCE: 205
SEPATSGSET PGTSTEPSEG SAPGTSTEEG GDHCPLGPGR CCRLHTVRAS LEDLGWADWV    60
LSPREVQVTM CIGACPSQFR AANLHAQIKT SLHRLKPDTV PAPCCVPASY NPMVLIQKTD   120
TGVSLQTYDD LLAKDCHCI                                                139

SEQ ID NO: 206          moltype = AA  length = 139
FEATURE                 Location/Qualifiers
REGION                  1..139
                        note = MIC-1 polypeptide plus N-terminal extension
source                  1..139
                        mol_type = protein
                        organism = synthetic construct
SEQUENCE: 206
SEPATSGSET PGTSTEPSEG SAPGTSESAT GDHCPLGPGR CCRLHTVRAS LEDLGWADWV    60
LSPREVQVTM CIGACPSQFR AANLHAQIKT SLHRLKPDTV PAPCCVPASY NPMVLIQKTD   120
TGVSLQTYDD LLAKDCHCI                                                139

SEQ ID NO: 207          moltype = AA  length = 139
FEATURE                 Location/Qualifiers
REGION                  1..139
                        note = MIC-1 polypeptide plus N-terminal extension
source                  1..139
                        mol_type = protein
                        organism = synthetic construct
SEQUENCE: 207
SEPATSGSET PGTSTEPSEG SAPGTSTEPS GDHCPLGPGR CCRLHTVRAS LEDLGWADWV    60
LSPREVQVTM CIGACPSQFR AANLHAQIKT SLHRLKPDTV PAPCCVPASY NPMVLIQKTD   120
TGVSLQTYDD LLAKDCHCI                                                139

SEQ ID NO: 208          moltype = AA  length = 139
FEATURE                 Location/Qualifiers
REGION                  1..139
                        note = MIC-1 polypeptide plus N-terminal extension
source                  1..139
                        mol_type = protein
                        organism = synthetic construct
SEQUENCE: 208
SEPATSGSET PGTSTEPSEG SAPGSEPATS GDHCPLGPGR CCRLHTVRAS LEDLGWADWV    60
LSPREVQVTM CIGACPSQFR AANLHAQIKT SLHRLKPDTV PAPCCVPASY NPMVLIQKTD   120
TGVSLQTYDD LLAKDCHCI                                                139

SEQ ID NO: 209          moltype = AA  length = 139
FEATURE                 Location/Qualifiers
REGION                  1..139
                        note = MIC-1 polypeptide plus N-terminal extension
source                  1..139
                        mol_type = protein
```

```
                            organism = synthetic construct
SEQUENCE: 209
SEPATSGSET PGSEPATSGS ETPGTSTEEG GDHCPLGPGR CCRLHTVRAS LEDLGWADWV    60
LSPREVQVTM CIGACPSQFR AANLHAQIKT SLHRLKPDTV PAPCCVPASY NPMVLIQKTD   120
TGVSLQTYDD LLAKDCHCI                                                139

SEQ ID NO: 210           moltype = AA  length = 139
FEATURE                  Location/Qualifiers
REGION                   1..139
                         note = MIC-1 polypeptide plus N-terminal extension
source                   1..139
                         mol_type = protein
                         organism = synthetic construct
SEQUENCE: 210
SEPATSGSET PGSEPATSGS ETPGTSESAT GDHCPLGPGR CCRLHTVRAS LEDLGWADWV    60
LSPREVQVTM CIGACPSQFR AANMHAQIKT SLHRLKPDTV PAPCCVPASY NPMVLIQKTD   120
TGVSLQTYDD LLAKDCHCI                                                139

SEQ ID NO: 211           moltype = AA  length = 139
FEATURE                  Location/Qualifiers
REGION                   1..139
                         note = MIC-1 polypeptide plus N-termnal extension
source                   1..139
                         mol_type = protein
                         organism = synthetic construct
SEQUENCE: 211
SEPATSGSET PGSEPATSGS ETPGESATPE GDHCPLGPGR CCRLHTVRAS LEDLGWADWV    60
LSPREVQVTM CIGACPSQFR AANMHAQIKT SLHRLKPDTV PAPCCVPASY NPMVLIQKTD   120
TGVSLQTYDD LLAKDCHCI                                                139

SEQ ID NO: 212           moltype = AA  length = 139
FEATURE                  Location/Qualifiers
REGION                   1..139
                         note = MIC-1 polypeptide plus N-terminal extension
source                   1..139
                         mol_type = protein
                         organism = synthetic construct
SEQUENCE: 212
SEPATSGSET PGSEPATSGS ETPGTSTEPS GDHCPLGPGR CCRLHTVRAS LEDLGWADWV    60
LSPREVQVTM CIGACPSQFR AANLHAQIKT SLHRLKPDTV PAPCCVPASY NPMVLIQKTD   120
TGVSLQTYDD LLAKDCHCI                                                139

SEQ ID NO: 213           moltype = AA  length = 139
FEATURE                  Location/Qualifiers
REGION                   1..139
                         note = MIC-1 polypeptide plus N-terminal extension
source                   1..139
                         mol_type = protein
                         organism = synthetic construct
SEQUENCE: 213
SEPATSGSET PGSEPATSGS ETPGSTEPSE GDHCPLGPGR CCRLHTVRAS LEDLGWADWV    60
LSPREVQVTM CIGACPSQFR AANMHAQIKT SLHRLKPDTV PAPCCVPASY NPMVLIQKTD   120
TGVSLQTYDD LLAKDCHCI                                                139

SEQ ID NO: 214           moltype = AA  length = 139
FEATURE                  Location/Qualifiers
REGION                   1..139
                         note = MIC-1 polypeptide plus N-terminal extension
source                   1..139
                         mol_type = protein
                         organism = synthetic construct
SEQUENCE: 214
SEPATSGSET PGSEPATSGS ETPGSEPATS GDHCPLGPGR CCRLHTVRAS LEDLGWADWV    60
LSPREVQVTM CIGACPSQFR AANMHAQIKT SLHRLKPDTV PAPCCVPASY NPMVLIQKTD   120
TGVSLQTYDD LLAKDCHCI                                                139

SEQ ID NO: 215           moltype = AA  length = 141
FEATURE                  Location/Qualifiers
REGION                   1..141
                         note = MIC-1 polypeptide plus N-terminal extension
source                   1..141
                         mol_type = protein
                         organism = synthetic construct
SEQUENCE: 215
SEPATSGSET PGTSESATPE SGPGGPEQGP EQGDHCPLGP GRCCRLHTVR ASLEDLGWAD    60
WVLSPREVQV TMCIGACPSQ FRAANMHAQI KTSLHRLKPD TVPAPCCVPA SYNPMVLIQK   120
TDTGVSLQTY DDLLAKDCHC I                                             141
```

```
SEQ ID NO: 216          moltype = AA  length = 141
FEATURE                 Location/Qualifiers
REGION                  1..141
                        note = MIC-1 polypeptide plus N-terminal extension
source                  1..141
                        mol_type = protein
                        organism = synthetic construct
SEQUENCE: 216
SEPATSGSET PGTSESATPE SGPGGEPSGE PSGDHCPLGP GRCCRLHTVR ASLEDLGWAD     60
WVLSPREVQV TMCIGACPSQ FRAANMHAQI KTSLHRLKPD TVPAPCCVPA SYNPMVLIQK    120
TDTGVSLQTY DDLLAKDCHC I                                              141

SEQ ID NO: 217          moltype = AA  length = 147
FEATURE                 Location/Qualifiers
REGION                  1..147
                        note = MIC-1 polypeptide plus N-terminal extension
source                  1..147
                        mol_type = protein
                        organism = synthetic construct
SEQUENCE: 217
SEPATSGSET PGTSESATPE SGPGTSTEPS EGSAPGARGD HCPLGPGRCC RLHTVRASLE     60
DLGWADWVLS PREVQVTMCI GACPSQFRAA NMHAQIKTSL HRLKPDTVPA PCCVPASYNP    120
MVLIQKTDTG VSLQTYDDLL AKDCHCI                                        147

SEQ ID NO: 218          moltype = AA  length = 159
FEATURE                 Location/Qualifiers
REGION                  1..159
                        note = MIC-1 polypeptide plus N-terminal extension
source                  1..159
                        mol_type = protein
                        organism = synthetic construct
SEQUENCE: 218
SEPATSGSET PGTSESATPE SGPGTSTEPS EGSAPGTSTE PSEGSAPGAR GDHCPLGPGR     60
CCRLHTVRAS LEDLGWADWV LSPREVQVTM CIGACPSQFR AANMHAQIKT SLHRLKPDTV    120
PAPCCVPASY NPMVLIQKTD TGVSLQTYDD LLAKDCHCI                            159

SEQ ID NO: 219          moltype = AA  length = 172
FEATURE                 Location/Qualifiers
REGION                  1..172
                        note = MIC-1 polypeptide plus N-terminal extension
source                  1..172
                        mol_type = protein
                        organism = synthetic construct
SEQUENCE: 219
SPAGSPTSTE EGTSESATPE SGPGTSTEPS EGSAPGSPAG SPTSTEEGTS TEPSEGSAPG     60
ARNGDHCPLG PGRCCRLHTV RASLEDLGWA DWVLSPREVQ VTMCIGACPS QFRAANMHAQ    120
IKTSLHRLKP DTVPAPCCVP ASYNPMVLIQ KTDTGVSLQT YDDLLAKDCH CI             172

SEQ ID NO: 220          moltype = AA  length = 133
FEATURE                 Location/Qualifiers
REGION                  1..133
                        note = MIC-1 polypeptide plus N-terminal extension
source                  1..133
                        mol_type = protein
                        organism = synthetic construct
SEQUENCE: 220
SEPATSGSET PGSEPATSGS ETPGGDHCPL GPGRCCRLHT VRASLEDLGW ADWVLSPREV     60
QVTMCIGACP SQFRAANEHA QIKTSLEELK PDTVPAPCCV PASYNPMVLI QKTDTGVSLQ    120
TYDDLLAKDC HCI                                                        133

SEQ ID NO: 221          moltype = AA  length = 139
FEATURE                 Location/Qualifiers
REGION                  1..139
                        note = MIC-1 polypeptide plus N-terminal extension
source                  1..139
                        mol_type = protein
                        organism = synthetic construct
SEQUENCE: 221
SEPATSGSET PGTSESATPE SGPGTSTEPS GDHCPLGPGR CCRLHTVRAS LEDLGWADWV     60
LSPREVQVTM CIGACPSQFR AANEHAQIKT SLHELKPDTV PAPCCVPASY NPMVLIQKTD    120
TGVSLQTYDD LLAKDCHCI                                                  139

SEQ ID NO: 222          moltype = AA  length = 111
FEATURE                 Location/Qualifiers
REGION                  1..111
                        note = MIC-1 polypeptide
```

```
source                   1..111
                         mol_type = protein
                         organism = synthetic construct
SEQUENCE: 222
ARGDHCPLGP GRCCRLHTVR ASLEDLGWAD WVLSPREVQV TMCIGACPSQ FRAANLHAQI   60
KTSLHRLKPD TVPAPCCVPA SYNPLVLIQK TDTGVSLQTY DDLLAKDCHC I           111
```

MIC-1 COMPOUNDS AND USE THEREOF

CROSS-REFERENCE TO RELATED APPLICATIONS

This application is a Continuation of U.S. application Ser. No. 17/194,908, filed Mar. 8, 2021 which is a continuation of U.S. application Ser. No. 16/303,516, filed Nov. 20, 2018, which is a 35 U.S.C. § 371 National Stage application of International Application PCT/EP2017/062583 (published as WO/2017/202936), filed May 24, 2017, which claims priority to Chinese Patent Applications PCT/CN2016/103574, filed Oct. 27, 2016 and PCT/CN2016/083104, Filed May 24, 2016; the contents thereof which are incorporated by reference in their entirety.

TECHNICAL FIELD

The present invention relates to MIC-1 compounds and their pharmaceutical use.

INCORPORATION-BY-REFERENCE OF THE SEQUENCE LISTING

The instant application contains a Sequence Listing which has been submitted in XML format via the USPTO patent electronic filing system and is hereby incorporated by reference in its entirety. Said XML file, created on Dec. 14, 2022, is named 160031US03.xml and is 284 kilobytes in size.

BACKGROUND OF INVENTION

Macrophage Inhibitory Cytokine-1 (MIC-1) was first described in 1997 (Bootcov et al, Proc. Natl. Acad. Sci. October 1997) based on experiments showing increased expression in activated macrophages. MIC-1 has subsequently been identified by others and given several additional names such as placental transforming growth factor beta (PTGF-β), placental bone morphogenetic protein, growth differentiation factor-15 (GDF15), prostate derived factor (PDF), non-steroidal anti-inflammatory drug-activated gene (NAG-1) and PL74.

MIC-1 is a distant member of the TGF-beta super family, a family of peptide hormones involved in cell growth and differentiation. MIC-1 circulates as a cysteine-rich homodimer with a molecular mass of 24.5 kDa. MIC-1 was initially reported to be up-regulated in macrophages by stimuli including IL-1b, TNF-alpha, IL-2, and TGF-b. It was also shown that MIC-1 could reduce lipopolysaccharide-induced TNF-alpha production and it was based on these data proposed that MIC-1 was an anti-inflammatory cytokine.

More recently, (Johnen et al, Nat Med., November 2007) data from patients with advanced cancer showed that weight loss correlated with circulating levels of MIC-1. These data indicates that MIC-1 regulates body weight. This hypothesis was tested in mice xenografted with prostate tumor cells, where elevated MIC-1 levels were associated with loss of body weight and decreased food intake, an effect which could be reversed by administration of neutralising antibodies against MIC-1. As administration of recombinant MIC-1 to mice regulated hypothalamic neuropeptide Y and pro-opiomelanocortin it was proposed that MIC-1 regulates food intake by a central mechanism. Furthermore, transgenic mice overexpressing MIC-1 are gaining less weight and body fat both on a normal low fat diet and on a high fat diet (Macia et al, PLoS One, April 2012). Also, transgenic mice overexpressing MIC-1 fed both on a low and high fat diet, respectively, had improved glucose tolerance compared with wild type animals on a comparable diet.

Obesity is most commonly caused by excessive calorie intake alone or in conjunction with decreased energy expenditure and/or lack of physical exercise. Obesity is a well-established risk factor for metabolic diseases like diabetes, cardiovascular diseases, sleep apnea and cancer.

SUMMARY OF INVENTION

Described herein are MIC-1 compounds comprising MIC-1 polypeptides with N-terminal amino acid extensions.

In one aspect, the MIC-1 compounds of the invention have good biophysical properties. These properties include but are not limited to solubility and stability. In one aspect, the MIC-1 compounds of the invention have improved solubility. In one aspect, the MIC-1 compounds of the invention have improved chemical stability.

In one aspect, the compounds of the invention have improved biophysical stability as shown by reduced crystal forming tendency.

In one aspect, the MIC-1 compounds of the invention have retained MIC-1 receptor potency and in vivo efficacy on lowering food intake and body weight. These MIC-1 compounds can therefore be used for treatment of metabolic disorders such as obesity, diabetes, cardiovascular diseases like dyslipidaemia and arteriosclerosis and other disorders such as steatohepatitis and diabetic nephropathy.

In one aspect, the MIC-1 compounds of the invention comprises a MIC-1 polypeptide and an N-terminal amino acid extension, wherein said extension consists of 3 to 36 amino acid residues and where the compound has a calculated pI lower than 6.5.

In some embodiments of the invention the MIC-1 compound has a calculated pI that is lower than 6.1.

In some embodiments of the invention the MIC-1 compound has a calculated pI that is higher than 4.7.

In some embodiments of the invention the MIC-1 compound has a calculated pI that is higher than 4.7 and lower than 6.1.

In some embodiments of the invention the MIC-1 compound has a calculated pI is in the range of 5.8-5.2.

In some embodiments the MIC-1 compounds of the invention, as homodimers, have between 218-296, 224-296 or 230-296 amino acid residues.

In some embodiments the MIC-1 compounds of the invention comprise an N-terminal extension that is in the range of 3-35, 3-30, 3-25, 3-24, 4-36, 4-35, 4-30, 4-25, 4-24, 5-36, 5-35, 5-30, 5-25, 5-24, 6-36, 6-35, 6-30, 6-25, 6-24, 7-36, 7-35, 7-30, 7-25, 7-24, 8-36, 8-35, 8-30, 8-25, 8-24, 8-12, 30-36, 32-36, 30-34, or 30-32 amino acid residues in length.

In some embodiments the MIC-1 compounds of the invention comprise an N-terminal extension that is in the range of 30-32 amino acid residues in length.

In some embodiments the MIC-1 compounds of the invention comprise an N-terminal extension that has surplus of acidic amino acid residues (Aspartic acid and Glutamic acid) of at least 3, 4, 5 or 6 compared to the number of basic amino acid residues (Lysine, Arginine and Histidine).

In some embodiments of the invention the MIC-1 compounds comprise N-terminal extensions composed of amino acid residues selected among the group consisting of A, E, G, P, S, T, Q, and D wherein said extension comprises at least three E and/or D amino acid residues.

In some embodiments the MIC-1 compounds of the invention comprise an MIC-1 polypeptide that display at least 85%, 90%, 95% or 98% sequence identity to MIC-1 of SEQ ID NO:1.

In some embodiments the MIC-1 compounds of the invention comprise an MIC-1 polypeptide that comprises one or more of the following substitutions N3E, P11E, H18E, R21E, A30E, A47E, R53E, A54E, M57E, M57L, R67E, L68E, K69E, A75E, A81E, P85E, M86L, L105E, and K107E compared to MIC-1 of SEQ ID NO:1 and/or a deletion of the first three residues (MIC-1-Δ1-3) or a deletion of N3 (des-N3) compared to MIC-1 of SEQ ID NO:1.

In a particular embodiment of the invention the MIC-1 compound comprises a MIC-1 polypeptide and an N-terminal amino acid extension with an amino acid sequence according to SEQ ID NO: 87, 90, 92, 93, 94, 97, 98, 99, 100, 101, 102, 108, 109, or 164.

In one aspect, the invention provides MIC-1 compounds having a solubility of about 0.5, 1.0, 5.0, 10, 30 or 50 mg/ml at pH 8.0 in a tris(hydroxymethyl)aminomethane (Tris) buffer system.

In one aspect, the invention provides a polynucleotide molecule encoding a MIC-1 compound of the invention.

In one aspect, the invention provides a pharmaceutical composition comprising the MIC-1 compound of the invention or a pharmaceutically acceptable salt, amide or ester thereof, and one or more pharmaceutically acceptable excipients.

In one aspect, the invention provides a MIC-1 compound of the invention for use as a medicament.

In one aspect, the invention provides a MIC-1 compound of the invention for use in the prevention and/or treatment of a metabolic disorder, wherein the metabolic disorder is obesity, type 2 diabetes, dyslipidemia, or diabetic nephropathy.

In one aspect, the invention provides a MIC-1 compound of the invention for use in the prevention and/or treatment of eating disorders, such as obesity, e.g. by decreasing food intake, reducing body weight, suppressing appetite and inducing satiety.

In one aspect, the invention provides a MIC-1 compound of the invention for use in the prevention and/or treatment of obesity.

In one aspect, the compounds of the invention are MIC-1 receptor agonists. In one aspect, the compounds of the invention inhibit food intake. In one aspect, the compounds of the invention reduce body weight.

In one aspect, the invention provides a MIC-1 compound of the invention for use in the prevention and/or treatment of a cardiovascular disease.

In one aspect, the invention provides a MIC-1 compound of the invention for use in the prevention and/or treatment of dyslipidaemia, arteriosclerosis, steatohepatitis, or diabetic nephropathy.

DETAILED DESCRIPTION

Figure 1:
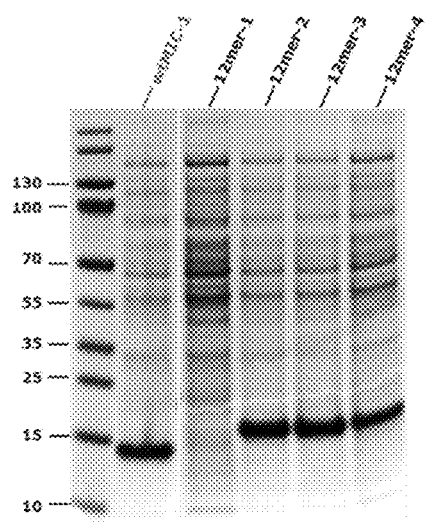
FIG. 1: The expression of MIC-1 compounds with single 12-mer building blocks. All cells were grown in TB at 37° C. and proteins were induced to express by adding 0.5 mM IPTG after OD600 reached 1.0. Cells were harvested after overnight and the expression level was checked by loading the total lysate on SDS-PAGE. wtMIC-1 was loaded as the positive control.

The invention relates to a MIC-1 compound comprising a MIC-1 polypeptide. In one aspect, the invention relates to a MIC-1 compound comprising a MIC-1 polypeptide and an N-terminal amino acid extension, wherein said extension consists of 3 to 200 amino acid residues and where the compound has a calculated pI lower than 6.5.

MIC-1

The term "MIC-1" as used herein means Macrophage Inhibitory Cytokine-1 (MIC-1), also known as Growth Differentiation Factor 15 (GDF-15), placental bone morphogenetic protein (PLAB) and nonsteroidal anti-inflammatory drug-activated gene (NAG-1). MIC-1 is synthesized as a 62 kDa intracellular homodimer precursor protein which subsequently is cleaved by a furin-like protease into a 24.5 kDa homodimer. The sequence of the full length wild type human MIC-1 is available from the UNIPROT database with accession no. Q99988. The 308 amino acid precursor sequence includes a signal peptide (amino acids 1-29), a propeptide (amino acids 30-196) and a MIC-1 monomer sequence (amino acids 197-308). The 112 amino acid MIC-1 monomer sequence is included herein as SEQ ID NO:1. MIC-1 monomer contains nine cysteine residues which give rise to the formation of 4 intrachain disulphide bonds and one interchain disulphide bond to create a covalently linked 24.5 kDa homodimer. A naturally occurring mutation corresponding to H6D in the MIC-1 monomer sequence (SEQ ID NO:1) has been described.

The term "MIC-1 compound", as used herein, refers to a compound comprising a MIC-1 polypeptide and an N-terminal amino acid extension. The MIC-1 compound is typically in the form of a homodimer.

The term "MIC-1 polypeptide" as used herein refers to the human MIC-1 monomer sequence of SEQ ID NO:1 or an analogue thereof. Numerical references to particular MIC-1 residues, if not stated otherwise, refer to the 112 amino acid monomer sequence (i.e., residue 1 is Alanine (A1), and residue 112 is Isoleucine (I112).

The term "MIC-1 analogue", or "analogue of MIC-1" as used herein refers to a MIC-1 polypeptide, which is an amino acid variant of the monomer MIC-1 sequence of SEQ ID NO:1. In other words, a MIC-1 analogue is a MIC-1 polypeptide in which a number of amino acid residues have been changed when compared to human MIC-1 (SEQ ID NO: 1). These changes may represent, independently, one or more amino acid substitutions, additions, and/or deletions.

MIC-1 analogues may be described by reference to the amino acid residue which is changed, the number of the amino acid residue (i.e. the corresponding position in the MIC-1 monomer sequence (SEQ ID NO:1)), and the change (e.g. the amino acid residue change to).

In one aspect, the MIC-1 analogue is a functional variant of the MIC-1 of SEQ ID NO:1. In one aspect of the invention, the MIC-1 analogues display at least 85%, 90% or 95% sequence identity to MIC-1 of SEQ ID NO:1. As an example of a method for determination of the sequence identity between two analogues the two peptides H6D MIC-1 and MIC-1 of SEQ ID NO:1 are aligned.

The sequence identity of the H6D MIC-1 analogue relative to MIC-1 of SEQ ID NO:1 is given by the number of aligned identical residues minus the number of different residues divided by the total number of residues in MIC-1 of SEQ ID NO:1. Accordingly, in said example the sequence identity in percentage is (112-1)/112×100. In the determination of the sequence identity of a MIC-1 analogue, the N-terminal amino acid extension is not included.

In another aspect of the invention, the MIC-1 analogues comprise less than for example less than 15, 10 or 5, amino acid modifications (substitutions, deletions, additions (including insertions) and any combination thereof) relative to human MIC-1 of SEQ ID NO:1. The term "amino acid modification" used throughout this application is used in the meaning of a modification to an amino acid as compared to monomer MIC-1 (SEQ ID NO:1). This modification can be the result of a deletion of an amino acid, addition of an amino acid, substitution of one amino acid with another or a substituent covalently attached to an amino acid of the peptide.

Substitutions: In one aspect amino acids may be substituted by conservative substitution. The term "conservative substitution" as used herein denotes that one or more amino acids are replaced by another, biologically similar residue. Examples include substitution of amino acid residues with similar characteristics, e.g. small amino acids, acidic amino acids, polar amino acids, basic amino acids, hydrophobic amino acids and aromatic amino acids.

In one aspect amino acids may be substituted by non-conservative substitution. The term "non-conservative substitution" as used herein denotes that one or more amino acids are replaced by another amino acid having different characteristics. Examples include substitution of a basic amino acid residue with an acidic amino acid residue, substitution of a polar amino acid residue with an aromatic amino acid residue, etc. In one aspect, the non-conservative substitution is substitution of a coded amino acid to another coded amino acid having different characteristics. In one aspect, the MIC-1 analogues may comprise substitutions of one or more unnatural and/or non-amino acids, e.g., amino acid mimetics, into the sequence of MIC-1.

The asparagine residue in position 3 (N3) of human MIC-1 monomer sequence (SEQ ID NO:1) is chemically labile. In one aspect of the invention, the asparagine in the position corresponding to position 3 of monomer MIC-1 sequence (SEQ ID NO:1) may be substituted to Serine (N3S), Glutamic acid (N3E), Alanine (N3A), or Glutamine (N3Q). In one aspect of the invention, the asparagine in the position corresponding to position 3 of human MIC-1 monomer sequence (SEQ ID NO:1) has been substituted to Glutamic acid (N3E).

In one aspect of the invention, the arginine in the position corresponding to position 2 of human MIC-1 monomer sequence (SEQ ID NO:1) has been substituted to alanine (R2A), and the asparagine in the position corresponding to position 3 of human MIC-1 monomer sequence (SEQ ID NO:1) has been substituted to Glutamic acid (N3E).

Deletions and Truncations: In one aspect, the MIC-1 analogues of the invention may have one or more amino acid residues deleted from the amino acid sequence of MIC-1 (SEQ ID NO:1), alone or in combination with one or more insertions or substitutions.

MIC-1 analogues with amino acid deletions may be described by "des", reference to the amino acid residue which is deleted, and followed by the number of the deleted amino acid (i.e. the corresponding position in the monomer MIC-1 (SEQ ID NO:1)). In some embodiments of the invention, the asparagine in the position corresponding to position 3 of human monomer MIC-1 (SEQ ID NO:1) is deleted (MIC-1 des-N3, SEQ ID NO:2).

MIC-1 analogues with a truncation of one or more amino acid residues at the N or C terminal may be described by "MIC-1-Δ" and reference to the number(s) of the deleted amino acid residues (i.e. the corresponding position in the monomer MIC-1 (SEQ ID NO:1)). In some embodiments of the invention, the first three residues (A1, R2, N3) at the N terminal are deleted (MIC-1-Δ1-3, SEQ ID NO:3).

Insertions: In one aspect, the MIC-1 analogues of the invention may have one or more amino acid residues inserted into the amino acid sequence of human MIC-1, alone or in combination with one or more deletions and/or substitutions.

In one aspect, the MIC-1 analogues of the invention may include insertions of one or more unnatural amino acids and/or non-amino acids into the sequence of MIC-1.

The term "protein" or "polypeptide", as e.g. used herein, refers to a compound which comprises a series of amino acids interconnected by amide (or peptide) bonds.

Amino acids are molecules containing an amine group and a carboxylic acid group, and, optionally, one or more additional groups, often referred to as a side chain.

The term "amino acid" includes coded (or proteinogenic or natural) amino acids (amongst those the 20 standard amino acids), as well as non-coded (or non-proteinogenic or non-natural) amino acids. Coded amino acids are those which are naturally incorporated into proteins. The standard amino acids are those encoded by the genetic code. Non-coded amino acids are either not found in proteins, or not produced by standard cellular machinery (e.g., they may have been subject to post-translational modification). In what follows, all amino acids of the MIC-1 proteins for which the optical isomer is not stated is to be understood to mean the L-isomer (unless otherwise specified).

As is apparent from the above, amino acid residues may be identified by their full name, their one-letter code, and/or their three-letter code. These three ways are fully equivalent. For the reader's convenience, the single and three letter amino acid codes are provided below:

Glycine: G and Gly; Proline: P and Pro; Alanine: A and Ala; Valine: V and Val; Leucine: L and Leu; Isoleucine: I and Ile; Methionine: M and Met; Cysteine: C and Cys; Phenylalanine: F and Phe; Tyrosine: Y and Tyr; Tryptophan: W and Trp; Histidine: H and His; Lysine: K and Lys; Arginine: R and Arg; Glutamine: Q and Gln; Asparagine: N and Asn; Glutamic Acid: E and Glu; Aspartic Acid: D and Asp; Serine: S and Ser; and Threonine: T and Thr.

N-Terminal Amino Acid Extension

In some embodiments of the invention the MIC-1 compound comprises an N-terminal amino acid extension.

The term "N-terminal amino acid extension" as used herein, means that the N-terminal of the MIC-1 polypeptide is attached to the C-terminal of the N-terminal amino acid extension via an amide bond, preferably a peptide bond. The terms "N-terminal amino acid extension", "N-terminal extension", and "N-extension" herein means the same thing and are used interchangeably. In one embodiment, the compound of the invention comprises human MIC-1 monomer sequence (SEQ ID NO:1) with an amino acid extension attached at the N-terminal, i.e. the Alanine at positon 1 (A1) via a peptide bond.

In some embodiments of the invention, the N-terminal amino acid extension is up to 200 amino acid residues long. In a particular embodiment of the invention the N-terminal amino acid extension has from 3 to 36 amino acid residues.

In one aspect of the invention, the N-terminal amino acid extension has a surplus of acidic amino acid residues (Aspartic acid and Glutamic acid) of at least 3, 4, 5 or 6 compared to the number of basic amino acid residues (Lysine, Arginine and Histidine). A "surplus" of acidic amino acid residues means that the number of acidic residues exceeds the number of basic residues. A defined value of the surplus of acidic amino acid residues is calculated as the number of acidic residues minus the number of basic residues.

Methionine is the initial amino acid for protein expression in prokaryotic cells (e.g. bacteria, for instance, *E. coli*). In some embodiments of the invention, the initial Methionine is removed from the protein during the protein expression. Therefore, the initial Methionine is not included in the sequence of the N-extension of MIC-1 compound. However, a person skilled in the art knows that the start codon, coding the initial Methionine, is required for the protein translation initiation and should be incorporated right in front of the nucleotide sequence for protein expression without exception.

Meanwhile, it can be understood that those MIC-1 compounds with N-extensions having the initial Methionine also fall into the scope of the invention.

Isoelectric Point (pI)

The calculated pI of a MIC-1 compound is defined as the pH at which the net calculated charge of the compound is zero. The calculated charge of the MIC-1 compound as a function of pH is obtained using the pKa values of the amino acid residues described in Table 1 and the method described by B. Skoog and A. Wichman (Trends in Analytical Chemistry, 1986, vol. 5, pp. 82-83). The side chain pKa of cysteine (Cys) is only included in the charge calculation for cysteines with a free sulfhydryl group. As an example the calculated pI value of human wtMIC-1 is 8.8 as the homodimer.

As described herein, pI calculations on MIC-1 compounds are made on MIC-1 compounds as homodimers.

TABLE 1 pKa of amino acid residues used for calculating pI. The pKa values are those described in "Correlation of Electrophoretic Mobilities from Capillary Electrophoresis with Physicochemical Properties of Proteins and Peptides by Rickard E C, Strohl M M, Nielsen R G. Analytical Biochemistry 1991, vol 197, pp 197-207".

|  | N-terminus | C-Terminus | Side chain |
|---|---|---|---|
| Asp | 8.6 | 2.75 | 3.5 |
| Asn | 7.3 | 2.75 | — |
| Thr | 8.2 | 3.2 | — |
| Ser | 7.3 | 3.2 | — |
| Glu | 8.2 | 3.2 | 4.5 |
| Gln | 7.7 | 3.2 | — |
| Pro | 9 | 3.2 | — |

TABLE 1-continued pKa of amino acid residues used for calculating pI. The pKa values are those described in "Correlation of Electrophoretic Mobilities from Capillary Electrophoresis with Physicochemical Properties of Proteins and Peptides by Rickard E C, Strohl M M, Nielsen R G. Analytical Biochemistry 1991, vol 197, pp 197-207".

|  | N-terminus | C-Terminus | Side chain |
|---|---|---|---|
| Gly | 8.2 | 3.2 | — |
| Ala | 8.2 | 3.2 | — |
| Val | 8.2 | 3.2 | — |
| Cys | 7.3 | 2.75 | 10.3 |
| Met | 9.2 | 3.2 | — |
| Ile | 8.2 | 3.2 | — |
| Leu | 8.2 | 3.2 | — |
| Tyr | 7.7 | 3.2 | 10.3 |
| Phe | 7.7 | 3.2 | — |
| Lys | 7.7 | 3.2 | 10.3 |
| His | 8.2 | 3.2 | 6.2 |
| Trp | 8.2 | 3.2 | — |
| Arg | 8.2 | 3.2 | 12.5 |

In one aspect, the MIC-1 compounds of the invention have good biophysical properties. These properties include but are not limited to solubility and/or stability.

Solubility

The human wild type MIC-1 is a hydrophobic protein, with a calculated pI 8.8 based on the homodimer. Consequently, wild type MIC-1 can only be solubilized to around 0.5 mg/ml in neutral pH aqueous buffer systems. The low solubility of MIC-1 significantly hampers its formulation properties and therapeutic use, so developing a solubility-engineered MIC-1 compound is important for MIC-1 molecular engineering.

In one aspect, the compounds of the invention have improved solubility (i.e. are more soluble) relative to human MIC-1 of SEQ ID NO:1.

As described herein, solubility is measured as described in Example 4.

In certain embodiments, the MIC-1 compounds of the invention have a solubility of at least 1 mg/ml in Tris buffer at pH 8.0. In other embodiments, the compounds of the invention have a solubility of at least 5 mg/ml, at least 10 mg/ml, at least 30 mg/ml, or at least 40 mg/ml in Tris buffer at pH 8.0.

As described herein, solubility is measured on MIC-1 compounds as homodimers.

Stability

The human wild type MIC-1 sequence is a chemically instable and several residues of the amino acid sequence could be modified during storage, including deamidation on Asparagine at position 3 (N3) and oxidation of methionines M43, M57 and M86. Chemical instability of certain residues could impact pharmaceutical properties so developing chemical stable MIC-1 compounds would be another important part of making a MIC-1 therapeutic compound.

In one aspect, the compounds of the invention have improved chemical stability relative to human MIC-1 of SEQ ID NO:1.

The term "chemical stability" refers to chemical changes in the polypeptide structure leading to formation of chemical degradation products potentially having a reduced biological activity, decreased solubility, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

MIC-1 may be chemically instable; and several residues, of the amino acid sequence (SEQ ID NO:1) could be modified during storage, including deamidation of N3 and oxidation of the methionines M43, M57 and M86. Chemical instability of certain residues could impact pharmaceutical properties like low chemical stability for MIC-1 as a therapeutic compound.

In certain embodiments of the invention, certain residues of the MIC-1 monomer sequence (SEQ ID NO:1) is modified, e.g. by substitution to increase the chemical stability of the MIC-1 compounds. To avoid deamidation, N3 could be deleted or substituted with other amino acids, e.g. E or Q. To decrease oxidation, Methionine could be substituted with other amino acids, e.g. E or L.

Crystallisation

In one aspect, the compounds of the invention are showing reduced crystal forming tendency at pH 8.0 compared with MIC-1 of SEQ ID NO:1.

Immunogenicity

In one aspect, the compounds of the invention have low immunogenicity risk.

In Vitro Activity

In one aspect, the compounds of the invention have retained MIC-1 receptor potency relative to human MIC-1 (SEQ ID NO:1). Receptor potency and efficacy can be measured in mammalian cells transfected with human MIC-1 receptor (hGFRAL, GDNF family receptor alpha like) and its signalling co-receptor hRET51 (proto-oncogene tyrosine-protein kinase receptor Ret isoform 51). MIC-1 compounds activation of the receptor complex is measured by phosphorylation of extracellular signal-regulated kinases (ERKs) as described in Example 6.

As described herein receptor potency and efficacy is measured on MIC-1 compounds as homodimers.

In Vivo Biological Activity

In one aspect the compounds of the invention are potent in vivo, which may be determined as is known in the art in any suitable animal model.

The non-obese Sprague Dawley rat is one example of a suitable animal model, and the changes in food intake may be determined in such rats in vivo, e.g. as described in Example 7. In one aspect the compounds of the invention inhibits in vivo food intake in non-obese Sprague Dawley rats. Diet-Induced Obese (DIO) Sprague Dawley rats is another example of a suitable animal model, and the changes in food intake may be determined in such rats in vivo, In one aspect the compounds of the invention inhibits in vivo food intake and lowers body weight in DIO Sprague Dawley rats.

Production Processes

MIC-1 compounds of the present invention may be produced by means of recombinant protein technology known to persons skilled in the art. In general, nucleic acid sequences encoding the proteins of interest or functional variants thereof are modified to encode the desired MIC-1 compound. This modified sequence is then inserted into an expression vector, which is in turn transformed or transfected into the expression host cells.

The nucleic acid construct encoding the MIC-1 compound may suitably be of genomic, cDNA or synthetic origin. Amino acid sequence alterations are accomplished by modification of the genetic code by well-known techniques.

The DNA sequence encoding the MIC-1 compound is usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the MIC-1 compound is operably linked to additional segments required for transcription of the DNA. The term, "operably linked" indicates that the segments are arranged so that they function in concert for their intended purposes, e.g. transcription initiates in a promoter and proceeds through the DNA sequence coding for the polypeptide until it terminates within a terminator.

Thus, expression vectors for use in expressing the MIC-1 compound will comprise a promoter capable of initiating and directing the transcription of a cloned gene or cDNA. The promoter may be any DNA sequence, which shows transcriptional activity in the host cell of choice and may be derived from genes encoding proteins either homologous or heterologous to the host cell.

Additionally, expression vectors for expression of the MIC-1 compound will also comprise a terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Expression of the MIC-1 compound can be aimed for either intracellular expression in the cytosol of the host cell or be directed into the secretory pathway for extracellular expression into the growth medium.

Intracellular expression is the default pathway and requires an expression vector with a DNA sequence comprising a promoter followed by the DNA sequence encoding the MIC-1 compound followed by a terminator.

To direct the sequence of the MIC-1 compound into the secretory pathway of the host cells, a secretory signal sequence (also known as signal peptide or a pre sequence) is needed as an extension of the MIC-1 sequence. A DNA sequence encoding the signal peptide is joined to the 5' end of the DNA sequence encoding the MIC-1 compound in the correct reading frame. The signal peptide may be that normally associated with the protein or may be from a gene encoding another secreted protein.

The procedures used to ligate the DNA sequences coding for the MIC-1 compound, the promoter, the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, New York, 1989).

The host cell into which the DNA sequence encoding the MIC-1 compound is introduced may be any cell that is capable of expressing the MIC-1 compound either intracellularly or extracellularly. The MIC-1 compound may be produced by culturing a host cell containing a DNA sequence encoding the MIC-1 compound and capable of expressing the MIC-1 compound in a suitable nutrient medium under conditions permitting the expression of the MIC-1 compound. Non-limiting examples of host cells suitable for expression of MIC-1 compounds are: Escherichia coli, Saccharomyces cerevisiae, as well as human embryonic kidney (HEK), Baby Hamster Kidney (BHK) or Chinese hamster ovary (CHO) cell lines. If posttranslational modifications are needed, suitable host cells include yeast, fungi, insects and higher eukaryotic cells such as mammalian cells.

Once the MIC-1 compound has been expressed in a host organism it may be recovered and purified to the required quality by conventional techniques. Non-limiting examples of such conventional recovery and purification techniques are centrifugation, solubilization, filtration, precipitation, ion-exchange chromatography, immobilized metal affinity chromatography (IMAC), Reversed phase—High Performance Liquid Chromatography (RP-HPLC), gel-filtration and freeze drying.

Examples of recombinant expression and purification of MIC-1 proteins may be found in e.g. Cordingley et al., J. Virol. 1989, 63, pp5037-5045; Birch et al., Protein Expr Purif., 1995, 6, pp 609-618 and in WO2008/043847. Examples of microbial expression and purification of MIC-1 proteins may be found in e.g. Chich et al, Anal. Biochem, 1995, 224, pp 245-249 and Xin et al., Protein Expr. Purif. 2002, 24, pp530-538.

Specific examples of methods of preparing a number of the compounds of the invention are included in the experimental part.

Inclusion Body and Protein Expression

MIC-1 compounds can be expressed in bacteria such as *E. coli*. In the context of the present invention, large scale protein production of said MIC-1 polypeptides with an N-extension could take of using Inclusion Bodies (IB) as this represent an advantageous approach to controlling process recovery, protein purity, protease degradation and general protein stability. This becomes particular important for large scale protein production. Of critical importance for the quality of IB is the balance of MIC-1 polypeptides with an N-extension solubility partly controlled by the calculated pI and IB formation.

MODE OF ADMINISTRATION

The term "treatment" is meant to include both the prevention and minimization of the referenced disease, disorder, or condition (i.e., "treatment" refers to both prophylactic and therapeutic administration of a compound of the invention or composition comprising a compound of the invention unless otherwise indicated or clearly contradicted by context.

The route of administration may be any route which effectively transports a compound of this invention to the desired or appropriate place in the body, such as parenterally, for example, subcutaneously, intramuscularly or intravenously. Alternatively, a compound of this invention can be administered orally, pulmonary, rectally, transdermally, buccally, sublingually, or nasally.

The amount of a compound of this invention to be administered, the determination of how frequently to administer a compound of this invention, and the election of which compound or compounds of this invention to administer, optionally together with another pharmaceutically active agent, is decided in consultation with a practitioner who is familiar with the treatment of obesity and related disorders.

PHARMACEUTICAL COMPOSITIONS

Pharmaceutical compositions comprising a compound of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. $19^{th}$ edition (1995), and any later editions).

Combination Treatment

The treatment with a compound according to the present invention may also be combined with one or more pharmacologically active substances, e.g., selected from antiobesity agents, appetite regulating agents, and agents for the treatment and/or prevention of complications and disorders resulting from or associated with obesity.

Pharmaceutical Indications

In one aspect, the present invention relates to a compound of the invention, for use as a medicament.

In particular embodiments, the compound of the invention may be used for the following medical treatments:
(i) Prevention and/or treatment of eating disorders, such as obesity, e.g. by decreasing food intake, reducing body weight, suppressing appetite and inducing satiety.
(ii) Prevention and/or treatment of hyperglycemia, insulin resistance and/or impaired glucose tolerance.
(iii) Prevention and/or treatment of dyslipidaemia.

In some embodiments the invention relates to a method for weight management. In some embodiments the invention relates to a method for reduction of appetite. In some embodiments the invention relates to a method for reduction of food intake.

Generally, all subjects suffering from obesity are also considered to be suffering from overweight. In some embodiments the invention relates to a method for treatment or prevention of obesity. In some embodiments the invention relates to use of the MIC-1 compounds of the invention for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/height in meters$^2$. A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the MIC-1 compounds of the invention for treatment or prevention of overweight, optionally in the presence of at least one weight-related comorbidity.

In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the MIC-1 compounds of the invention for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

In some embodiments the invention relates to a method for treatment or prevention of cardiovascular diseases like arteriosclerosis and other disorders such as steatohepatitis, and diabetic nephropathy.

The articles "a" and "an" are used herein to refer to one or to more than one (i.e., to at least one) of the grammatical object of the article. By way of example, "a MIC-1 polypeptide" means one MIC-1 polypeptide or more than one MIC-1 polypeptide.

Particular Embodiments

The invention is further described by the following non-limiting embodiments of the invention:

1. A MIC-1 compound comprising a MIC-1 polypeptide and an N-terminal amino acid extension, wherein said extension consists of 3 to 200 amino acid residues and wherein the compound has a calculated pI lower than 6.5.
2. Compound according to embodiment 1, wherein the MIC-1 polypeptide and the amino acid extension consists of between 109-312, 112-312, 115-312, 112-148 or 115-148 amino acid residues.
3. Compound according to embodiment 1, wherein the compound is a homodimer.
4. Compound according to embodiment 1, wherein the compound as a homodimer consists of between 218-296, 224-296, 230-296, 218-310, 224-310, 230-310, 218-360, 224-360, 230-360, 218-624, 224-624, 230-296 or 230-296 amino acid residues.
5. Compound consisting of a MIC-1 polypeptide with an N-terminal amino acid extension, wherein said extension consists of 3 to 200 amino acid residues and where the compound has a calculated pI lower than 6.5.
6. Compound according to embodiments 1-5, wherein the calculated pI is lower than 6.1.
7. Compound according to embodiments 1-5, wherein the calculated pI is lower than 6.0.
8. Compound according to any one of embodiments 1-5, wherein the calculated pI is lower than 6.4, 6.3, 6.2, 6.1, 6.0, 5.9, 5.8, 5.7, 5.6, 5.5, 5.4, 5.3, or 5.2, 5.1, or 5.0, 4.9, 4.8, 4.7, 4.6, 4.5, 4.4, 4.3, 4.2, 4.1 or 4.0.
9. Compound according to any one of embodiments 1-7, wherein the calculated pI is higher than 4.7.
10. Compound according to any one of embodiments 1-7, wherein the calculated pI is higher than 4.8.
11. Compound according to any one of embodiments 1-7, wherein the calculated pI is higher than 4.9.
12. Compound according to any one of embodiments 1-7, wherein the calculated pI is higher than 5.0.
13. Compound according to any one of embodiments 1-7, wherein the calculated pI is higher than 5.1.
14. Compound according to any one of embodiments 1-5, wherein the calculated pI is in the range of 6.5-3.0, 6.5-3.5, 6.5-4.0, 6.1-3.0, 6.1-3.5, 6.1-4.0, 6.1-4.7, 6.1-4.9, 6.1-5.0, 6.1-5.1, 6.0-3.0, 6.0-3.5, 6.0-4.0, 5.9-3.0, 5.9-3.5, 5.9-4.0, 5.9-5.0, 5.9-5.1, 5.8-3.0, 5.8-3.5, 5.8-4.0, 5.8-5.1, 5.8-5.2, 5.5-3.0, 5.5-3.5, 5.5-4.0, or 5.0-4.0.
15. Compound according to any one of embodiments 1-14, wherein the calculated pI is in the range of 5.8-5.2.
16. Compound according to any of the preceding embodiments, wherein said extension is in the range of 3-100, 3-50, 3-40, 3-30, 5-100, 5-50, 5-40, 5-30, 10-100, 10-50, 10-40, 10-30, 3-36, 3-30, 3-25, 3-24, 3-12, 4-36, 4-30, 4-24, 4-12, 5-36, 5-30, 5-24, 5-12, 6-36, 6-30, 6-24, 6-12, 7-36, 7-30, 7-24, 7-12, 8-36, 8-30, 8-24, 8-12, 30-36, 32-36, 30-34, or 30-32 amino acid residues in length.
17. Compound according to any of the preceding embodiments, wherein said extension is 3 to 36 amino acids in length.
18. Compound according to any of the preceding embodiments, wherein said extension is in the range of 30-32 amino acid residues in length.
19. Compound according to any of the preceding embodiments, wherein the extension has a surplus of acidic amino acid residues (Aspartic acid or Glutamic acid) of at least 3, 4, 5, 6, 7, 8, 9 or 10 compared to the number of basic amino acid residues (Lysine, Arginine or Histidine).
20. Compound according to any one of embodiments 1-18, wherein the extension comprise at least 15%, 20%, 25%, 30%, 40%, 50%, 60%, 70% or 75% surplus of acidic amino acid residues (Aspartic acid or Glutamic acid) compared to number of basic amino acid residues (Lysine or Arginine or Histidine).
21. Compound according to any of the preceding embodiments, wherein the extension comprise at least 15% acidic amino acid residues.
22. Compound according to embodiment 21, wherein the extension comprise at least 25% acidic amino acid residues.
23. Compound according to any of the preceding embodiments, wherein the extension is composed of amino acid residues selected among the group consisting of A, E, G, P, S, T, D, N, and Q wherein said extension comprises at least three E and/or D amino acid residues.
24. Compound according to any of the preceding embodiments, wherein the extension is composed of amino acid residues selected among the group consisting of A, E, G, P, S, T, Q and D, wherein said extension comprises at least three E and/or D amino acid residues.
25. Compound according to embodiment 23 or 24, wherein the extension comprises at least three E and at least one P.
26. Compound according to embodiment 25, wherein the extension further comprises S, G, T and A.
27. Compound according to embodiment 26, wherein the extension comprises 6 Ser, 4 Pro, 4 Gly, 4 Thr, 4 Glu and 2 Ala.
28. Compound according to embodiment 27, wherein the extension comprises two of sequences selected from the group consisting of SPAGSPTSTEEG (SEQ ID NO: 166), TSESATPESGPG (SEQ ID NO: 167), TSTEPSEGSAPG (SEQ ID NO: 168) and SEPATSGSETPG (SEQ ID NO: 169).
29. Compound according to embodiment 28, wherein the extension further comprises 6-8 consecutive amino acids of SPAGSPTSTEEG (SEQ ID NO: 166), TSESATPESGPG (SEQ ID NO: 167), TSTEPSEGSAPG (SEQ ID NO: 168) or SEPATSG- SETPG (SEQ ID NO: 169), such as the first 6-8 amino acid residues, the last 6-8 residues or the internal 6-8 residues.
30. Compound according to any one of embodiments 23 to 29, wherein the extension starts with S.
31. Compound according to any one of embodiments 30, wherein the extension starts with SE.
32. Compound according to any one of embodiments 31, wherein the extension starts with SEP.
33. Compound according to any one of embodiments 1 to 24, wherein the extension comprises one or more of the following sequences SPAGSP (SEQ ID NO:4), TSESAT (SEQ ID NO:5), TSTEPE (SEQ ID NO:6), SEPATS (SEQ ID NO:7), TSTEEG (SEQ ID NO:8), PESGPG (SEQ ID NO:9), SGSAPG (SEQ ID NO:10), GSETPG (SEQ ID NO:11), SEPATSGSETPGSPAGSPTSTEEG (SEQ ID NO:12), SEPATSGSETPGTSESATPESGPG (SEQ ID NO:13), SEPATSGSETPGTSTEPESGSAPG (SEQ ID NO:14), SEPATSGSETPGSPAGSPTSTEEGSPAGSP (SEQ ID NO:15), SEPATSGSETPGTSESATPESGPGSPAGSP (SEQ ID NO:16), SEPATSGSETPGTSTEPESGSAPGSPAGSP (SEQ ID NO:17), SEPATSGSETPGSPAGSPTSTEEGTSESAT (SEQ ID NO:18), SEPATSGSETPGTSESATPESGPGTSESAT (SEQ ID NO:19), SEPATSGSETPGTSTEPESGSAPGTSESAT (SEQ ID NO:20), SEPATSGSETPGSPAGSPTSTEEGTSTEPE (SEQ ID NO:21), SEPATSGSETPGTSESATPESGPGTSTEPE (SEQ ID NO:22), SEPATSGSETPGTSTEPESGSAPGTSTEPE (SEQ ID NO:23), SEPATSGSETPGSPAGSPTSTEEGSEPATS (SEQ ID NO:24), SEPATSGSETPGTSESATPESGPGSEPATS (SEQ ID NO:25), SEPATSGSETPGTSTEPESGSAPGSEPATS (SEQ ID NO:26), SEPATSGSETPGSPAGSPTSTEEGTSTEEG (SEQ ID NO:27), SEPATSGSETPGTSESATPESGPGTSTEEG (SEQ ID NO:28), SEPATSGSETPGTSTEPESGSAPGTSTEEG (SEQ ID NO:29), SEPATSGSETPGSPAGSPTSTEEGPESGPG (SEQ ID NO:30), SEPATSGSETPGTSESATPESGPGPESGPG (SEQ ID NO:31), SEPATSGSETPGTSTEPESGSAPGPESGPG (SEQ ID NO:32), SEPATSGSETPGSPAGSPTSTEEGSGSAPG (SEQ ID NO:33), SEPATSGSETPGTSESATPESGPGSGSAPG (SEQ ID NO:34), SEPATSGSETPGTSTEPESGSAPGSGSAPG (SEQ ID NO:35), SEPATSGSETPGSPAGSPTSTEEGGSETPG (SEQ ID NO:36), SEPATSGSETPGTSESATPESGPGGSETPG (SEQ ID NO:37), SEPATSGSETPGTSTEPESGSAPGGSETPG (SEQ ID NO:38), SEPATSGSETPGTSESATPESGPGTSTEPS (SEQ ID NO:70), SEPATSGSETPGTSESATPESGPGTSTEPSEG (SEQ ID NO:71), SEPATSGSETPGSPAGSPTSTEEGTSESATPESGPG (SEQ ID NO:39), SEPATSGSETPGSPAGSPTSTEEGSPAGSPTSTEEG (SEQ ID NO:40), SEPATSGSETPGSPAGSPTSTEEGTSTEPESGSAPG (SEQ ID NO:41), SEPATSGSETPGTSESATPESGPGSPAGSPTSTEEG (SEQ ID NO:42), SEPATSGSETPGTSESATPESGPGTSESATPESGPG (SEQ ID NO:43), SEPATSGSETPGTSESATPESGPGTSTEPESGSAPG (SEQ ID NO:44), SEPATSGSETPGTSESATPESGPGSEPATSGSETPG (SEQ ID NO:45), SEPATSGSETPGTSTEPESGSAPGSPAGSPTSTEEG (SEQ ID NO:46), SEPATSGSETPGTSTEPESGSAPGTSESATPESGPG (SEQ ID NO:47), SEPATSGSETPGTSTEPESGSAPGTSTEPESGSAPG (SEQ ID NO:48), SEPATSGSETPGTSTEPESGSAPGSEPATSGSETPG (SEQ ID NO:49), SEPATSGSETPGSEPATSGSETPGSPAGSPTSTEEG (SEQ ID NO:50), SEPATSGSETPGSEPATSGSETPGTSESATPESGPG (SEQ ID NO:51), SEPATSGSETPGSEPATSGSETPGTSTEPESGSAPG (SEQ ID NO:52), SEPATSGSETPGSEPATSGSETPGSEPATSGSETPG (SEQ ID NO:53), GEPS (SEQ ID NO:118), GPSE (SEQ ID NO:119), GPES (SEQ ID NO:120), GSPE (SEQ ID NO:121), GSEP (SEQ ID NO:122), GEPQ (SEQ ID NO:123), GEQP (SEQ ID NO:124), GPEQ (SEQ ID NO:125), GPQE (SEQ ID NO:126), GQEP (SEQ ID NO:127) or GQPE (SEQ ID NO:128), PEDEETPEQE (SEQ ID NO:129), PDEGTEEETE (SEQ ID NO:130), PAAEEEDDPD (SEQ ID NO:131), AEPDEDPQSED (SEQ ID NO:132), AEPDEDPQSE (SEQ ID NO:133), AEPEEQEED (SEQ ID NO:134), AEPEEQEE (SEQ ID NO:135), GGGS (SEQ ID NO:136), GSGS (SEQ ID NO:137), GGSS (SEQ ID NO:138) and SSSG (SEQ ID NO:139).
34. Compound according to any one of embodiments 1 to 24, wherein the extension comprises one or more of the following sequences SPAGSP (SEQ ID NO:4), TSESAT (SEQ ID NO:5), TSTEPE (SEQ ID NO:6), SEPATS (SEQ ID NO:7), TSTEEG (SEQ ID NO:8), PESGPG (SEQ ID NO:9), SGSAPG (SEQ ID NO:10), GSETPG (SEQ ID NO:11), SEPATSGSETPGSPAGSPTSTEEG (SEQ ID NO:12), SEPATSGSETPGTSESATPESGPG (SEQ ID NO:13), SEPATSGSETPGTSTEPESGSAPG (SEQ ID NO:14), SEPATSGSETPGSPAGSPTSTEEGSPAGSP (SEQ ID NO:15), SEPATSGSETPGTSESATPESGPGSPAGSP (SEQ ID NO:16), SEPATSGSETPGTSTEPESGSAPGSPAGSP (SEQ ID NO:17), SEPATSGSETPGSPAGSPTSTEEGTSESAT (SEQ ID NO:18), SEPATSGSETPGTSESATPESGPGTSESAT (SEQ ID NO:19), SEPATSGSETPGTSTEPESGSAPGTSESAT (SEQ ID NO:20), SEPATSGSETPGSPAGSPTSTEEGTSTEPE (SEQ ID NO:21), SEPATSGSETPGTSESATPESGPGTSTEPE (SEQ ID NO:22), SEPATSGSETPGTSTEPESGSAPGTSTEPE (SEQ ID NO:23), SEPATSGSETPGSPAGSPTSTEEGSEPATS (SEQ ID NO:24), SEPATSGSETPGTSESATPESGPGSEPATS (SEQ ID NO:25), SEPATSGSETPGTSTEPESGSAPGSEPATS (SEQ ID NO:26), SEPATSGSETPGSPAGSPTSTEEGTSTEEG (SEQ ID NO:27), SEPATSGSETPGTSESATPESGPGTSTEEG (SEQ ID NO:28), SEPATSGSETPGTSTEPESGSAPGTSTEEG (SEQ ID NO:29), SEPATSGSETPGSPAGSPTSTEEGPESGPG (SEQ ID NO:30), SEPATSGSETPGTSESATPESGPGPESGPG (SEQ ID NO:31), SEPATSGSETPGTSTEPESGSAPGPESGPG (SEQ ID NO:32), SEPATSGSETPGSPAGSPTSTEEGSGSAPG (SEQ ID NO:33), SEPATSGSETPGTSESATPESGPGSGSAPG (SEQ ID NO:34), SEPATSGSETPGTSTEPESGSAPGSGSAPG (SEQ ID NO:35), SEPATSGSETPGSPAGSPTSTEEGGSETPG (SEQ ID NO:36), SEPATSGSETPGTSESATPESGPGGSETPG (SEQ ID NO:37), SEPATSGSETPGTSTEPESGSAPGGSETPG (SEQ ID NO:38), SEPATSGSETPGSPAGSPTSTEEGTSESATPESGPG (SEQ ID NO:39), SEPATSGSETPGSPAGSPTSTEEGSPAGSPTSTEEG, (SEQ ID NO:40) SEPATSGSETPGSPAGSPTSTEEGTSTEPESGSAPG, (SEQ ID NO:41) SEPATSGSETPGTSESATPESGPGSPAGSPTSTEEG, (SEQ ID NO:42) SEPATSGSETPGTSESATPESGPGTSESATPESGPG, (SEQ ID NO:43) SEPATSGSETPGTSESAT-PESGPGTSTEPESGSAPG, (SEQ ID NO:44) SEPATSGSETPGTSESATPESGPGSEPATSGSETPG, (SEQ ID NO:45) SEPATSGSETPGTSTE-PESGSAPGSPAGSPTSTEEG, (SEQ ID NO:46) SEPATSGSETPGTSTEPESGSAPGTSESAT-PESGPG, (SEQ ID NO:47) SEPATSGSETPGTSTE-PESGSAPGTSTEPESGSAPG, (SEQ ID NO:48) SEPATSGSETPGTSTEPESGSAPGSEPATSG-SETPG, (SEQ ID NO:49) SEPATSG-SETPGSEPATSGSETPGSPAGSPTSTEEG, (SEQ ID NO:50) SEPATSGSETPGSEPATSGSETPGTSESAT-PESGPG, (SEQ ID NO:51) SEPATSG-SETPGSEPATSGSETPGTSTEPESGSAPG, (SEQ ID NO:52) SEPATSGSETPGSEPATSG-SETPGSEPATSGSETPG (SEQ ID NO:53), GEPQ (SEQ ID NO:123), GEPS (SEQ ID NO:118), GGGS (SEQ ID NO:136), GSGS (SEQ ID NO:137), GGSS (SEQ ID NO:138), and SSSG (SEQ ID NO:139).

35. Compound according to any one of embodiments 1-24, wherein the extension comprises any combination of any 2-6 of the following sequences SPAGSP (SEQ ID NO:4), TSESAT (SEQ ID NO:5), TSTEPE (SEQ ID NO:6), SEPATS (SEQ ID NO:7), TSTEEG (SEQ ID NO:8), PESGPG (SEQ ID NO:9), SGSAPG (SEQ ID NO:10), GSETPG (SEQ ID NO:11), GEPQ (SEQ ID NO:123), GEPS (SEQ ID NO:118), GGGS (SEQ ID NO:136), GSGS (SEQ ID NO:137), GGSS (SEQ ID NO:138), and SSSG (SEQ ID NO:139).

36. Compound according to any one of embodiments 1-24, wherein the extension comprises one or more of the following sequences GEPS (SEQ ID NO:118), GPSE (SEQ ID NO:119), GPES (SEQ ID NO:120), GSPE (SEQ ID NO:121), GSEP (SEQ ID NO:122), GEPQ (SEQ ID NO:123), GEQP (SEQ ID NO:124), GPEQ (SEQ ID NO:125), GPQE (SEQ ID NO:126), GQEP (SEQ ID NO:127), GQPE (SEQ ID NO:128), GGGS (SEQ ID NO:136), GSGS (SEQ ID NO:137), GGSS (SEQ ID NO:138), and SSSG (SEQ ID NO:139).

37. Compound according to embodiment 36, wherein the extension comprises any combination of 2-9 of the following sequences GEPS (SEQ ID NO:118), GPSE (SEQ ID NO:119), GPES (SEQ ID NO:120), GSPE (SEQ ID NO:121), GSEP (SEQ ID NO:122), GEPQ (SEQ ID NO:123), GEQP (SEQ ID NO:124), GPEQ (SEQ ID NO:125), GPQE (SEQ ID NO:126), GQEP (SEQ ID NO:127), GQPE (SEQ ID NO:128), GGGS (SEQ ID NO:136), GSGS (SEQ ID NO:137), GGSS (SEQ ID NO:138), and SSSG (SEQ ID NO:139).

38. Compound according to any one of embodiments 1-24, wherein the extension comprises one or more of the following sequences GEPS (SEQ ID NO:118), GPSE (SEQ ID NO:119), GPES (SEQ ID NO:120), GSPE (SEQ ID NO:121), GSEP (SEQ ID NO:122), GGGS (SEQ ID NO:136), GSGS (SEQ ID NO:137), GGSS (SEQ ID NO:138), and SSSG (SEQ ID NO:139).

39. Compound according to embodiment 38, wherein the extension comprises any combination of 2-9 of the following sequences GEPS (SEQ ID NO:118), GPSE (SEQ ID NO:119), GPES (SEQ ID NO:120), GSPE (SEQ ID NO:121), GSEP (SEQ ID NO:122), GGGS (SEQ ID NO:136), GSGS (SEQ ID NO:137), GGSS (SEQ ID NO:138), and SSSG (SEQ ID NO:139).

40. Compound according to embodiment 39, wherein the extension comprises one or more of the following sequences GEPSGEPSGEPSGEPSGEPS (SEQ ID NO:140), GPSEGPSEGPSEGPSEGPSE (SEQ ID NO:141), GPESGPESGPESGPESGPES (SEQ ID NO:142), GSPEGSPEGSPEGSPEGSPE (SEQ ID NO:143), and GSEPGSEPGSEPGSEPGSEP (SEQ ID NO:144).

41. Compound according to any one of embodiments 1-24, wherein the extension comprises one or more of the following sequences GEPQ (SEQ ID NO:123), GEQP (SEQ ID NO:124), GPEQ (SEQ ID NO:125), GPQE (SEQ ID NO:126), GQEP (SEQ ID NO:127), GQPE (SEQ ID NO:128), GGGS (SEQ ID NO:136), GSGS (SEQ ID NO:137), GGSS (SEQ ID NO:138), and SSSG (SEQ ID NO:139).

42. Compound according to embodiment 41, wherein the extension comprises any combination of 2-9 of the following sequences GEPQ (SEQ ID NO:123), GEQP (SEQ ID NO:124), GPEQ (SEQ ID NO:125), GPQE (SEQ ID NO:126), GQEP (SEQ ID NO:127), GQPE (SEQ ID NO:128), GGGS (SEQ ID NO:136), GSGS (SEQ ID NO:137), GGSS (SEQ ID NO:138), and SSSG (SEQ ID NO:139).

43. Compound according to embodiment 42, wherein the extension comprises one or more of the following sequences GEPQGEPQGEPQGEPQGEPQ (SEQ ID NO:145), GEQPGEQPGEQPGEQPGEQP (SEQ ID NO:146), GPEQGPEQGPEQGPEQGPEQ(SEQ ID NO:147), GPQEGPQEGPQEGPQEGPQE (SEQ ID NO:148), GQEPGQEPGQEPGQEPGQEP (SEQ ID NO:149), and GQPEGQPEGQPEGQPEGQPE (SEQ ID NO:150).

44. Compound according to any of the embodiments 1-24, wherein the extension comprises one or more of the following sequences PEDEETPEQE (SEQ ID NO:129), PDEGTEEETE (SEQ ID NO:130), PAAEEEDDPD (SEQ ID NO:131), AEPDEDPQSED (SEQ ID NO:132), AEPDEDPQSE (SEQ ID NO:133), AEPEEQEED (SEQ ID NO:134), and AEPEEQEE (SEQ ID NO:135), GGGS (SEQ ID NO:136), GSGS (SEQ ID NO:137), GGSS (SEQ ID NO:138) and SSSG (SEQ ID NO:139).

45. Compound according to any of the embodiments 1-24, wherein the extension comprises any combination of two to three of the following sequences PEDEETPEQE (SEQ ID NO:129), PDEGTEEETE (SEQ ID NO:130), PAAEEEDDPD (SEQ ID NO:131), AEPDEDPQSED (SEQ ID NO:132), AEPDEDPQSE (SEQ ID NO:133), AEPEEQEED (SEQ ID NO:134), AEPEEQEE (SEQ ID NO:135) and AEEAEEAEEAEEAEE (SEQ ID NO:151).

46. Compound according to any of the embodiments 1-24, wherein the extension comprises one or more of the following sequences SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:161, SEQ ID NO:162, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194 and SEQ ID NO:195.

47. Compound according to any one of preceding embodiments, wherein the extension comprises 1-3 alanine amino acid residues N-terminally.
48. Compound according to any one of preceding embodiments, wherein the extension comprises 1-4 Glycine and Serine amino acid residues C-terminally.
49. Compound according to any one of preceding embodiments, wherein the extension comprises a (Gly-Ser)n or a (Ser-Gly)n sequence C-terminally, wherein n is an integer between 1-8.
50. Compound according to any one of preceding embodiments, wherein the extension comprises GGGS (SEQ ID NO:136), GSGS (SEQ ID NO:137), GGSS (SEQ ID NO:138) or SSSG (SEQ ID NO:139) C-terminally.
51. Compound according to any of the preceding embodiments, wherein the MIC-1 polypeptide displays at least 80%, 85%, 90%, 91%, 92%, 93%, 94%, 95%, 96%, 97%, 98% or 99% sequence identity to wild type MIC-1 (SEQ ID NO:1).
52. Compound according to embodiment 51, wherein the MIC-1 polypeptide displays at least 95% sequence identity to wild type MIC-1 (SEQ ID NO:1).
53. Compound according to any one of embodiments 1-51, wherein the MIC-1 polypeptide has a maximum of 10, 9, 8, 7, 6, 5, 4, 3, 2 or 1 amino acid modifications compared to MIC-1 of SEQ ID NO:1.
54. Compound according to any one of embodiments 1-53, wherein the MIC-1 polypeptide has a maximum of 7, 6, 5, 4, 3 or 2 amino acid modifications compared to MIC-1 of SEQ ID NO:1.
55. A compound comprising a MIC-1 polypeptide, wherein said compound has a calculated pI lower than 6.5.
56. Compound according to any one of the preceding embodiments wherein the MIC-1 polypeptide comprises one or more of the following substitutions P11E, H18E, R21E, A30E, M43L, M43E, A47E, R53E, A54E, M57E, M57L, H66E, R67E, L68E, K69E, A75E, A81E, P85E, M86F, M86L, Q90E, T92E, L105E, K107E compared to wild type MIC-1 (SEQ ID NO:1).
57. Compound according to any one of the preceding embodiments wherein the MIC-1 polypeptide comprises one or more of the following substitutions R2S, R2A, N3S N3E, N3A, N3T, N3P, N3G, N3V, N3H, N3Y or N3Q compared to MIC-1 of SEQ ID NO:1.
58. Compound according to any one of the preceding embodiments wherein the MIC-1 polypeptide comprises a deletion of N3 (des-N3) compared to MIC-1 of SEQ ID NO:1.
59. Compound according to any one of the preceding embodiments wherein the MIC-1 polypeptide comprises a M57E or M57L substitution compared to MIC-1 of SEQ ID NO:1.
60. Compound according to any one of the preceding embodiments wherein the MIC-1 polypeptide comprises a M86L or M86F substitution compared to MIC-1 of SEQ ID NO:1.
61. Compound according to embodiment 60 wherein the MIC-1 polypeptide further comprises a Q90E or T92E substitution compared to MIC-1 of SEQ ID NO:1.
62. Compound according to any one of the preceding embodiments wherein the MIC-1 polypeptide comprises a H66E substitution compared to MIC-1 of SEQ ID NO:1.
63. Compound according to any one of the preceding embodiments wherein the MIC-1 polypeptide comprises a R67E substitution compared to MIC-1 of SEQ ID NO:1.
64. Compound according to any one of the preceding embodiments wherein the MIC-1 polypeptide comprises a deletion of the first 3, 4, 5 or 6 residues compared to MIC-1 of SEQ ID NO:1.
65. Compound according to any one of the preceding embodiments wherein the MIC-1 polypeptide comprises a deletion of the first 3 residues compared to MIC-1 of SEQ ID NO:1.
66. Compound according to any one of embodiments 1-56, wherein the MIC-1 polypeptide has a sequence according to SEQ ID NO:154 (M43L/des-N3).
67. Compound according to any one of embodiments 1-56, wherein the MIC-1 polypeptide has a sequence according to SEQ ID NO:155 (M43L/Δ1-3).
68. Compound according to any one of embodiments 1-56, wherein the MIC-1 polypeptide has a sequence according to SEQ ID NO:156 (M57E/H66E/des-N3).
69. Compound according to any one of embodiments 1-56, wherein the MIC-1 polypeptide has a sequence according to SEQ ID NO:157 (M57L/Δ1-3).
70. Compound according to any one of embodiments 1-56, wherein the MIC-1 polypeptide has a sequence according to SEQ ID NO:158 (M57L/des-N3).
71. Compound according to any one of embodiments 1-56, wherein the MIC-1 polypeptide has a according to SEQ ID NO:159 (M86L/Δ1-3).
72. Compound according to any one of embodiments 1-56, wherein the MIC-1 polypeptide has a sequence according to SEQ ID NO:160 (M86L/des-N3).
73. Compound according to any one of embodiments 1-56, wherein the MIC-1 polypeptide has a sequence according to SEQ ID NO:222 (M57L, M86L/des-N3).
74. Compound according to any one of embodiments 1-55, wherein the MIC-1 polypeptide has a sequence according to SEQ ID NO:1.
75. A MIC-1 compound comprising a MIC-1 polypeptide and an N-terminal amino acid extension, wherein the compound comprises an amino acid sequence according to SEQ ID NO: 89, 90, 91, 92, 93, 94, 95, 96, 97, 98, 99, 100, 101, 102, 103, 104, 105, 106, 107, 108, 109, 110, 111, 112, 113, 114, 115, 116, 117 or 164.
76. A MIC-1 compound comprising a MIC-1 polypeptide and an N-terminal amino acid extension, wherein the compound comprises an amino acid sequence according to SEQ ID NO: 100, 104, 106, 107, 108, 109, 111, 112, 113, 114, 115, 116, 117 or 164.
77. Compound according to any one of the preceding embodiments, showing improved solubility compared with MIC-1 of SEQ ID NO:1.
78. Compound according to any one of the preceding embodiments, showing improved solubility compared with MIC-1 of SEQ ID NO:1 at pH 8.0 in a Tris buffer system.
79. Compound according to any one of embodiments 1-78, wherein the compound has more than a 2-fold, 5-fold, 10-fold, 50-fold up to 100-fold improvement in solubility compared with MIC-1 of SEQ ID NO:1 at pH 8.0 in a Tris buffer system.
80. Compound according to any one of embodiments 1-79, wherein the compound has a solubility of 0.5, 1.0, 5.0, 10, 30 or 50 mg/ml at pH 8.0 in a Tris buffer system.

81. Compound according to embodiment 80, wherein the compound has a solubility of 30 mg/ml at pH 8.0 in a Tris buffer system.
82. Compound according to any one of the preceding embodiments wherein the MIC-1 compound is showing reduced crystal forming tendency at pH 8.0 compared with MIC-1 of SEQ ID NO:1.
83. Compound according to embodiment 82, wherein the crystal forming tendency is measured at pH 8.0 in a Tris buffer system.
84. Compound according to any of the preceding embodiments, wherein the compound has low immunogenicity risk.
85. Compound according to any of the preceding embodiments, wherein the compound has improved in vivo efficacy on lowering food intake and/or lowering body weight compared with MIC-1 of SEQ ID NO:1.
86. A compound according to any one of embodiments 1-85 for use as a medicament.
87. A compound according to any one of embodiments 1-85 for use in the prevention and/or treatment of a metabolic disorder.
88. A compound according to embodiment 87 for use in the prevention and/or treatment of a metabolic disorder, wherein the metabolic disorder is obesity, type 2 diabetes, dyslipidemia, or diabetic nephropathy.
89. A compound according to any one of embodiments 1-85 for use in the prevention and/or treatment of eating disorders, such as obesity.
90. A compound according to embodiment 89 for use in the prevention and/or treatment of obesity by decreasing food intake, reducing body weight, suppressing appetite and/or inducing satiety.
91. A compound according to any one of embodiments 1-85 for use in the prevention and/or treatment of a cardiovascular disease.
92. A compound according to embodiment 91 for use in the prevention and/or treatment of dyslipidaemia, arteriosclerosis, steatohepatitis, or diabetic nephropathy.
93. A pharmaceutical composition comprising a compound according to any one of embodiments 1-85 or a pharmaceutically acceptable salt, amide or ester thereof, and one or more pharmaceutically acceptable excipients.
94. The use of a compound according to any one of embodiments 1-85 in the manufacture of a medicament for the prevention and/or treatment of a metabolic disorder, wherein the metabolic disorder is obesity, type 2 diabetes, dyslipidemia, or diabetic nephropathy.
95. The use of a compound according to any one of embodiments 1-85 in the manufacture of a medicament for the prevention and/or treatment of eating disorders.
96. The use of a compound according to any one of embodiments 1-85 in the manufacture of a medicament for the prevention and/or treatment of obesity.
97. The use of a compound according to any one of embodiments 1-85 in the manufacture of a medicament for the prevention and/or treatment of obesity by decreasing food intake, reducing body weight, suppressing appetite and/or inducing satiety.
98. The use of a compound according to any one of embodiments 1-85 in the manufacture of a medicament for the prevention and/or treatment of a cardiovascular disease.
99. The use of a compound according to any one of embodiments 1-85 in the manufacture of a medicament for the prevention and/or treatment of dyslipidaemia, arteriosclerosis, steatohepatitis, or diabetic nephropathy.
100. A method of treating and/or preventing a metabolic disorder by administering a pharmaceutically active amount of a compound according to any one of embodiments 1-85, wherein the metabolic disorder is obesity, type 2 diabetes, dyslipidemia, or diabetic nephropathy.
101. A method of treating and/or preventing eating disorders by administering a pharmaceutically active amount of a compound according to any one of embodiments 1-85.
102. A method of treating and/or preventing obesity by administering a pharmaceutically active amount of a compound according to any one of embodiments 1-85.
103. A method of treating and/or preventing obesity by decreasing food intake, reducing body weight, suppressing appetite and/or inducing satiety by administering a pharmaceutically active amount of a compound according to any one of embodiments 1-85.
104. A method of treating and/or preventing a cardiovascular disease by administering a pharmaceutically active amount of a compound according to any one of embodiments 1-85.
105. A method of treating and/or preventing dyslipidaemia, arteriosclerosis, steatohepatitis, or diabetic nephropathy by administering a pharmaceutically active amount of a compound according to any one of embodiments 1-85.
106. A polynucleotide molecule encoding a compound according to any one of embodiments 1-85.

EXAMPLES

List of Abbreviations

"Main peak" refers to the peak in a purification chromatogram which has the highest UV intensity in milliabsorbance units and which contains the fusion protein.

HPLC is High performance liquid chromatography.

SDS-PAGE is Sodium dodecyl sulfate Polyacrylamide gel electrophoresis.

IMAC is immobilized metal affinity chromatography.

SEC is size exclusion chromatography.

MS is mass spectrometry.

In this description, Greek letters may be represented by their symbol or the corresponding written name, for example: α=alpha; β=beta; ε=epsilon; γ=gamma; ω=omega; Δ=delta; etc. Also, the Greek letter of µ may be represented by "u", e.g. in µl=ul, or in µM=uM.

Design of MIC-1 Compounds

In an aspect of the invention, MIC-1 compounds were designed to have increased solubility. In an aspect of the invention, this was achieved by adding an N-terminal "acidic" extension to the MIC-1 polypeptide. In an aspect of the invention, solubility were enhanced and stability improved by modification of the amino acid sequence of the MIC-1 polypeptide. For example extensions were added to the N terminal of a MIC-1 polypeptide, and/or modification was done within the amino acid sequence of the MIC-1 polypeptide (in-sequence mutation).

N-Extension Design:

In the design of the N-terminal amino acid_extension, F, I, L, M, V, W and Y were excluded, since they could contribute to protein aggregation. H, K, and R were also excluded, since they could cause undesired binding on cell membrane. A, E, G, P, S, T, D, N, and Q are preferred for the N-extension sequence. E and D are particularly preferred since they increase the solubility by decreasing pI value of the compound. Particularly, for some N-extensions, one or two additional Alanine(s) were added at the very N-terminal to increase the initial Methionine removing efficiency when MIC-1 compounds were expressed in *E. coli*.

Various N-terminal amino acid_extensions were designed based on the above principles. Some N-extensions comprise sequences originating from human proteins (humanized sequences); some comprise artificially designed sequence(s) (e.g. GS, SG, AEE, AES, GEPQ (SEQ ID NO:123), GEPS (SEQ ID NO:118)); some comprise several repeats of the humanized sequences or artificial sequences; some comprise a combination of the above. Several 6-residue sequences (6-mers) were designed. N-extensions could comprise one or more of a 6-mers, part of a 6-mers (e.g., 1-5 residues of a 6-mers), or a combination of the above. The amino acid residues of the artificial sequences (including 6-mers) and the humanized sequences could be arranged in any order.

Some representative 6-mers and combinations of 6-mers are listed in Table 2:

TABLE 2

| 6-mers and combinations of 6-mers | |
|---|---|
| 6-mers: | 6-mer-1: SPAGSP (SEQ ID NO: 4) |
| | 6-mer-2: TSESAT (SEQ ID NO: 5) |
| | 6-mer-3: TSTEPE (SEQ ID NO: 6) |
| | 6-mer-4: SEPATS (SEQ ID NO: 7) |
| | 6-mer-5: TSTEEG (SEQ ID NO: 8) |
| | 6-mer-6: PESGPG (SEQ ID NO: 9) |
| | 6-mer-7: SGSAPG (SEQ ID NO: 10) |
| | 6-mer-8: GSETPG (SEQ ID NO: 11) |
| Combinations: | SEPATSGSETPGSPAGSPTSTEEG (SEQ ID NO: 12) |
| | SEPATSGSETPGTSESATPESGPG (SEQ ID NO: 13) |
| | SEPATSGSETPGTSTEPESGSAPG (SEQ ID NO: 14) |
| | SEPATSGSETPGSPAGSPTSTEEGSPAGSP (SEQ ID NO: 15) |
| | SEPATSGSETPGTSESATPESGPGSPAGSP (SEQ ID NO: 16) |
| | SEPATSGSETPGTSTEPESGSAPGSPAGSP (SEQ ID NO: 17) |
| | SEPATSGSETPGSPAGSPTSTEEGTSESAT (SEQ ID NO: 18) |
| | SEPATSGSETPGTSESATPESGPGTSESAT (SEQ ID NO: 19) |
| | SEPATSGSETPGTSTEPESGSAPGTSESAT (SEQ ID NO: 20) |
| | SEPATSGSETPGSPAGSPTSTEEGTSTEPE (SEQ ID NO: 21) |
| | SEPATSGSETPGTSESATPESGPGTSTEPE (SEQ ID NO: 22) |
| | SEPATSGSETPGTSTEPESGSAPGTSTEPE (SEQ ID NO: 23) |
| | SEPATSGSETPGSPAGSPTSTEEGSEPATS (SEQ ID NO: 24) |
| | SEPATSGSETPGTSESATPESGPGSEPATS (SEQ ID NO: 25) |
| | SEPATSGSETPGTSTEPESGSAPGSEPATS (SEQ ID NO: 26) |
| | SEPATSGSETPGSPAGSPTSTEEGTSTEEG (SEQ ID NO: 27) |

TABLE 2-continued

| 6-mers and combinations of 6-mers |
|---|
| SEPATSGSETPGTSESATPESGPGTSTEEG (SEQ ID NO: 28) |
| SEPATSGSETPGTSTEPESGSAPGTSTEEG (SEQ ID NO: 29) |
| SEPATSGSETPGSPAGSPTSTEEGPESGPG (SEQ ID NO: 30) |
| SEPATSGSETPGTSESATPESGPGPESGPG (SEQ ID NO: 31) |
| SEPATSGSETPGTSTEPESGSAPGPESGPG (SEQ ID NO: 32) |
| SEPATSGSETPGSPAGSPTSTEEGSGSAPG (SEQ ID NO: 33) |
| SEPATSGSETPGTSESATPESGPGSGSAPG (SEQ ID NO: 34) |
| SEPATSGSETPGTSTEPESGSAPGSGSAPG (SEQ ID NO: 35) |
| SEPATSGSETPGSPAGSPTSTEEGGSETPG (SEQ ID NO: 36) |
| SEPATSGSETPGTSESATPESGPGGSETPG (SEQ ID NO: 37) |
| SEPATSGSETPGTSTEPESGSAPGGSETPG (SEQ ID NO: 38) |
| SEPATSGSETPGSPAGSPTSTEEGTSESATPESGPG (SEQ ID NO: 39) |
| SEPATSGSETPGSPAGSPTSTEEGSPAGSPTSTEEG (SEQ ID NO: 40) |
| SEPATSGSETPGSPAGSPTSTEEGTSTEPESGSAPG (SEQ ID NO: 41) |
| SEPATSGSETPGTSESATPESGPGSPAGSPTSTEEG (SEQ ID NO: 42) |
| SEPATSGSETPGTSESATPESGPGTSESATPESGPG (SEQ ID NO: 43) |
| SEPATSGSETPGTSESATPESGPGTSTEPESGSAPG (SEQ ID NO: 44) |
| SEPATSGSETPGTSESATPESGPGSEPATSGSETPG (SEQ ID NO: 45) |
| SEPATSGSETPGTSTEPESGSAPGSPAGSPTSTEEG (SEQ ID NO: 46) |
| SEPATSGSETPGTSTEPESGSAPGTSESATPESGPG (SEQ ID NO: 47) |
| SEPATSGSETPGTSTEPESGSAPGTSTEPESGSAPG (SEQ ID NO: 48) |
| SEPATSGSETPGTSTEPESGSAPGSEPATSGSETPG (SEQ ID NO: 49) |
| SEPATSGSETPGSEPATSGSETPGSPAGSPTSTEEG (SEQ ID NO: 50) |
| SEPATSGSETPGSEPATSGSETPGTSESATPESGPG (SEQ ID NO: 51) |
| SEPATSGSETPGSEPATSGSETPGTSTEPESGSAPG (SEQ ID NO: 52) |
| SEPATSGSETPGSEPATSGSETPGSEPATSGSETPG (SEQ ID NO: 53) |

TABLE 3

Examples of N-extensions

| SEQ ID NO | Residue number | Sequence of N-extension |
|---|---|---|
| SEQ ID NO: 54 | 6 | AEEAES |
| SEQ ID NO: 55 | 3 | AES |
| SEQ ID NO: 56 | 9 | (AEE)$_2$AES |
| SEQ ID NO: 57 | 20 | (GEPS)$_5$ |
| SEQ ID NO: 58 | 24 | SPAGSPTSTEEGTSESATPESGPG |

TABLE 3-continued

Examples of N-extensions

| SEQ ID NO | Residue number | Sequence of N-extension |
|---|---|---|
| SEQ ID NO: 59 | 21 | (AEE)$_6$AES |
| SEQ ID NO: 60 | 18 | (AEE)$_5$AES |
| SEQ ID NO: 61 | 12 | (AEE)$_3$AES |
| SEQ ID NO: 62 | 26 | AASPAGSPTSTEEGTSESATPESGPG |
| SEQ ID NO: 63 | 24 | TSESATPESGPGTSESATPESGPG |
| SEQ ID NO: 64 | 26 | AASPAGSPTSTEEGTSESATPESGPG |
| SEQ ID NO: 65 | 22 | AAPEDEETPEQEGSGSGSGSGS |
| SEQ ID NO: 66 | 12 | AAPEDEETPEQE |
| SEQ ID NO: 67 | 22 | AAPDEGTEEETEGSGSGSGSGS |
| SEQ ID NO: 68 | 24 | SEPATSGSETPGSEPATSGSETPG |
| SEQ ID NO: 69 | 25 | A(GPEQGQEP)$_3$ |
| SEQ ID NO: 70 | 30 | SEPATSGSETPGTSESATPESGPGTSTEPS |
| SEQ ID NO: 71 | 32 | SEPATSGSETPGTSESATPESGPGTSTEPSEG |
| SEQ ID NO: 72 | 24 | (GEPS)$_6$ |
| SEQ ID NO: 161 | 36 | (GEPS)$_9$ |
| SEQ ID NO: 162 | 36 | (GPEQ)$_9$ |
| SEQ ID NO: 163 | 25 | AGPEQGQEPGEPQGQEPQPGEPEGQ |

In-Sequence Mutations:

Certain internal residues of MIC-1 (SEQ ID NO:1) were modified, e.g. by substitution. For example, to increase the solubility of MIC-1 compounds, a hydrophobic residue of MIC-1 could be substituted with a hydrophilic residue, preferably by with an acidic residue; a positive charged residue could be substituted with an acidic residue, etc. To decrease oxidation, methionine could be substituted with other amino acids, e.g. E, F or L.

In-sequence mutations for increasing solubility include but are not limited to: P11E, H18E, R21E, A30E, A47E, R53E, A54E, M57E, R67E, L68E, K69E, A75E, A81E, P85E, L105E and K107E.

In-sequence mutations for decreasing oxidation include but are not limited to: M43L, M57E, M57L, M86F and M86L.

In-sequence mutations for increasing chemical stability include but are not limited to R2S, R2A, N3S N3E, N3A, N3T, N3P, N3G, N3V, N3H, N3Y and N3Q.

pI Calculation of MIC-1 Compounds

The calculated pI of a MIC-1 compound is defined as the pH at which the net calculated charge of the compound is zero. The calculated charge of the MIC-1 compound as a function of pH is obtained using the pKa values of the amino acid residues described in Table 1 and the method described by B. Skoog and A. Wichman (Trends in Analytical Chemistry, 1986, vol. 5, pp. 82-83). The side chain pKa of cysteine (Cys) is only included in the charge calculation for cysteines with a free sulfhydryl group. As an example the calculated pI value of human wtMIC-1 is 8.8 as the homodimer.

Herein, and throughout this document, pI calculations on MIC-1 compounds, if not stated otherwise, are made on MIC-1 compounds as homodimers.

TABLE 4

Calculated pI value of MIC-1 compounds comprising N-extension and MIC-1 (SEQ ID NO: 1)/MIC-1 analogues

| | MIC-1 (SEQ ID NO: 1) | MIC-1-des-N3 | MIC-1-Δ1-3 | MIC-1-Δ1-3 (M57E) | MIC-1-Δ1-3 (M57E, H66E) | MIC-1-Δ1-3 (M57E, R67E) | MIC-1-Δ1-3 (M57E, H66E and R67E) |
|---|---|---|---|---|---|---|---|
| Any combinations of four of 6mers 1-8 | 6.1 | 6.1 | 5.8 | 5.5 | 5.0 | 5.0 | 4.7 |
| Any combinations of five 6mers 1-8 | 5.8 | 5.8 | 5.5 | 5.2 | 4.8 | 4.8 | 4.6 |
| (GEPQ*)$_5$ or (GEPS*)$_5$ | 5.8 | 5.8 | 5.5 | 5.2 | 4.8 | 4.8 | 4.6 |
| (GEPQ*)6 | 5.5 | 5.5 | 5.2 | 5.2 | 4.7 | 4.7 | 4.5 |
| Humanized sequences in examples | 4.5~5.5 | 4.5~5.5 | 4.2~5.3 | 4.2~5.2 | 4.2~5.1 | 4.2~5.1 | 4.2~5.0 |

*The amino acid residues of "GEPQ" or "GEPS" may be arranged in any order

Materials and Methods
General Methods of Preparation

Example-1

Expression and Fermentation of the MIC-1 Compounds

The cDNA of MIC-1 compound was sub-cloned into a pET11b derived vector. Overexpression of MIC-1 compounds as inclusion bodies was induced in *E. coli* by 0.5 mM isopropyl β-d-thiogalactoside (IPTG) when the cell density reached an OD600 of 1.0. After continuous growth in TB for 20 h at 37° C., the cells were harvested and samples for both LC/MS and UPLC were prepared to confirm the molecular weight.

Fermentation was carried out on fed-batch process in chemical defined medium as supplement. Fermentation yield largely depended on different compounds, which varied from 1 g/L to 8 g/L from compound to compound.

Example-2

Purification and Refolding

The MIC-1 compounds were further purified as follows: Slurry (20% w/v) of *E. coli* in 10 mM Tris buffer pH 8.0 was sonicated (3 seconds on/off intervals on ice for 5 minutes) and the MIC-1 compounds was pelleted by centrifugation (10,000×g, for 30 minutes). The inclusion bodies were re-solubilised by 8 M urea in 20 mM Tris pH 8.0, and debris removed by centrifugation (10,000×g, for 30 minutes). The MIC-1 compounds in the resulting supernatant was collected and diluted into the refolding buffer (50 mM Tris, pH 8.5 and 10% DMF or 10% DMSO) to the final concentration of 0.1 mg/ml. The refolding process lasted for 48 hours in the cold room. The resulting solution was filtered by 0.4 μm filter and loaded onto Hydrophobic Interaction column or anion exchange chromatography (50 mM Tris pH 8.0, 0-500 mM NaCl) using Q Sepharose Fast Flow resin (GE Healthcare), as generally described in *Protein Purification*. Principles and Practice Series: Springer Advanced Texts in Chemistry Scopes, Robert K. 3rd ed., 1994 (Chapter 6 and Chapter 8). In some instances, further purification was done by size exclusion chromatography using a HiLoad 26/60 Superdex pg 75 column (GE Healthcare) operated with 50 mM Tris pH 8.0 and 200 mM NaCl. For storage, the MIC-1 compounds was transferred to DPBS, and stored frozen.

TABLE 5

Synthesized MIC-1 compounds or MIC-1 analogues and their maximal solubility at pH8 in Tris buffer tested according to Example 4

| SEQ ID NO | Structure | Calculated pI | Max. solubility (mg/ml) |
|---|---|---|---|
| SEQ ID NO: 1 | MIC-1 (SEQ ID NO: 1) | 8.8 | 0.3 |
| SEQ ID NO: 73 | MIC-1(R2A, N3E) | 6.8 | 0.9 |
| SEQ ID NO: 74 | MIC-1(R2A, N3E, A54E) | 6.4 | 1.0 |
| SEQ ID NO: 75 | MIC-1(R2A, N3E, A81E) | 6.4 | N.D.* |
| SEQ ID NO: 76 | MIC-1(R2A, N3E, H18E) | 6.2 | 1.7 |
| SEQ ID NO: 77 | MIC-1(R2A, N3E, K69E) | 6.1 | 2.2 |
| SEQ ID NO: 78 | MIC-1(R2A, N3E, K107E) | 6.1 | 1.9 |
| SEQ ID NO: 79 | MIC-1(R2A, N3E, L68E) | 6.4 | 3.9 |
| SEQ ID NO: 80 | MIC-1(R2A, N3E, A47E) | 6.4 | 1.0 |
| SEQ ID NO: 81 | MIC-1(R2A, N3E, L105E) | 6.4 | N.D. |
| SEQ ID NO: 82 | MIC-1(R2A, N3E, M57E) | 6.4 | 1.7 |
| SEQ ID NO: 83 | MIC-1(R2A, N3E, P85E) | 6.4 | N.D. |
| SEQ ID NO: 84 | MIC-1(R2A, N3E, P11E) | 6.4 | 1.6 |
| SEQ ID NO: 85 | MIC-1(R2A, N3E, R21E) | 6.1 | 1.8 |
| SEQ ID NO: 86 | MIC-1(R2A, N3E, R53E) | 6.1 | 1.9 |
| SEQ ID NO: 87 | MIC-1(R2A, N3E, R67E) | 6.1 | 1.8 |
| SEQ ID NO: 88 | MIC-1(R2A, N3E, A30E) | 6.4 | 1.5 |
| SEQ ID NO: 89 | AEEAES-MIC-1-Δ1-3 | 6.1 | N.D. |
| SEQ ID NO: 90 | AES-MIC-1-Δ1-3 | 6.8 | 0.9 |
| SEQ ID NO: 91 | (AEE)$_2$AES-MIC-1-Δ1-3 | 5.5 | N.D. |
| SEQ ID NO: 92 | (GEPS)$_5$-MIC-1 (SEQ ID NO: 1) | 5.8 | 35.1 |

TABLE 5-continued

Synthesized MIC-1 compounds or MIC-1 analogues and their maximal solubility at pH8 in Tris buffer tested according to Example 4

| SEQ ID NO | Structure | Calculated pI | Max. solubility (mg/ml) |
|---|---|---|---|
| SEQ ID NO: 93 | SPAGSPTSTEEGTSESATPESGPG-MIC-1(SEQ ID NO: 1) | 6.1 | 44.5 |
| SEQ ID NO: 94 | (AEE)₆AES-MIC-1(SEQ ID NO: 1) | 4.5 | 39.0 |
| SEQ ID NO: 95 | (AEE)₅AES-MIC-1-Δ1-3 | 4.6 | 35.0 |
| SEQ ID NO: 96 | (AEE)₃AES-MIC-1-Δ1-3 | 5.0 | 36.0 |
| SEQ ID NO: 97 | AASPAGSPTSTEEGTSESATPESGPG-MIC-1(SEQ ID NO: 1) | 6.1 | N.D. |
| SEQ ID NO: 98 | TSESATPESGPGTSESATPESGPG-MIC-1(R2A, N3E) | 5.5 | N.D. |
| SEQ ID NO: 99 | AASPAGSPTSTEEGTSESATPESGPG-MIC-1-Δ1-3 | 5.8 | N.D. |
| SEQ ID NO: 100 | AAPEDEETPEQEGSGSGSGSGS-MIC-1-Δ1-3 | 5.2 | 35.7 |
| SEQ ID NO: 101 | AAPEDEETPEQE-MIC-1-Δ1-3 | 5.2 | N.D. |
| SEQ ID NO: 102 | AAPDEGTEEETEGSGSGSGSGS-MIC-1-Δ1-3 | 5.2 | N.D. |
| SEQ ID NO: 103 | SEPATSGSETPGTSTEPSEGSAPG-MIC-1-Δ1-3 | 5.8 | N.D. |
| SEQ ID NO: 104 | (SEPATSGSETPG)₂-MIC-1-Δ1-3 | 5.8 | 35.4 |
| SEQ ID NO: 105 | (SEPATSGSETPG)₂-MIC-1-Δ1-3(M57E) | 5.5 | 37.1 |
| SEQ ID NO: 106 | (SEPATSGSETPG)₂-MIC-1-Δ1-3(M57L) | 5.8 | 32.5 |
| SEQ ID NO: 107 | A(GPEQGQEP)₃-MIC-1-Δ1-3 | 5.2 | 32.2 |
| SEQ ID NO: 108 | SEPATSGSETPGTSESATPESGPGTSTEPS-MIC-1-Δ1-3 | 5.5 | 40.0 |
| SEQ ID NO: 109 | SEPATSGSETPGTSESATPESGPG TSTEPSEG-MIC-1-Δ1-3 | 5.2 | 40.0 |
| SEQ ID NO: 110 | (SEPATSGSETPG)₂-MIC-1-Δ1-3(M86L) | 5.8 | N.D. |
| SEQ ID NO: 111 | (SEPATSGSETPG)₂-MIC-1-Δ1-3(M57L, M86L) | 5.8 | 31.1 |
| SEQ ID NO: 112 | (SEPATSGSETPG)₂-MIC-1-Δ1-3(M57E, H66E) | 5.0 | N.D. |
| SEQ ID NO: 113 | (SEPATSGSETPG)₂-MIC-1-Δ1-3(M57E, R67E) | 5.0 | N.D. |
| SEQ ID NO: 114 | (SEPATSGSETPG)₂-MIC-1-Δ1-3(M57E, R67E, M86L) | 5.0 | N.D. |
| SEQ ID NO: 115 | SEPATSGSETPGTSESATPESGPGTSTEPSG-MIC-1-Δ1-3(M57L, M86L) | 5.5 | N.D. |
| SEQ ID NO: 116 | (GEPS)₆-MIC-1-Δ1-3 | 5.2 | N.D. |
| SEQ ID NO: 117 | (SEPATSGSETPG)₂-MIC-1-des-N3 | 6.1 | N.D. |

*N.D.: Not determined

Example-3 pH-Dependent Solubility of MIC-1 Compounds of the Invention

The purpose of this experiment was to screen for the MIC-1 compounds with improved solubility, and determine the optimal pH window for formulation.

MIC-1 compounds were dissolved in a mixture of water and ethanol (60% water and 40% ethanol) with a concentration range between 3 mg/ml to 10 mg/ml. The solvent was evaporated with SpeedVac (Concentrator Plus, Eppendorf) for 6 hours to obtain pellet of said MIC-1 compound.

Below buffers were used for this pH-dependent solubility curve assay: acetate buffer (pH 3 to pH 6); Tris buffer (pH 7 to pH 9); CAPS buffer (pH 10 to pH 11).

Buffers were added into each well of the 96-well plate together with MIC-1 compounds. The amount used may not be exactly the same but all targeting a theoretical concentration within 12-18 mg/ml. The concentration of MIC-1 compounds in the supernatant was determined by UPLC (Table 6). Based on the results, solubility of the MIC-1 compounds of the invention was significantly improved between pH 6-9 compared with wtMIC-1. The optimal pH window of the MIC-1 compounds falls into the pH range that is preferred for formulation, e.g. pH 6.5-8.5.

TABLE 6 pH-dependent solubility test of MIC-1 analogues (mg/ml)

| SEQ ID NO | Structure | pH | | | | | | | | |
|---|---|---|---|---|---|---|---|---|---|---|
| | | 3.0 | 4.0 | 5.0 | 6.0 | 7.0 | 8.0 | 9.0 | 10.0 | 11.0 |
| SEQ ID NO: 1 | MIC-1 (SEQ ID NO: 1) | 12.8 | 2.0 | 0.2 | 0.3 | 0.2 | 0.3 | 0.6 | 3.6 | 13.9 |
| SEQ ID NO: 74 | MIC-1 (R2A, N3E, A54E) | 13.3 | 1.3 | 0.4 | 0.6 | 0.5 | 1.0 | 1.5 | 3.6 | 15.5 |
| SEQ ID NO: 76 | MIC-1 (R2A, N3E, H18E) | 14.5 | 3.4 | 0.4 | 0.4 | 0.9 | 1.7 | 3.0 | 14.3 | 13.6 |
| SEQ ID NO: 79 | MIC-1 (R2A, N3E, L68E) | 13.6 | 1.4 | 1.4 | 1.7 | 3.2 | 3.9 | 3.9 | 4.0 | 12.1 |
| SEQ ID NO: 80 | MIC-1 (R2A, N3E, A47E) | 13.4 | 2.5 | 0.5 | 0.6 | 0.9 | 1.0 | 1.0 | 2.9 | 10.8 |
| SEQ ID NO: 85 | MIC-1 (R2A, N3E, R21E) | 14.9 | 1.6 | 0.5 | 0.5 | 1.4 | 1.8 | 1.7 | 2.5 | 12.9 |
| SEQ ID NO: 88 | MIC-1 (R2A, N3E, A30E) | 13.9 | 1.7 | 0.8 | 0.8 | 1.4 | 1.5 | 2.1 | 2.4 | 13.7 |
| SEQ ID NO: 90 | AES-MIC-1-Δ1-3 | 12.5 | 2.3 | 0.6 | 0.7 | 1.2 | 0.9 | 1.0 | 3.6 | 8.9 |
| SEQ ID NO: 93 | SPAGSPTSTEEGTSESATPESGPG-MIC-1 (SEQ ID NO: 1) | 12.9 | 1.5 | 1.2 | 1.4 | 5.1 | 12.8 | 13.0 | 13.0 | 13.5 |
| SEQ ID NO: 94 | (AEE)$_6$AES-MIC-1-Δ1-3 | 7.3 | 0.2 | 2.9 | 9.5 | 11.6 | 15.3 | 15.1 | 15.0 | 14.8 |
| SEQ ID NO: 95 | (AEE)$_5$AES-MIC-1-Δ1-3 | 11.9 | 0.3 | 1.6 | 5.7 | 9.4 | 15.8 | 15.7 | 14.9 | 15.0 |
| SEQ ID NO: 100 | AAPEDEETPEQEGSGSGSGSGS-MIC-1-Δ1-3 | 11.2 | 3.2 | 2.1 | 5.1 | 8.3 | 15.0 | 15.3 | 15.0 | 15.6 |
| SEQ ID NO: 104 | (SEPATSGSETPG)$_2$-MIC-1-Δ1-3 | 12.2 | 0.7 | 0.3 | 1.0 | 4.6 | 16.4 | 16.9 | 16.0 | 16.2 |
| SEQ ID NO: 105 | (SEPATSGSETPG)$_2$-MIC-1-Δ1-3(M57E) | 7.2 | 1.2 | 0.8 | 3.8 | 11.5 | 15.6 | 15.2 | 14.9 | 16.2 |
| SEQ ID NO: 106 | (SEPATSGSETPG)2-MIC-1-Δ1-3(M57L) | 10.1 | 0.2 | 0.3 | 1.6 | 4.3 | 15.6 | 16.1 | 16.1 | 16.8 |

Example 4

Maximal Solubility of MIC-1 Compounds at pH 8

In order to test the maximal solubility, the MIC-1 compounds were dissolved in a mixture of water and ethanol (60% water and 40% ethanol) with a concentration range between 3 mg/ml to 10 mg/ml. Then the solution (150 μL each well) was aliquot into a 96-well plate (Corning). The solvent was evaporated with SpeedVac (Concentrator Plus, Eppendorf) for 6 hours to obtain pellet of the MIC-1 compound. Tris buffer (pH 8.0, without excipients) was added into each well of the 96-well plate. The amount of buffer added to the well was less than the amount needed for solving the whole pellet in the well, so that maximal concentration was achieved. The plate was shaken on a plate shaker at 800 rpm (MixMate, Eppendorf) for 2 hours. The pellet was spun down at 3600 g for 5 min. The supernatants were transferred to a 96-deep-well plate and diluted 20 times with 40% ethanol. Then all of the samples were subject to UPLC (Acquity, Waters), plate reader (Infinite M200 pro, Tecan) and UV spectrometer (NanoDrop 8000, Thermo Scientific) to determine the concentration (Table 7).

Based on the results, solubility of the MIC-1 compounds of the invention was significantly improved at pH 8.0. Especially, the MIC-1 compounds with N-extensions achieved solubility of more than 30 mg/ml at pH 8.0.

TABLE 7

Max solubility test of MIC-1 compounds at pH 8.0

| SEQ IN NO | Structure | Solubility (mg/ml) |
| --- | --- | --- |
| SEQ ID NO: 96 | (AEE)$_3$AES-MIC-1-Δ1-3 | 36.0 |
| SEQ ID NO: 95 | (AEE)$_5$AES-MIC-1-Δ1-3 | 35.0 |
| SEQ ID NO: 94 | (AEE)$_6$AES-MIC-1 (SEQ ID NO: 1) | 39.0 |
| SEQ ID NO: 93 | SPAGSPTSTEEGTSESATPESGPG-MIC-1 | 44.5 |
| SEQ ID NO: 92 | (GEPS)$_5$-MIC-1 (SEQ ID NO: 1) | 35.1 |
| SEQ ID NO: 100 | AAPEDEETPEQEGSGSGSGSGS-MIC-1-Δ1-3 | 35.7 |
| SEQ ID NO: 79 | MIC-1(R2A, N3E, L68E) | 3.9 |
| SEQ ID NO: 85 | MIC-1(R2A, N3E, R21E) | 1.8 |
| SEQ ID NO: 88 | MIC-1(R2A, N3E, A30E) | 1.5 |
| SEQ ID NO: 74 | MIC-1(R2A, N3E, A54E) | 1.0 |
| SEQ ID NO: 76 | MIC-1(R2A, N3E, H18E) | 1.7 |
| SEQ ID NO: 77 | MIC-1(R2A, N3E, K69E) | 2.2 |
| SEQ ID NO: 80 | MIC-1(R2A, N3E, A47E) | 1.0 |
| SEQ ID NO: 90 | AES-MIC-1-Δ1-3 | 0.9 |
| SEQ ID NO: 78 | MIC-1(R2A, N3E, K107E) | 1.9 |
| SEQ ID NO: 82 | MIC-1(R2A, N3E, M57E) | 1.7 |
| SEQ ID NO: 84 | MIC-1(R2A, N3E, P11E) | 1.6 |
| SEQ ID NO: 86 | MIC-1(R2A, N3E, R53E) | 1.9 |
| SEQ ID NO: 87 | MIC-1(R2A, N3E, R67E) | 1.8 |
| SEQ ID NO: 104 | (SEPATSGSETPG)$_2$-MIC-1-Δ1-3 | 35.4 |
| SEQ ID NO: 105 | (SEPATSGSETPG)$_2$-MIC-1-Δ1-3(M57E) | 37.1 |
| SEQ ID NO: 106 | (SEPATSGSETPG)$_2$-MIC-1-Δ1-3(M57L) | 32.5 |
| SEQ ID NO: 107 | A(GPEQGQEP)$_3$-MIC-1-Δ1-3 | 32.2 |
| SEQ ID NO: 108 | SEPATSGSETPGTSESATPESGPGTSTEPS-MIC-1-Δ1-3 | 40.0 |
| SEQ ID NO: 109 | SEPATSGSETPGTSESATPESGPG TSTEPSEG-MIC-1-Δ1-3 | 40.0 |

TABLE 7-continued

Max solubility test of MIC-1 compounds at pH 8.0

| SEQ IN NO | Structure | Solubility (mg/ml) |
|---|---|---|
| SEQ ID NO: 111 | (SEPATSGSETPG)$_2$-MIC-1-Δ1-3(M57L, M86L) | 31.1 |
| SEQ ID NO: 73 | MIC-1(R2A, N3E) | 0.9 |
| SEQ ID NO: 164 | SEPATSGSETPGTSESATPESGPGTSTEPSEG-MIC-1-des-N3 (M57L, M86L) | 40.0 |
| SEQ ID NO: 1 | MIC-1 (SEQ ID NO: 1) | 0.3 |

General Methods of In Vitro Activity Screening

Example 5

Establishment of BHK21-hGFRAL-IRES-hRET Cell Line

The purpose of this example was to establish a cell based in vitro assay for testing MIC-1 activity. Mammalian cells were transfected and stably expressed full length MIC-1 receptor (hGFRAL) and its full signaling co-receptor hRET51.

Plasmids expressing full length hGFRAL and full length hRET51 were constructed by inserting synthesized DNA nucleotides encoding full length hGFRAL and full length hRET51 into mammalian expression vector pEL. IRES (internal ribosome entry site) is a commonly used linker between two DNA sequences, so that the two DNA sequences can be simultaneously translated into mRNA. pEL vector backbone was provided by Taihegene CRO company.

Two millions of BHK21 cells were seeded in a 10 cm petri dish and cultured for overnight in culture medium (DMEM+10% FBS+1% PS). Cells were transfected with pEL-hGFRAL-IRES-hRET plasmids. Transfected cells were split into new 10 cm dishes at different densities and grew in selection medium (DMEM+10% FBS+1% PS+1mg/ml G418) for more than 2 weeks to get single clones. The single clones were transferred to 6 well plates and cultured to 100% confluence. mRNA expression of hGFRAL and hRET was measured by qPCR. Successfully transfected clones were picked up and tested for MIC-1 binding (FIG. 15 and Table 13).

Example 6

MIC-1 Cell-Based In Vitro Activity Assay wtMIC-1 and MIC-1 compounds induced both phosphorylation of ERK1/2 in BHK21-hGFRAL-IRES-hRET stable cells (Table 8). It can be concluded from the results that the ternary complex of MIC-1, GFRAL and RET phosphorylates RET protein tyrosine kinase to induce in vivo activities of MIC-1 through signal pathways comprising ERK/MAPK pathway by phosphorylation of ERK1/2.

Results from screening MIC-1 compounds using BHK21-hGFRAL-IRES-hRET is shown in Table 8. MIC-1 compounds with N-extensions only or MIC-1 analogues with in-sequence mutations only achieved in vitro activity equal to or even higher than wtMIC-1. Also, combination of N-extension and in-sequence mutations can also achieve similar activity.

TABLE 8

In vitro activity of MIC-1 compounds

| SEQ IN NO | Structure | pERK EC50 (nM) | Emax (%) |
|---|---|---|---|
| SEQ ID NO: 1 | MIC-1 (SEQ ID NO: 1) | 0.3 | 100% |
| SEQ ID NO: 73 | MIC-1(R2A, N3E) | 0.3 | 100% |
| SEQ ID NO: 74 | MIC-1(R2A, N3E, A54E) | 0.3 | 100% |
| SEQ ID NO: 75 | MIC-1(R2A, N3E, A81E) | 0.3 | 100% |
| SEQ ID NO: 76 | MIC-1(R2A, N3E, H18E) | 0.5 | 100% |
| SEQ ID NO: 77 | MIC-1(R2A, N3E, K69E) | 0.5 | 100% |
| SEQ ID NO: 78 | MIC-1(R2A, N3E, K107E) | 0.3 | 100% |

TABLE 8-continued

In vitro activity of MIC-1 compounds

| SEQ IN NO | Structure | pERK EC50 (nM) | Emax (%) |
|---|---|---|---|
| SEQ ID NO: 79 | MIC-1(R2A, N3E, L68E) | 0.8 | 100% |
| SEQ ID NO: 80 | MIC-1(R2A, N3E, A47E) | 0.4 | 100% |
| SEQ ID NO: 81 | MIC-1(R2A, N3E, L105E) | 0.7 | 100% |
| SEQ ID NO: 82 | MIC-1(R2A, N3E, M57E) | 0.3 | 70% |
| SEQ ID NO: 83 | MIC-1(R2A, N3E, P85E) | 0.6 | 100% |
| SEQ ID NO: 84 | MIC-1(R2A, N3E, P11E) | 0.4 | 100% |
| SEQ ID NO: 85 | MIC-1(R2A, N3E, R21E) | 0.6 | 100% |
| SEQ ID NO: 86 | MIC-1(R2A, N3E, R53E) | 0.4 | 100% |
| SEQ ID NO: 87 | MIC-1(R2A, N3E, R67E) | 0.5 | 100% |
| SEQ ID NO: 88 | MIC-1(R2A, N3E, A30E) | 0.7 | 100% |
| SEQ ID NO: 89 | AEEAES-MIC-1-Δ1-3 | 0.3 | 100% |
| SEQ ID NO: 90 | AES-MIC-1-Δ1-3 | 0.3 | 100% |
| SEQ ID NO: 91 | (AEE)$_2$AES-MIC-1-Δ1-3 | 0.4 | 100% |
| SEQ ID NO: 92 | (GEPS)$_5$-MIC-1 (SEQ ID NO: 1) | 0.5 | 100% |
| SEQ ID NO: 93 | SPAGSPTSTEEGTSESATPESGPG-MIC-1 (SEQ ID NO: 1) | 0.4 | 100% |
| SEQ ID NO: 94 | (AEE)$_6$AES-MIC-1 | 0.8 | 100% |
| SEQ ID NO: 95 | (AEE)$_5$AES-MIC-1-Δ1-3 | 0.5 | 100% |
| SEQ ID NO: 96 | (AEE)$_3$AES-MIC-1-Δ1-3 | 0.5 | 100% |
| SEQ ID NO: 97 | AASPAGSPTSTEEGTSESATPESGPG-MIC-1 (SEQ ID NO: 1) | 0.4 | 100% |
| SEQ ID NO: 98 | TSESATPESGPGTSESATPESGPG-MIC-1 (R2A, N3E) | 0.3 | 100% |
| SEQ ID NO: 99 | AASPAGSPTSTEEGTSESATPESGPG-MIC-1-Δ1-3 | 0.7 | 100% |
| SEQ ID NO: 100 | AAPEDEETPEQEGSGSGSGSGS-MIC-1-Δ1-3 | 0.5 | 100% |
| SEQ ID NO: 101 | AAPEDEETPEQE-MIC-1-Δ1-3 | 0.5 | 100% |

TABLE 8-continued

In vitro activity of MIC-1 compounds

| SEQ IN NO | Structure | pERK EC50 (nM) | Emax (%) |
|---|---|---|---|
| SEQ ID NO: 102 | AAPDEGTEEETEGSGSGSGSGS-MIC-1-Δ1-3 | 0.5 | 100% |
| SEQ ID NO: 103 | SEPATSGSETPGTSTEPESGSAPG-MIC-1-Δ1-3 | 0.7 | 100% |
| SEQ ID NO: 104 | (SEPATSGSETPG)$_2$-MIC-1-Δ1-3 | 0.4 | 100% |
| SEQ ID NO: 105 | (SEPATSGSETPG)$_2$-MIC-1-Δ1-3(M57E) | 0.6 | 60% |
| SEQ ID NO: 106 | (SEPATSGSETPG)$_2$-MIC-1-Δ1-3(M57L) | 0.6 | 100% |
| SEQ ID NO: 107 | A(GPEQGQEP)3-MIC-1-Δ1-3 | 0.8 | 100% |
| SEQ ID NO: 108 | SEPATSGSETPGTSESATPESGPGTSTEPS-MIC-1-Δ1-3 | 0.4 | 100% |
| SEQ ID NO: 109 | SEPATSGSETPGTSESATPESGPG TSTEPSEG-MIC-1-Δ1-3 | 0.4 | 100% |
| SEQ ID NO: 110 | (SEPATSGSETPG)$_2$-MIC-1-Δ1-3(M86L) | 0.4 | 100% |
| SEQ ID NO: 111 | (SEPATSGSETPG)$_2$-MIC-1-Δ1-3 (M57L, M86L) | 0.4 | 100% |

Increasing solubility of MIC-1 may also be achieved by N-terminal fusion of MIC-1 polypeptides with Human Serum Albumin (HSA). It is known that HSA fusion could increase the solubility of MIC-1. Two such HSA-MIC-1 fusion proteins were tested for in vitro activity (Table 9).

TABLE 9 pERK EC50 of HSA-MIC-1 conjugates

| HSA-MIC-1 fusion protein | pERK EC50 (nM) | Calculated pI |
|---|---|---|
| HSA-GGSSSGS (SEQ ID NO: 152)-MIC-1 (SEQ ID NO: 1) | 3.6 | 6.2 |
| HSA-PTPTPTPTPTPTPTPTPTPTPTPTPTPTP (SEQ ID NO: 153)-MIC-1 (SEQ ID NO: 1) | 4.5 | 6.2 |

A significant loss of potency was observed, thus demonstrating that these MIC-1 fusion proteins with high solubility did not retain receptor potency.

In Vivo Efficacy

Example 7

Effect of MIC-1 Compounds on Food Intake in Lean Sprague Dawley Rats

The in vivo efficacy of MIC-1 compounds of the invention was measured in 9-11 weeks old lean male Sprague Dawley rats. Animals were injected once daily with a dose of 8 nmol/kg body weight (4 nmol/kg for two HSA-MIC-1 fusion proteins) 1-2 hrs before the onset of the dark period. Compounds were administrate subcutaneously (1-4 ml/kg) in appropriate buffered solution. Changes in food intake were measured by automatic food monitoring systems (BioDAQ system and HM2 system for rat). In the BioDAQ system animals were single housed; and in the HM2 system animals were in group housed with up to 3 animals per cage. Each compound was tested in n=4-8 animals. Animals were acclimatized for at least 7 days prior to the experiment. Collected data are expressed as daily food intake (24 hour food intake) measured from the onset of each daily 12 hour dark phase to the next day dark phase. Daily changes in food intake in response to administrated compound were calculated by subtracting the average daily food intake of the vehicle group from the average daily food intake of the treatment group. Changes were considered significant if $p<0.1$ using a two-tailed student's t-test (). Results are expressed as the "maximum reduction" in food intake compared with vehicle (percentage) recorded during the study period. Data are also expressed as the "accumulated reduction" in food intake which as the sum of significant ($p<0.1$) daily reductions in food intake (percentage) during the study period.

TABLE 10

Effect of daily doses (8 nmol/kg) of MIC-1 compounds on food intake in lean SD rats.

| SEQ ID NO | NNC | Maximum Efficacy (%) | Accumulated Efficacy (%) |
|---|---|---|---|
| SEQ ID NO: 1 | MIC-1 (SEQ ID NO: 1) | 68 | 361 |
| SEQ ID NO: 77 | MIC-1(R2A, N3E, K69E) | 46 | 247 |
| SEQ ID NO: 82 | MIC-1(R2A, N3E, M57E) | 72 | 395 |
| SEQ ID NO: 92 | (GEPS)$_5$-MIC-1 (SEQ ID NO: 1) | 84 | 469 |
| SEQ ID NO: 97 | AASPAGSPTSTEEGTSESATPESGPG-MIC-1 (SEQ ID NO: 1) | 90 | 456 |
| SEQ ID NO: 98 | TSESATPESGPGTSESATPESGPG-MIC-1(R2A, N3E) | 90 | 503 |
| SEQ ID NO: 100 | AAPEDEETPEQEGSGSGSGSGS-MIC-1-Δ1-3 | 84 | 446 |
| SEQ ID NO: 101 | AAPEDEETPEQE-MIC-1-Δ1-3 | 75 | 408 |
| SEQ ID NO: 102 | AAPDEGTEEETEGSGSGSGSGS-MIC-1-Δ1-3 | 82 | 423 |
| SEQ ID NO: 103 | SEPATSGSETPGTSTEPESGSAPG-MIC-1-Δ1-3 | 82 | 452 |
| SEQ ID NO: 104 | (SEPATSGSETPG)$_2$-MIC-1-Δ1-3 | 93 | 509 |
| SEQ ID NO: 105 | (SEPATSGSETPG)$_2$-MIC-1-Δ1-3 (M57E) | 97 | 532 |
| SEQ ID NO: 106 | (SEPATSGSETPG)$_2$-MIC-1-Δ1-3 (M57L) | 99 | 532 |
| SEQ ID NO: 107 | A(GPEQGQEP)$_3$-MIC-1-Δ1-3 | 81 | 395 |
| SEQ ID NO: 108 | SEPATSGSETPGTSESATPESGPGTSTEPS-MIC-1-Δ1-3 | 80 | 448 |
| SEQ ID NO: 165 | A(GPEQGQEPGEPQGQEPQPGEPEGQ)-MIC-1-Δ1-3 | 78 | 382 |
| SEQ ID NO: 109 | SEPATSGSETPGTSESATPESGPGTSTEPSEG-MIC-1-Δ1-3 | 82 | 445 |
| SEQ ID NO: 110 | (SEPATSGSETPG)$_2$-MIC-1-Δ1-3 (M86L) | 70 | 398 |
| SEQ ID NO: 111 | (SEPATSGSETPG)$_2$-MIC-1-Δ1-3 (M57L/M86L) | 85 | 462 |
| SEQ ID NO: 112 | (SEPATSGSETPG)$_2$-MIC-1-Δ1-3 (M57E/H66E) | 80 | 369 |
| SEQ ID NO: 113 | (SEPATSGSETPG)$_2$-MIC-1-Δ1-3 (M57E/R67E) | 67 | 266 |
| N/A | HSA-GGSSSGS (SEQ ID NO: 152)-MIC-1 (SEQ ID NO: 1)* | 28 | 72 |
| N/A | HSA-PTPTPTPTPTPTPTPTPTPTPTPTPTP (SEQ ID NO: 153)-MIC-1 (SEQ ID NO: 1)* | 23 | 23 |

Note:
*means the dose of administration is 4 nmol/kg body weight.

The inventors surprisingly found that these MIC-1 compounds not only increased the solubility molecules but also resulted in efficacy equal to or even better than wtMIC-1 (Table 10). For instance compounds according to SEQ ID NO:105 and SEQ ID NO:106 had a maximum and accumulated in vivo efficacy which was 40-50% greater than wtMIC-1 with subcutaneous dosing. The increase in efficacy was furthermore associated with an increase in solubility as compounds according to SEQ ID NO:92, SEQ ID NO:104, SEQ ID NO:105 and SEQ ID NO:106 all had elevated solubility and a significant greater in vivo efficacy compared with wtMIC-1. This correlation seems not to be explained by changes in the in vitro Emax as all compounds in table 10, except compound according to SEQ ID NO:105, had an Emax comparable with wtMIC-1. In fact, compound SEQ ID NO:105 had a lower Emax than wtMIC-1 and was still more efficacious than wtMIC-1 in vivo. Also, the in vitro potencies were comparable between compounds as none of the compounds had an EC50 which differed from wtMIC-1. Thus, the association between increased in vivo efficacies and increased solubility is surprising and cannot be simply be explained by changes in increased receptor activation in vitro.

Example 8

MIC-1 Expression and Initial Met Removal Efficiency of Different 12-mer Blocks

In the human body, N-Formyl-Methionine is recognized by the immune system as foreign material, or as an alarm signal released by damaged cells, and stimulates the body to fight against potential infection (Pathologic Basis of Veterinary Disease5: Pathologic Basis of Veterinary Disease, By James F. Zachary, M. Donald McGavin). In addition, Methionine is an instable residue that could be easily oxidized. Therefore, the N-Met cleavage efficiency is very important to MIC-1 expression.

There are 4 different types of 12mers, and all of them are comprised of 3 Ser, 2 Pro, 2 Gly, 2 Thr, 2 Glu and 1 Ala. However, the 12 residues in each repeat are arranged in different ways.

Little is known about the effects of different 12mers on the expression level and the N-Met cleavage efficiency. Thus, systematically investigation of MIC-1 compounds initiating with single and double 12mers respectively is quite necessary.

The cDNA of MIC-1 compound was sub-cloned into a pET11b derived vector. Overexpression of MIC-1 compounds as inclusion bodies or soluble protein was induced in E. coli by 0.5mM isopropyl β-d-thiogalactoside (IPTG) when the cell density reached an OD600 of 1.0. After continuous growth in TB for 20 h at 37° C., the cells were harvested and sonicated in buffer A (20 mM Tris, pH 8.0). The resulting mixture was centrifugated at 10,000 g for 20 min and analysed by LC/MS and SDS-PAGE to confirm the molecular weight.

Fermentation was carried out on fed-batch process in chemical defined medium as supplement. Fermentation yield largely depended on different compounds, which varied from 1 g/L to 8 g/L from compound to compound.

Compounds designed for the single-12mer test and the result are shown in Table 11 and FIG. 1.

TABLE 11

Initial Met removal efficiency of single 12-mer building blocks

| N-extension | N-aa sequence | MIC-1 Backbone | N-Met cleavage efficiency (%) |
|---|---|---|---|
| 12mer-1 | SPAGSPTSTEEG (SEQ ID NO: 166) | MIC-1 del (1-3) | N/A |
| 12mer-2 | TSESATPESGPG (SEQ ID NO: 167) | | 0 |
| 12mer-3 | TSTEPSEGSAPG (SEQ ID NO: 168) | | 0 |
| 12mer-4 | SEPATSGSETPG (SEQ ID NO: 169) | | 100 |

N/A: means MIC-1 with the N-extension did not express in E.coli.

Figure 2:
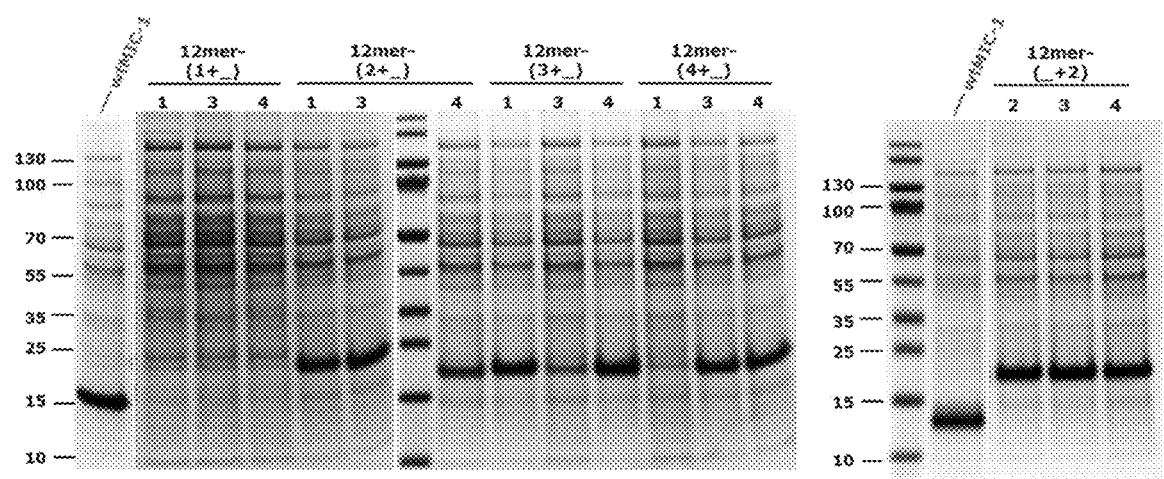
FIG. 2: The expression of MIC-1 compounds with double 12-mer building blocks. All cells were grown in TB at 37° C. and proteins were induced to express by adding 0.5 mM IPTG after OD600 reached 1.0. Cells were harvested after overnight and the expression level was checked by loading the total lysate on SDS-PAGE. wtMIC-1 was loaded as the positive control.

Compounds bearing double 12 mers are listed in Table 12, and the results are shown as well (see Table 12 and FIG. 2).

TABLE 12

Initial Met removal efficiency of double 12-mers building blocks

| SEQ ID NO | N-extension | N-aa sequence | MIC-1 backbone | N-Met cleavage efficiency (%) |
|---|---|---|---|---|
| N/A | 12mer-(1 + 1) | SPAGSPTSTEEG-SPAGSPTSTEEG (SEQ ID NO: 170) | MIC-1 del(1-3) | N/A |
| N/A | 12mer-(1 + 3) | SPAGSPTSTEEG-TSTEPSEGSAPG (SEQ ID NO: 171) | | N/A |
| N/A | 12mer-(1 + 4) | SPAGSPTSTEEG-SEPATSGSETPG (SEQ ID NO: 172) | | N/A |
| N/A | 12mer-(2 + 1) | TSESATPESGPG-SPAGSPTSTEEG (SEQ ID NO: 173) | | 58.1 |
| N/A | 12mer-(2 + 2) | TSESATPESGPG-TSESATPESGPG (SEQ ID NO: 174) | | 30.0 |
| N/A | 12mer-(2 + 3) | TSESATPESGPG-TSTEPSEGSAPG (SEQ ID NO: 175) | | 58.5 |
| N/A | 12mer-(2 + 4) | TSESATPESGPG-SEPATSGSETPG (SEQ ID NO: 176) | | 64.5 |

TABLE 12-continued

Initial Met removal efficiency of double 12-mers building blocks

| SEQ ID NO | N-extension | N-aa sequence | MIC-1 backbone | N-Met cleavage efficiency (%) |
|---|---|---|---|---|
| N/A | 12mer-(3 + 1) | TSTEPSEGSAPG-SPAGSPTSTEEG (SEQ ID NO: 177) | | 10.0 |
| N/A | 12mer-(3 + 2) | TSTEPSEGSAPG-TSESATPESGPG (SEQ ID NO: 178) | | 1.0 |
| N/A | 12mer-(3 + 3) | TSTEPESGSAPG-TSTEPESGSAPG (SEQ ID NO: 179) | | 26.4 |
| N/A | 12mer-(3 + 4) | TSTEPSEGSAPG-SEPATSGSETPG (SEQ ID NO: 180) | | 10.5 |
| N/A | 12mer-(4 + 1) | SEPATSGSETPG-SPAGSPTSTEEG (SEQ ID NO: 12) | | N/A |
| SEQ ID NO: 182 | 12mer-(4 + 2) | SEPATSGSETPG-TSESATPESGPG (SEQ ID NO: 13) | | 100 |
| SEQ ID NO: 103 | 12mer-(4 + 3) | SEPATSGSETPG-TSTEPSEGSAPG (SEQ ID NO: 14) | | 100 |
| SEQ ID NO: 104 | 12mer-(4 + 4) | SEPATSGSETPG-SEPATSGSETPG (SEQ ID NO: 181) | | 100 |

N/A: means MIC-1 compound with the N-extension did not express in E.coli

In conclusion, N-extensions starting with the 12mer-1 block could not be expressed in *E. coli*. For the other 12mer blocks, protein expression was achieved but only 12mer-4 as the initial sequence resulted in complete methionine cleavage. In addition, the N-met cleavage efficiency of 12mer-2 series is better than that of 12mer-3 series.

Example 9

Figure 3:
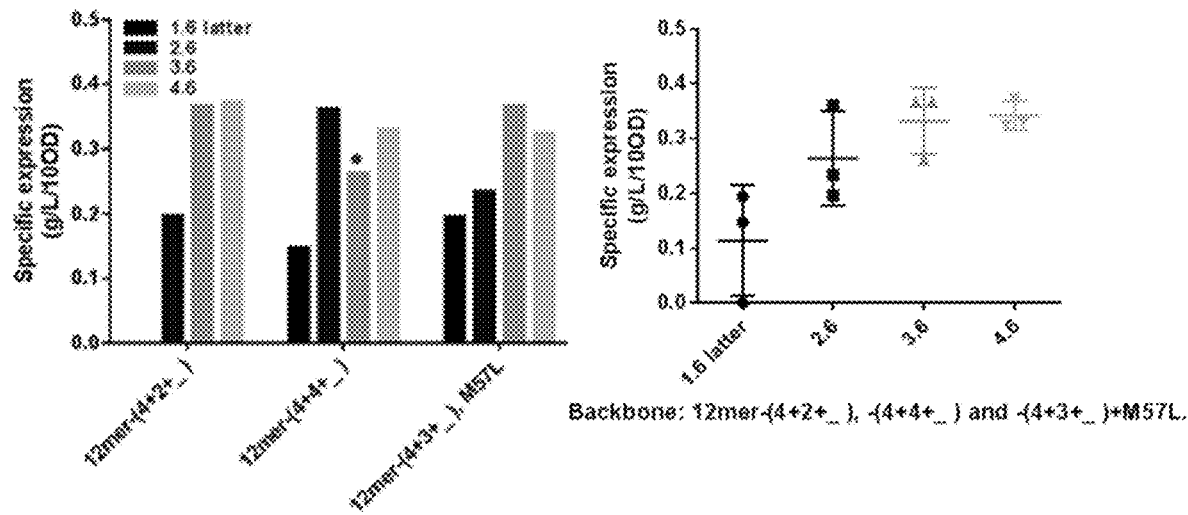
FIG. 3: a) comparison of expression levels among MIC-1 compounds initiating with 12mer-(4+2+_), -(4+4+_) and -(4+3+_). It should be noticed that the group bearing 12mer-(4+3_) and the construct indicated by the dot contain M57L in the backbone of MIC-1. b) the effects of the extended 12mers on the expression level. In addition, the lowest data point in the group of 3.6 is the MIC-1 compound containing M57L. In this figure, "1.6 latter" represents TSTEEG, "2.6" represents TSESAT, "3.6" represents TSTEPS and "4.6" represents SEPATS.
Figure 4:
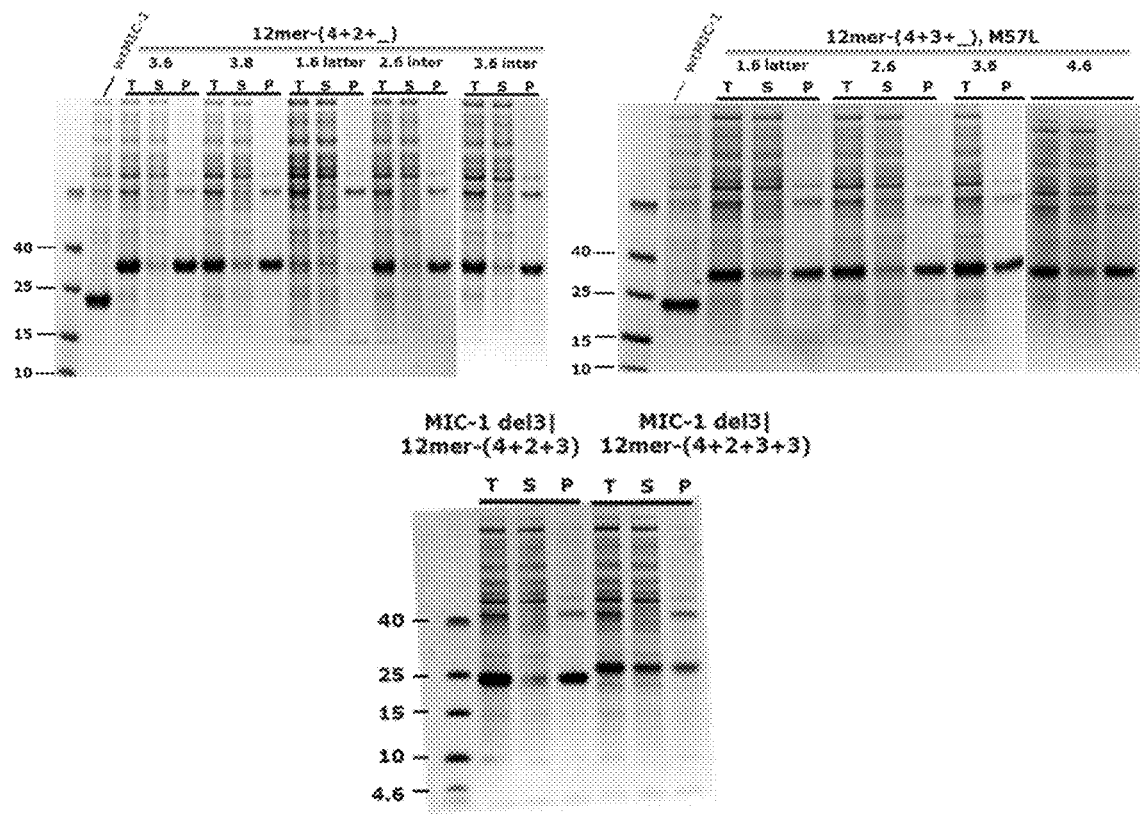
FIG. 4: SDS-PAGE of representatives bearing 12mer-(4+2+_), 12mer-(4+3+_)+M57L, 12mer-(three repeats) and 12mer-(four repeats). T: total protein, S: soluble fraction, P: cell pellet (inclusion body).

Expression Level and Inclusion Body Ratio of MIC-1 Peptide Compound with 2* or 2.5*12mer N-Extension (1) Expression of MIC-1 Compound with 2.5*12mer N-Extension See Example 8 for protein production method. The results are shown in Table 13, FIG. 3 and FIG. 4.

TABLE 13

Constructs and protein production for 2.5 * 12mer test

| SEQ ID NO | N-extension | N-aa sequence | MIC-1 backbone | UPLC Shaker Flask (g/L/10 OD) | UPLC Fermenter (g/L/10 OD) |
|---|---|---|---|---|---|
| SEQ ID NO: 200 | 12mer-(4 + 2 + 1.6 latter) | SEPATSGSETPG TSESATPESGPG TSTEEG (SEQ ID NO: 28) | MIC-1 del(1-3) | N/A | |
| SEQ ID NO: 201 | 12mer-(4 + 2 + 2.6) | SEPATSGSETPG TSESATPESGPG TSESAT (SEQ ID NO: 19) | | 0.197 | |
| SEQ ID NO: 202 | 12mer-(4 + 2 + 2.6 inter) | SEPATSGSETPG TSESATPESGPG ESATPE (SEQ ID NO: 183) | | 0.206 | |
| SEQ ID NO: 108 | 12mer-(4 + 2 + 3.6) | SEPATSGSETPG TSESATPESGPG TSTEPS (SEQ ID NO: 70) | | 0.367 | 0.374 |

TABLE 13-continued

Constructs and protein production for 2.5 * 12mer test

| SEQ ID NO | N-extension | N-aa sequence | MIC-1 backbone | UPLC Shaker Flask (g/L/10 OD) | UPLC Fermenter (g/L/10 OD) |
|---|---|---|---|---|---|
| SEQ ID NO: 203 | 12mer-(4 + 2 + 3.6 inter) | SEPATSGSETPG TSESATPESGPG STEPSE (SEQ ID NO: 184) | | 0.243 | |
| SEQ ID NO: 109 | 12mer-(4 + 2 + 3.8) | SEPATSGSETPG TSESATPESGPG TSTEPSEG (SEQ ID NO: 71) | | 0.273 | 0.162 |
| SEQ ID NO: 204 | 12mer-(4 + 2 + 4.6) | SEPATSGSETPG TSESATPESGPG SEPATS (SEQ ID NO: 25) | | 0.373 | |
| SEQ ID NO: 205 | 12mer-(4 + 3 + 1.6 latter) | SEPATSGSETPG TSTEPSEGSAPG TSTEEG (SEQ ID NO: 185) | MIC-1 del (1-3), M57L | 0.195 | |
| SEQ ID NO: 206 | 12mer-(4 + 3 + 2.6) | SEPATSGSETPG TSTEPSEGSAPG TSESAT (SEQ ID NO: 186) | | 0.234 | |
| SEQ ID NO: 207 | 12mer-(4 + 3 + 3.6) | SEPATSGSETPG TSTEPSEGSAPG TSTEPS (SEQ ID NO: 187) | | 0.367 | |
| SEQ ID NO: 208 | 12mer-(4 + 3 + 4.6) | SEPATSGSETPG TSTEPSEGSAPG SEPATS (SEQ ID NO: 188) | | 0.324 | |
| SEQ ID NO: 209 | 12mer-(4 + 4 + 1.6 latter) | SEPATSGSETPG SEPATSGSETPG TSTEEG (SEQ ID NO: 189) | MIC-1 del (1-3), M57L | 0.148 | |
| SEQ ID NO: 210 | 12mer-(4 + 4 + 2.6) | SEPATSGSETPG SEPATSGSETPG TSESAT (SEQ ID NO: 190) | MIC-1 del(1-3) | 0.361 | |
| SEQ ID NO: 211 | 12mer-(4 + 4 + 2.6 inter) | SEPATSGSETPG SEPATSGSETPG ESATPE (SEQ ID NO: 191) | | N/A | |
| SEQ ID NO: 212 | 12mer-(4 + 4 + 3.6) | SEPATSGSETPG SEPATSGSETPG TSTEPS (SEQ ID NO: 192) | MIC-1 del (1-3), M57L | 0.262 | |

TABLE 13-continued

Constructs and protein production for 2.5 * 12mer test

| SEQ ID NO | N-extension | N-aa sequence | MIC-1 backbone | UPLC Shaker Flask (g/L/10 OD) | UPLC Fermenter (g/L/10 OD) |
|---|---|---|---|---|---|
| SEQ ID NO: 213 | 12mer-(4 + 4 + 3.6 inter2) | SEPATSGSETPG SEPATSGSETPG STEPSE (SEQ ID NO: 193) | MIC-1 del(1-3) | N/A | |
| SEQ ID NO: 214 | 12mer-(4 + 4 + 4.6) | SEPATSGSETPG SEPATSGSETPG SEPATS (SEQ ID NO: 194) | | 0.330 | |

Notes:
".6" means the first 6aa of 12mers, "latter" means the last 6aa of 12mers, "inter" means the internal 6aa from 12mers.

Although the extended 12mer (baa) locate 24aa away from the N-terminal, the expression levels of MIC-1 compound vary a lot among different groups. It is clear that the fragment from 12mer-1 is not suitable for expression, which is consistent with previous results. The average expression levels of 12mer-(4+_+3.6) and -(4+_+4.6) are relatively higher than others.

(2) Inclusion Body Ratio of MIC-1 Compound with 2* or 2.5*12mer N-Extension

For large scale protein production, inclusion body is usually considered as a good choice mainly due to its better up-scaling properties, which mainly include: high expression level, simple recovery step and high purity, protease-resistant and good process stability.

MIC-1 compounds could be expressed either inclusion body or soluble form, which is mainly dependent on compounds' pI and extension length. The results are shown in Table 14 and FIG. 4.

TABLE 14

MIC-1 compound's solubility in cell cytosol and their pI values

| SEQ ID NO | N-extension | Sequences of N-extension | MIC-1 backbone | Inclusion body ratio★ | pI values |
|---|---|---|---|---|---|
| SEQ ID NO: 104 | 12mer-(4 + 4) | SEPATSGSETPG SEPATSGSETPG (SEQ ID NO: 181) | MIC-1 del(1-3) | 100% | 5.8 |
| SEQ ID NO: 108 | 12mer-(4 + 2 + 3.6) | SEPATSGSETPG TSESATPESG PGTSTEPS (SEQ ID NO: 70) | | 100% | 5.5 |
| SEQ ID NO: 109 | 12mer-(4 + 2 + 3.8) | SEPATSGSETPG TSESATPESG PGTSTEPSEG (SEQ ID NO: 71) | | 90% | 5.2 |
| SEQ ID NO: 215 | 12mer-(4 + 2)-GPEQGPEQ | SEPATSGSETPG TSESATPESG PGGPEQGPEQ (SEQ ID NO: 195) | | 90% | 5.2 |
| SEQ ID NO: 216 | 12mer-(4 + 2)-GEPSGEPS | SEPATSGSETPG TSESATPESG PG GEPSGEPS (SEQ ID NO: 196) | | 95% | 5.2 |

TABLE 14-continued

MIC-1 compound's solubility in cell cytosol and their pI values

| SEQ ID NO | N-extension | Sequences of N-extension | MIC-1 backbone | Inclusion body ratio★ | pI values |
|---|---|---|---|---|---|
| SEQ ID NO:112 | 12mer-(4 + 4) M57E, H66E | SEPATSGSET PG SEPATSGSET PG (SEQ ID NO: 181) | | 70% | 5.0 |
| SEQ ID NO:113 | 12mer-(4 + 4) M57E, R67E | SEPATSGSET PG SEPATSGSET PG (SEQ ID NO: 181) | | 70% | 5.0 |
| SEQ ID NO: 217 | 12mer-(three repeats) | SEPATSGSET PG TSESATPESG PG TSTEPSEGSA PG (SEQ ID NO: 197) | MIC-1-des-N3 | 85% | 5.4 |
| SEQ ID NO: 218 | 12mer-(four repeats) | SEPATSGSET PG TSESATPESG PG TSTEPSEGSA PG TSTEPSEGSA PG (SEQ ID NO: 198) | MIC-1-des-N3 | 30% | 5.1 |
| SEQ ID NO: 219 | 12mer-(five repeats) | SPAGSPTSTE EGTSESATPE SGPGTSTEPS EGSAPGSPA GSPTSTEEGT STEPSEGSAP G (SEQ ID NO: 199) | MIC-1 | 0% | 4.8 |
| SEQ ID NO: 220 | 12mer-(4 + 4) M57E, H66E, R67E | SEPATSGSET PG SEPATSGSET PG (SEQ ID NO: 181) | MIC-1 del(1-3) | 0% | 4.7 |
| SEQ ID NO: 221 | 12mer-(4 + 2 + 3.6) M57E, R67E | SEPATSGSET PG TSESATPESG PGTSTEPS (SEQ ID NO: 70) | | 0% | 4.7 |

Note:
★The number here is estimated by SDS-PAGE.

Figure 5:
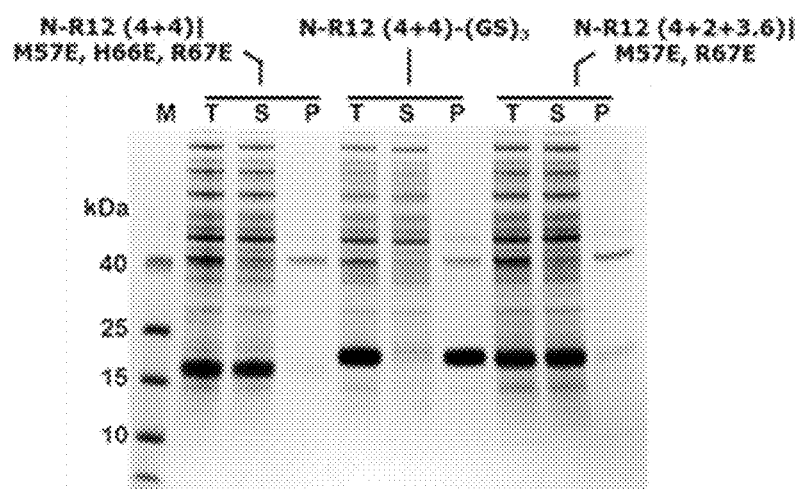
FIG. 5: Solubility of MIC-1 compounds with in-sequence mutations. In this figure, the backbone is MIC-1 del(1-3).

The solubility of MIC-1 compounds with in-sequence mutations are shown in Table 15 and FIG. 5 (the backbone is MIC-1 del(1-3)).

TABLE 15

Solubility of MIC-1 compound with in-sequence mutations

| N-extension | In-sequence M | Solublity in cell |
|---|---|---|
| SEPATSGSETPG | M57E | IBs |
| SEPATSGSETPG | M57E/H66E | Partially soluble |
| (12mer-(4 + 4)) (SEQ ID NO: 181) | M57E/H66E/R67E | Fully soluble |

TABLE 15-continued

Solubility of MIC-1 compound with in-sequence mutations

| N-extension | In-sequence M | Solublity in cell |
| --- | --- | --- |
| SEPATSGSETPG | M57E | N.D. |
| TSESATPESGPG- | M57E/H66E | Fully soluble |
| TSTEPS | M57E/H66E/R67E | Fully soluble |
| (12mer- | | |
| (4 + 2 + 3.6)} | | |
| (SEQ ID NO: 70) | | |

MIC-1 compounds initiating with 12mer-(4+2+_), -(4+4+_) and -(4+3+_) were investigated with their ability to express inclusion body. It was shown that the inclusion body ratio is >90% when pI>5.1. In addition, MIC-1 compounds with in-sequence mutations M57E/H66E mainly expressed soluble fractions.

The invention claimed is:

1. A MIC-1 compound comprising a MIC-1 polypeptide and an N-terminal amino acid extension, wherein the compound comprises an amino acid sequence according to SEQ ID NO: 100, 104, 106, 107, 108, 109, 111, 112, 113, 114, 115, 116, 117 or 164.

* * * * *